(12) United States Patent
Desai

(10) Patent No.: US 12,059,418 B2
(45) Date of Patent: Aug. 13, 2024

(54) PLASMODIAL SURFACE ANION CHANNEL INHIBITORS FOR THE TREATMENT OR PREVENTION OF MALARIA

(71) Applicant: The United States of America, as represented by the Secretary, Department of Health and Human Services, Bethesda, MD (US)

(72) Inventor: Sanjay A. Desai, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 672 days.

(21) Appl. No.: 17/115,317

(22) Filed: Dec. 8, 2020

(65) Prior Publication Data

US 2021/0085679 A1 Mar. 25, 2021

Related U.S. Application Data

(62) Division of application No. 16/292,722, filed on Mar. 5, 2019, now Pat. No. 10,869,865, which is a division
(Continued)

(51) Int. Cl.
| | |
|---|---|
| *A61K 31/519* | (2006.01) |
| *A61K 31/42* | (2006.01) |
| *A61K 31/422* | (2006.01) |
| *A61K 31/423* | (2006.01) |
| *A61K 31/427* | (2006.01) |
| *A61K 31/433* | (2006.01) |
| *A61K 31/4355* | (2006.01) |
| *A61K 31/437* | (2006.01) |
| *A61K 31/4439* | (2006.01) |
| *A61K 31/4741* | (2006.01) |
| *A61K 31/495* | (2006.01) |

(Continued)

(52) U.S. Cl.
CPC ............ *A61K 31/501* (2013.01); *A61K 31/42* (2013.01); *A61K 31/422* (2013.01); *A61K 31/423* (2013.01); *A61K 31/427* (2013.01); *A61K 31/433* (2013.01); *A61K 31/4355* (2013.01); *A61K 31/437* (2013.01); *A61K 31/4439* (2013.01); *A61K 31/4741* (2013.01); *A61K 31/495* (2013.01); *A61K 31/496* (2013.01); *A61K 31/498* (2013.01); *A61K 31/50* (2013.01); *A61K 31/517* (2013.01); *A61K 31/519* (2013.01); *A61K 31/554* (2013.01); *A61K 39/015* (2013.01); *A61K 45/06* (2013.01); *C07D 239/84* (2013.01); *C07D 241/44* (2013.01); *C07D 263/57* (2013.01); *C07D 277/54* (2013.01); *C07D 281/16* (2013.01); *C07D 409/04* (2013.01); *C07D 409/14* (2013.01); *C07D 413/14* (2013.01); *C07D 417/06* (2013.01); *C07D 491/048* (2013.01); *C07D 498/04* (2013.01); *C07D 513/04* (2013.01); *C07K 14/445* (2013.01); *C07K 16/205* (2013.01); *C07K 2319/21* (2013.01); *C07K 2319/43* (2013.01); *Y02A 50/30* (2018.01)

(58) Field of Classification Search
CPC .. C07D 409/04; C07D 409/14; C07D 413/14; C07D 417/06; A61K 31/496; A61K 31/498; A61K 31/501; A61K 31/506; A61K 45/06
See application file for complete search history.

(56) References Cited

U.S. PATENT DOCUMENTS

| | | |
|---|---|---|
| 2,895,956 A | 7/1959 | Tuppy |
| 6,602,865 B1 | 8/2003 | Andrasi et al. |

(Continued)

FOREIGN PATENT DOCUMENTS

| | | | | |
|---|---|---|---|---|
| FR | 2604705 A | * | 4/1988 | .......... C07D 215/44 |
| WO | 00/27851 A1 | | 5/2000 | |

(Continued)

OTHER PUBLICATIONS

Alkhalil et al., "Plasmodium falciparum likely encodes the principal anion channel on infected human erythrocytes," *Blood*, 104, 4279-86 (2004).
(Continued)

*Primary Examiner* — Theodore R. Howell
*Assistant Examiner* — George W Kosturko
(74) *Attorney, Agent, or Firm* — Leydig, Voit & Mayer, Ltd.

(57) ABSTRACT

The invention provides methods of treating or preventing malaria comprising administering to an animal an effective amount of a compound of formula I:

$$Q-Y-R^1-R^2 \quad (I),$$

wherein Q, Y, $R^1$, and $R^2$ are as described herein. Methods of inhibiting a plasmodial surface anion channel of a parasite in an animal are also provided. The invention also provides pharmaceutical compositions comprising a compound represented by formula I in combination with any one or more compounds represented by formulas II, V, and VI. Use of the pharmaceutical compositions for treating or preventing malaria or for inhibiting a plasmodial surface anion channel in animals including humans are also provided. Also provided by the invention are clag3 amino acid sequences and related nucleic acids, vectors, host cells, populations of cells, antibodies, and pharmaceutical compositions.

8 Claims, 5 Drawing Sheets
Specification includes a Sequence Listing.

Related U.S. Application Data of application No. 15/723,677, filed on Oct. 3, 2017, now Pat. No. 10,265,313, which is a division of application No. 15/072,902, filed on Mar. 17, 2016, now Pat. No. 9,808,458, which is a division of application No. 14/111,256, filed as application No. PCT/US2012/033072 on Apr. 11, 2012, now Pat. No. 9,320,786.

(60) Provisional application No. 61/474,583, filed on Apr. 12, 2011.

(51) Int. Cl.

| | | |
|---|---|---|
| A61K 31/496 | (2006.01) | |
| A61K 31/498 | (2006.01) | |
| A61K 31/50 | (2006.01) | |
| A61K 31/501 | (2006.01) | |
| A61K 31/517 | (2006.01) | |
| A61K 31/554 | (2006.01) | |
| A61K 39/015 | (2006.01) | |
| A61K 45/06 | (2006.01) | |
| C07D 239/84 | (2006.01) | |
| C07D 241/44 | (2006.01) | |
| C07D 263/57 | (2006.01) | |
| C07D 277/54 | (2006.01) | |
| C07D 281/16 | (2006.01) | |
| C07D 409/04 | (2006.01) | |
| C07D 409/14 | (2006.01) | |
| C07D 413/14 | (2006.01) | |
| C07D 417/06 | (2006.01) | |
| C07D 491/048 | (2006.01) | |
| C07D 498/04 | (2006.01) | |
| C07D 513/04 | (2006.01) | |
| C07K 14/445 | (2006.01) | |
| C07K 16/20 | (2006.01) | |

(56) References Cited

U.S. PATENT DOCUMENTS

| | | | | |
|---|---|---|---|---|
| 10,869,865 | B2 * | 12/2020 | Desai | C07D 263/57 |
| 10,881,669 | B2 * | 1/2021 | Desai | A61K 45/06 |
| 2006/0135447 | A1 | 6/2006 | Chupak et al. | |
| 2011/0144107 | A1 | 6/2011 | Chatterjee et al. | |

FOREIGN PATENT DOCUMENTS

| | | | | |
|---|---|---|---|---|
| WO | WO-02056884 A2 * | 7/2002 | | A61K 31/4178 |
| WO | WO-2006019768 A1 * | 2/2006 | | C07D 401/14 |
| WO | 2007/008541 A2 | 1/2007 | | |
| WO | 2009/137081 A2 | 11/2009 | | |
| WO | 2009/152356 A2 | 12/2009 | | |
| WO | 2010/011537 A1 | 1/2010 | | |
| WO | WO-2010011537 A1 * | 1/2010 | | A61K 31/165 |

OTHER PUBLICATIONS

Asahi et al., "Hypoxanthine: a low molecular weight factor essential for growth of erythrocytic plasmodium falciparum in a serum-free medium," *Parasitology*, 113, 19-23 (1996).

Balu et al., "High-efficiency transformation of plasmodium falciparum by the lepidopteran transposable element piggyback," *PNAS*, 102 (45), 16391-96 (2005).

Balu et al., "PiggyBac is an effective tool for functional analysis of the plasmodium falciparum genome," *BMC Microbiology*, 9, 83 (2009).

Baumeister et al., "Evidence for the involvement of plasmodium falciparum proteins in the formation of new permeability pathways in the erythrocyte membrane," *Mol. Microbiol.*, 60(2), 493-504 (2006).

Bhargava et al., "Synthesis of 6,8-dibromo-3-substituted 2-(N,N-dialkyl(or N-piperidino-) carboxamidomethylthio)-4(3H)-quinazolinones as antimalarials," *J. Med. Chem.*, 11 (4), 908-909 (1968).

Bokhari et al., "High Guanidinium Permeability Reveals Dehydration-Dependent Ion Selectivity in the Plasmodial Surface Anion Channel" *BioMed Research International*, pp. 1-8 (2014).

Bokhari et al., "Two distinct mechanisms of transport through the plasmodial surface anion channel," *J. Membr. Biol.*, 226, 27-34 (2008).

Broman et al., "QTL mapping in experimental crosses," *Bioinformatics*, 19, 889-890 (2003).

Chen et al., "Developmental selection of var gene expression in plasmodium falciparum," *Nature*, 394, 392-95 (1998).

Cortes et al., "Epigenetic silencing of plasmodium falciparum genes linked to erythrocyte invasion," *PLoS Pathog.*, 3, e107 (2007).

"Cytoadherence linked asexual protein 3.1, [Plasmodium falciparum 3D7]," GenBank XP_001351099(124504713) (2010).

"Cytoadherence linked asexual protein 3.1, [Plasmodium falciparum 3D7]," GenBank XP_001351100(CAB10572.2) (2010).

Desai et al., "A nutrient-permeable channel on the intraerythrocytic malaria parasite," *Nature*, 362, 643-646 (1993).

Desai et al., "Open and closed states of the plasmodial surface anion channel," *Nanomedicine*, 1(1), 58-66 (2005).

Desai et al., "Pore size of the malaria parasite's nutrient channel," *PNAS*, 94(5), 2045-2049 (1997).

Desai et al., "A voltage-dependent channel involved in nutrient uptake by red blood cells infected with the malaria parasite," *Nature*, 406, 1001-05 (2000).

Dickerman et al., "Identification of inhibitors that dually target the new permeability pathway and dihydroorotate dehydrogenase in the blood stage of Plasmodium falciparum," *Scientific Reports*, 6: 37502 (pp. 1-15) (2016).

European Patent Office, Supplementary Search Report in European Patent Application No. 12770599.4 (Jul. 22, 2014).

Fidock et al., "Transformation with human dihydrofolate reductase renders malaria parasites insensitive to WR99210 but does not affect the intrinsic activity of proguanil," *PNAS*, 94, 10931-36 (1997).

Freitas-Junior et al., "Frequent ectopic recombination of virulence factor genes in telomeric chromosome clusters of P. falciparum," *Nature*, 407, 1018-22 (2000).

Fujiki et al., "Isolation of intracellular membranes by means of sodium carbonate treatment: application to endoplasmic reticulum," *J. Cell Biol.*, 93, 97-102 (1982).

Gemma et al., "Malaria Chemotherapy: Recent Advances in Drug Development," *Recent Patents on Anti-Infective Drug Discovery*, 5, 195-225 (2010).

Gero et al., "New nucleoside transport pathways induced in the host erythrocyte membrane of malaria and babesia infected cells," *Adv. Exp. Med. Biol.*, 309A, 169-172 (1991).

Gibson et al., "Diversity oriented syntheses of fused pyrimidines designed as potential antifolates," *Org. Biomol. Chem.*, 7 (9), 1829-1842 (2009).

Ginsburg et al., "Characterization of permeation pathways appearing in the host membrane of plasmodium falciparum infected red blood cells," *Mol. Biochem. Parasitol.*, 14, 313-22 (1985).

Howitt et al., "Clonally variant gene families in plasmodium falciparum share a common activation factor," *Mol. Microbiol.*, 73, 1171-85 (2009).

International Search Report, International Application No. PCT/US 12/33072, mailed Oct. 16, 2012.

Ito et al., "An essential dual-function complex mediates erythrocyte invasion and channel-mediated nutrient uptake in malaria parasites" *eLife*, pp. 1-24, published Feb. 21, 2017.

Kall et al., "An HMM posterior decoder for sequence feature prediction that includes homology information," *Bioinformatics*, 21, 1251-51 (2005).

(56) References Cited

OTHER PUBLICATIONS

Kaneko et al., "Apical expression of three RhopH1/Clag proteins as components of the plasmodium falciparum RhopH complex," *Mol. Biochem. Parasitol.*, 143(1), 20-8 (2005).
Kang et al., "Malaria parasites are rapidly killed by dantrolene derivatives specific for the plasmodial surface anion channel," *Mol. Pharmacol.*, 68, 34-40 (2005).
Kelly et al., "Selective killing of the human malaria parasite plasmodium falciparum by a benzylthiazolium dye," *Exp. Parasitol.*, 116(2), 103-110 (2007).
Kilejian et al., "Selective association of a fragment of the knob protein with spectrin, actin and the red cell membrane," *Mol. Biochem. Parasitol.*, 44(2), 175-81 (1991).
Krogh et al., "Predicting transmembrane protein topology with a hidden Markov model: application to complete genomes," *J. Mol. Biol.*, 305, 567-80 (2001).
Krungkrai et al., "Malaria parasite carbonic anhydrase: inhibition of aromatic/heterocyclic sulfonamides and its therapeutic potential," *Asian Pacific Journal of Tropical Biomedicine*, 233-242 (2011).
Kumar et al., "Discovery of a Rhodanine Class of Compounds as Inhibitors of Plasmodium falciparum Enoyl-Acyl Carrier Protein Reductase" *J Med. Chem.* 50, 2665-2675 (2007) with supporting information, pp. 1-14.
Lambros et al., "Synchronization of plasmodium falciparum erythrocytic stages in culture," *J. Parasitol.*, 65(3), 418-20 (1979).
Lavazec et al., "Expression switching in the stevor and Pfmc-2TM superfamilies in Plasmodium falciparum," *Mol. Microbiol.*, 64(6), 1621-34 (2007).
Lisk et al., "The plasmodial surface anion channel is functionally conserved in divergent malaria parasites," *Eukaryotic Cell*, 4, 2153-2159 (2005).
Lisk et al., "Changes in the plasmodial surface anion channel reduce leupeptin uptake and can confer drug resistance in plasmodium falciparum-infected erythrocytes," *Antimicrob. Agents Chemother.*, 52, 2346-54 (2008).
Liu et al., "Functional profiling, identification, and inhibition of plasmepsins in intraerythrocytic malaria parasites," *Angew. Chem. Int. Ed.*, 48, 8293-8297 (2009).
Marshall et al., "A critical assessment of the use of microculture tetrazolium assays to measure cell growth and function," *Growth Regul.*, 5(2), 69-84 (1995).
Marti et al., "Targeting malaria virulence and remodeling proteins to the host erythrocyte," *Science*, 306, 1930-33 (2004).
Matsuhisa et al., "Binary solute adsorption of dosed drugs on serum albumin," *Chem. Engineering J.*, 34, B21-B27 (1987).
National Institute of Allergy and Infectious Diseases, "Malaria Prevention, Treatment and Control Strategies," accessed online at <niaid.nih.gov/diseases-conditions/malaria-strategies> on Jul. 6, 2018 p. 1-2 (2011).
Nguitragool et al., "Malaria parasite clag3 genes determine channel-mediated nutrient uptake by infected red blood cells," *Cell*, 145, 665-677 (2011).

Olepu et al., "2-Oxo-tetrahydro-1,8-naphthyridines as selective inhibitors of malarial protein farnesyltransferase and as antimalarials," *Bioorg. Med. Chem. Lett.*, 18, 494-497 (2008).
Pillai et al., "A cell-based high-throughput screen validates the plasmodial surface anion channel as an antimalarial target," *Mol. Pharmacol.*, 77, 724-33 (2010).
Pillai et al., "Solute restriction reveals an essential role for clag3-associated channels in malaria parasite nutrient acquisition," *Mol. Pharmacol.*, 82(6), 1104-14 (2012).
"Plasmodium falciparum 3D7 Cytoadherence linked asexual protein 3.1 (RhopH1(3.1)) mRNA, complete cds," GenBank XM_001351063(124504712) (2010).
"Plasmodium falciparum 3D7 Cytoadherence linked asexual protein 3.1 (RhopH1(3.1)) mRNA, complete cds," GenBank XM_001351064(124504714) (2010).
Price et al., "FastTree: computing large minimum evolution trees with profiles instead of distance matrix," *Mol. Biol. Evol.*, 26, 1641-50 (2009).
Saliba et al., "Transport and metabolism of the essential vitamin pantothenic acid in human erythrocytes infected with the malaria parasite plasmodium falciparum," *J. Biol. Chem.*, 273 (17), 10190-95 (1998).
Sato et al., "Media for culture of mammalian cells," *Curr. Protoc. Cell Biol.*, 1, Unit 1.2 (2001).
Sherf et al., "Antigenic variation in plasmodium falciparum," *Annu. Rev. Microbiol.*, 62, 445-470 (2008).
Sigworth et al., "Data transformations for improved display and fitting of single-channel dwell time histograms," *Biophys. J.*, 52, 1047-54 (1987).
Spielmann et al., "Protein export in malaria parasites: do multiple export motifs add up to multiple export pathways?" *Trends Parasitol.*, 26(1), 6-10 (2010).
Su et al., "A genetic map and recombination parameters of the human malaria parasite plasmodium falciparum," *Science*, 286, 1351-53 (1999).
Vinsensini et al., "The RhopH complex is transferred to the host cells cytoplasm following red blood cell invasion by plasmodium falciparum," *Mol. Biochem. Parrasitol.*, 160, 81-89 (2008).
Wagner et al., "A two-compartment model of osmotic lysis in plasmodium faciparum-infected erythrocytes," *Biophysical J.*, 84, 116-23 (2003).
Wellems et al., "Chloroquine resistance not linked to mdr-like genes in a plasmodium falciparum cross," *Nature*, 345, 253-55 (1990).
Whitelaw, "Can Malaria be Prevented," accessed online at <health24.com/Medical/Malaria/Overview/Can-malaria-be-prevented-20130205 (2018).
Written Opinion, International Application No. PCT/US2012/33072, mailed Oct. 16, 2012.
Zhu et al., "2-(3,4-dihydro-4-oxothieno[2,3-d]pyrimidin-2-ylthio) acetamides as a new class of falcipain-2 inhibitors. 3. design, synthesis and biological evaluation," *Molecules*, 14 (2), 785-797 (2009).

\* cited by examiner

PLASMODIAL SURFACE ANION CHANNEL INHIBITORS FOR THE TREATMENT OR PREVENTION OF MALARIA

CROSS-REFERENCE TO RELATED APPLICATIONS

This patent application is a divisional of co-pending U.S. patent application Ser. No. 16/292,722, filed on Mar. 5, 2019, which is a divisional of U.S. patent application Ser. No. 15/723,677, filed Oct. 3, 2017, now U.S. Pat. No. 10,265,313, which in turn is a divisional of U.S. patent application Ser. No. 15/072,902, filed Mar. 17, 2016, now U.S. Pat. No. 9,808,458, which in turn is a divisional of U.S. patent application Ser. No. 14/111,256, filed Nov. 7, 2013, now U.S. Pat. No. 9,320,786, which is the U.S. National Phase of International Patent Application No. PCT/US2012/033072, filed Apr. 11, 2012, which claims the benefit of U.S. Provisional Patent Application No. 61/474,583, filed Apr. 12, 2011, the disclosure of each of which is incorporated by reference in its entirety herein for all purposes.

STATEMENT REGARDING FEDERALLY SPONSORED RESEARCH AND DEVELOPMENT

This invention was made with Government support under project number ZIA AI000882-17 by the National Institutes of Health, National Institute of Allergy and Infectious Diseases. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 85,208 Byte ASCII (Text) file named "751344ST25.txt," dated Dec. 7, 2020.

BACKGROUND OF THE INVENTION

Malaria, one of the world's most important infectious diseases, is transmitted by mosquitoes and is caused by four species of *Plasmodium* parasites (*P. falciparum, P. vivax, P. ovale, P. malariae*). Symptoms include fever, chills, headache, muscle aches, tiredness, nausea and vomiting, diarrhea, anemia, and jaundice. Convulsions, coma, severe anemia and kidney failure can also occur. It remains a leading cause of death globally, especially amongst African children under 5 years of age. While repeated infections over many years leads to partial immunity in endemic areas, these adults still suffer significant morbidity and loss of productivity. The annual economic loss in Africa due to malaria is estimated at US $12 billion.

There is no effective vaccine currently available for malaria. Treatment has therefore relied primarily on antimalarial drugs such as chloroquine. Because some malaria parasites have acquired resistance to each available antimalarial drug, there is a desire to discover and develop new antimalarials.

BRIEF SUMMARY OF THE INVENTION

The invention provides methods of treating or preventing malaria comprising administering an effective amount of a compound of formula I to an animal. Methods of inhibiting a plasmodial surface anion channel of a parasite in an animal are also provided.

The invention also provides pharmaceutical compositions comprising a compound represented by formula I in combination with one or more antimalarial compounds, e.g., those represented by formulas II, V, and VI. Use of the pharmaceutical compositions for treating or preventing malaria or for inhibiting a plasmodial surface anion channel in animals including humans are also provided. It is contemplated that the inventive compounds and/or pharmaceutical compositions inhibit a plasmodial surface anion channel and/or treat or prevent malaria by any number of mechanisms, for example, by inhibiting one or members of the parasite clag3 gene family. Embodiments of the inventive compounds have one or more advantages including, but not limited to: high affinity for the ion channel, high specificity for the ion channel, no or low cytoxicity, a chemical structure that is different from existing anti-malarials, and drug-like features.

Also provided by the invention are clag3 amino acid sequences and related nucleic acids, vectors, host cells, populations of cells, antibodies, and pharmaceutical compositions. The invention also provides methods of treating or preventing malaria in an animal and methods of stimulating an immune response against a plasmodial surface anion channel of a parasite in an animal comprising administering to the animal an effective amount of the inventive clag3 amino acid sequences and related nucleic acids, vectors, host cells, populations of cells, antibodies, and pharmaceutical compositions.

BRIEF DESCRIPTION OF THE SEVERAL VIEWS OF THE DRAWING(S)

FIG. 1 is a graph showing sorbitol-induced osmotic lysis kinetics (% lysis) for the allelic exchange clone HB3$^{3rec}$ with indicated concentration of ISPA-28 (04), a compound in accordance with an embodiment of the invention (see Formula A, paragraph below), over time (minutes).

FIG. 2 is a graph showing mean±S.E.M. ISPA-28 dose (μM)-response (normalized P) for HB3$^{3rec}$ (circles). This dose response is intermediate between those of HB3 and Dd2 (top and bottom solid lines, respectively).

DETAILED DESCRIPTION OF THE INVENTION

Figure 1:
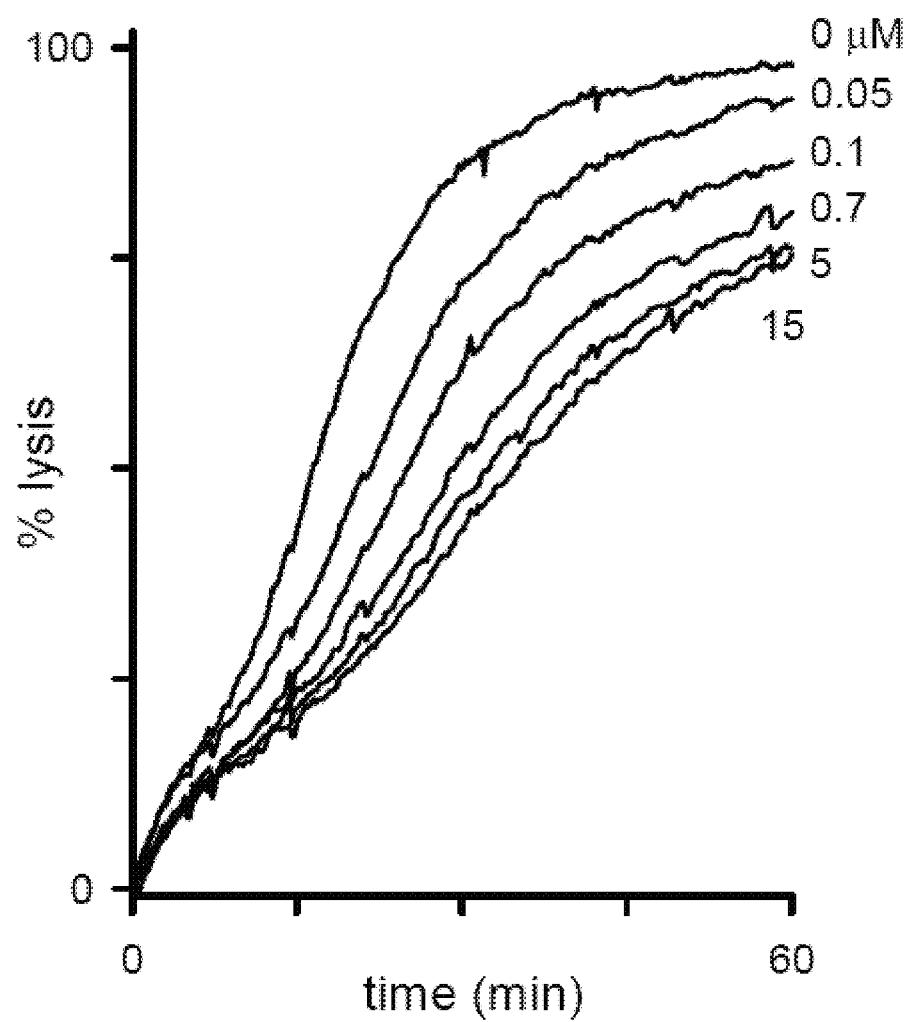

During its approximately 48 h cycle within the human red blood cell (RBC), *P. falciparum* must increase the red blood cell's (RBC's) permeability to a broad range of solutes. Electrophysiological studies identified the plasmodial surface anion channel (PSAC) as the molecular mechanism of these changes. PSAC's functional properties differ from those of known human ion channels. These properties include atypical gating, unique pharmacology, and an unmatched selectivity profile. An unusual property is PSAC's ability to exclude $Na^+$ by more than 100,000-fold relative to $Cl^-$ despite the channel's broad permeability to anions and bulky nutrients. This level of exclusion of a single small solute has not been reported in other broadly selective channels; it is essential for parasite survival because a higher $Na^+$ permeability would produce osmotic lysis of infected RBCs in the high $Na^+$ serum.

PSAC plays a central role in parasite nutrient acquisition. Sugars, amino acids, purines, vitamins, and precursors for phospholipid biosynthesis have markedly increased uptake into infected RBCs via PSAC. Many of these solutes have negligible permeability in uninfected RBCs and must be provided exogenously to sustain in vitro parasite growth. PSAC is conserved on divergent plasmodial species, as determined through studies of erythrocytes infected with rodent, avian, and primate malaria parasites. The channel's gating, voltage dependence, selectivity, and pharmacology are all conserved, suggesting that PSAC is a highly constrained integral membrane protein. Its surface location on the erythrocyte membrane offers conceptual advantages over parasite targets buried inside the infected RBC. PSAC's exposed location on infected RBCs forces direct access to antagonists in serum and excludes resistance via drug extrusion. In contrast, drugs acting within the parasite compartment must cross at least three membranous barriers to reach their target; clinical resistance to chloroquine and mefloquine appear to be linked to extrusion from their sites of action. Nearly all available PSAC antagonists inhibit in vitro parasite growth at concentrations modestly higher than those required for channel inhibition.

PSAC-inhibitor interactions may be determined by members of the clag3 plasmodia gene family. Clag3.1 (also known as RhopH1(3.1) and PFC0120w) and clag3.2 (also known as RhopH1(3.2) and PFC0110w) are members of the clag multigene family conserved in *P. falciparum* and *P. vivax*. Clag3.1 and clag3.2 are located on *P. falciparum* chromosome 3. The clag 3.1 gene sequence is referenced by Genbank Accession Nos. 124504714 and XM_001351064 (SEQ ID NO: 1). SEQ ID NO: 1 sets forth the mRNA sequence of the clag3.1 gene without the untranslated regions. The sequence of the protein product of the clag 3.1 gene (known as cytoadherence linked asexual protein 3.1) is referenced by Genbank Accession Nos. XP_001351100 and CAB10572.2 (SEQ ID NO: 2). The clag 3.2 gene sequence is referenced by Genbank Accession Nos. 124504712 and XM_001351063 (SEQ ID NO: 3). SEQ ID NO: 3 sets forth the mRNA sequence of the clag3.2 gene without the untranslated regions. The sequence of the protein product of the clag 3.2 gene (known as cytoadherence linked asexual protein 3.2) is referenced by Genbank Accession Nos. XP_001351099 and 124504713 (SEQ ID NO: 4). Based on available evidence, clag3.1 and clag3.2 encode the parasite PSAC.

The invention also provides a chimeric clag3.1/clag3.2 gene. SEQ ID NO: 79 sets forth the mRNA sequence of the chimeric clag3.1/clag3.2 gene without the untranslated regions, and SEQ ID NO: 78 sets forth the protein product of the chimeric clag3.1/clag3.2 gene. Amino acid residues 1-1011 of SEQ ID NO: 78 correspond to amino acid residues 1-1011 of the clag3.1 protein SEQ ID NO: 2. Amino acid residues 1012-1417 of SEQ ID NO: 78 correspond to amino acid residues 1014-1416 of the clag3.2 protein SEQ ID NO: 4. Based on available evidence, the chimeric clag3.1/clag3.2 gene encodes a parasite PSAC.

Accordingly, the invention provides, in an embodiment, a method of treating or preventing malaria in an animal comprising administering an effective amount of a compound of formula (I) to the animal, preferably a human:

(I), wherein:

Q is selected from the group consisting of a dioxo heterocyclyl ring fused to an aryl group, a heterocyclic amido group linked to a heterocyclic group, alkyl, a heterocyclic group fused to a heterocyclic amido group, arylamino carbonyl, amino, heterocyclic amido, and heterocyclic amino group, each of which, other than amino, is optionally substituted with one or more substituents selected from the group consisting of halo, hydroxy, mercapto, alkoxy, alkylthio, nitro, cyano, amino, alkyl, aryl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

Y is a bond, S, $SO_2$, or amido;

$R^1$ is divalent group selected from the group consisting of a heterocyclic ring having at least one nitrogen atom, piperidinyl, piperazinyl, aryl, a heterocyclic ring having at least one nitrogen atom linked to an alkylamino group, benzo fused heterocyclyl, heterocyclyl fused to an iminotetrahydropyrimidino group, and heterocyclyl fused to a heterocyclic amido group, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

$R^2$ is selected from the group consisting of arylalkenyl, heterocyclyl carbonylamino, heterocyclyl alkylamino, tetrahydroquinolinyl alkenyl, tetrahydroisoquinolinyl alkyl, indolylalkenyl, dihydroindolylalkenyl, aryl, aryloxyalkyl, arylalkyl, diazolyl, and quinolinylalkenyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

or a pharmaceutically acceptable salt thereof.

Another embodiment of the invention provides a method of inhibiting a plasmodial surface anion channel of a parasite in an animal comprising administering an effective amount of a compound of formula (I) to the animal, preferably a human:

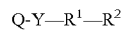
(I), or a pharmaceutically acceptable salt thereof, wherein Q, Y, $R^1$, and $R^2$ are as defined above.

Still another embodiment of the invention provides a compound of formula (I):

Q-Y—$R^1$—$R^2$ (I), or a pharmaceutically acceptable salt thereof, wherein Q, Y, and $R^2$ are as defined above;

for use in treating or preventing malaria in an animal, preferably a human.

Yet another embodiment of the invention provides a compound of formula (I):

Q-Y—$R^1$—$R^2$ (I), or a pharmaceutically acceptable salt thereof, wherein Q, Y, $R^1$, and $R^2$ are as defined above;

for use in inhibiting a plasmodial surface anion channel of a parasite in an animal, preferably a human.

Still another embodiment of the invention provides a use of a compound of formula (I):

Q-Y—$R^1$—$R^2$ (I), or a pharmaceutically acceptable salt thereof, wherein Q, Y, $R^1$, and $R^2$ are as defined above;

in the manufacture of a medicament for treating or preventing malaria in an animal, preferably a human.

Yet another embodiment of the invention provides a use of a compound of formula (I):

Q-Y—$R^1$—$R^2$ (I), or a pharmaceutically acceptable salt thereof, wherein Q, Y, $R^1$, and $R^2$ are as defined above;

in the manufacture of a medicament for inhibiting a plasmodial surface anion channel of a parasite in an animal, preferably a human.

In accordance with an embodiment of the invention, Q in formula I is selected from the group consisting of dioxotetrahydroquinoxalinyl, pyridazinyl heterocyclyl, alkyl, heterocyclyl pyridazinyl, and arylaminocarbonylalkyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

In accordance with an embodiment of the invention, $R^1$ in formula I is selected from the group consisting of piperidinyl, piperazinyl, piperidinylalkylamino, benzothiazolyl, thiozolyl fused to an imino tetrahydropyrimidino group, and thiazolyl fused to a pyridazone, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

In accordance with an embodiment of the invention, $R^2$ in formula I is selected from the group consisting of alkyl arylalkenyl, thiopheneylcarbonylamino, tetrahydro quinolinyl alkenyl, tetrahydro isoquinolinylalkyl, alkoxyaryl, aryl, aryloxyalkyl, and arylalkyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

In accordance with an embodiment of the invention, Y in formula I is $SO_2$. For example, Q in formula I is selected from the group consisting of (point of attachment is represented by a wiggly line here and elsewhere in the application):

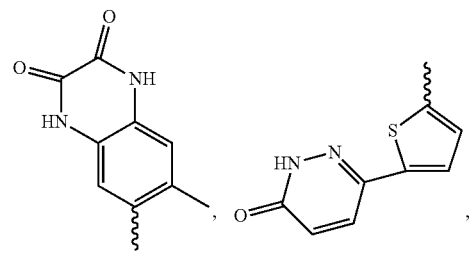

methyl, and isobutyl. In accordance with an embodiment of the invention, $R^1$ in formula I is selected from the group consisting of:

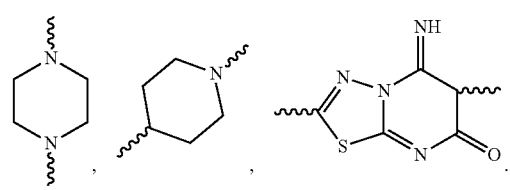

In accordance with an embodiment of the invention, $R^2$ is selected from the group consisting of:

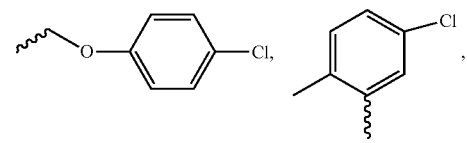

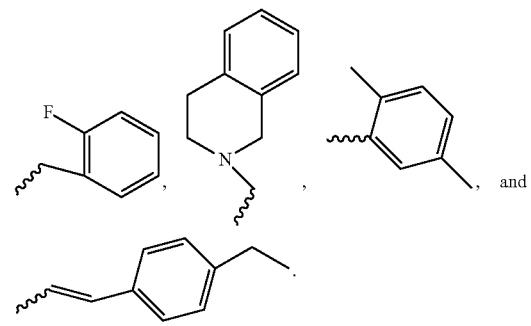

In accordance with any of the embodiments above, the compound of formula I is:
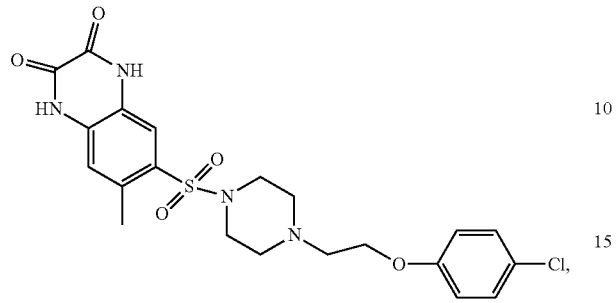
ISG-17
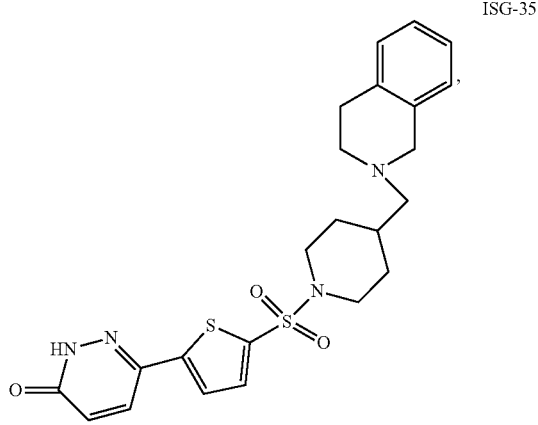
ISG-35
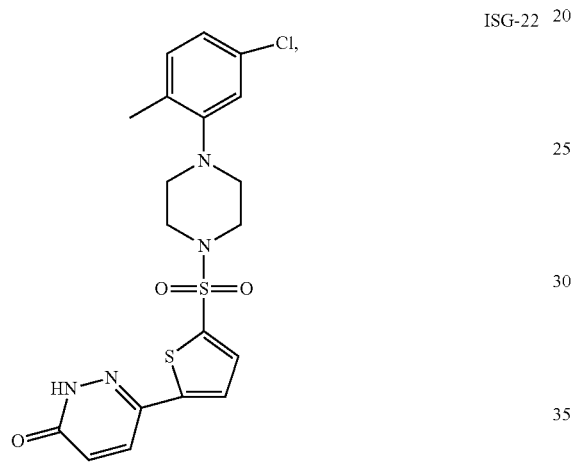
ISG-22
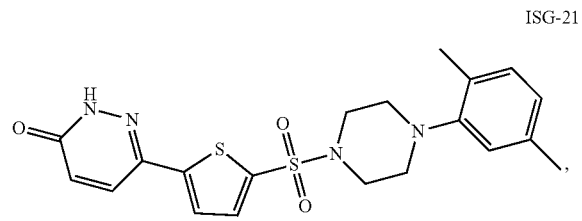
ISG-21
ISG-23
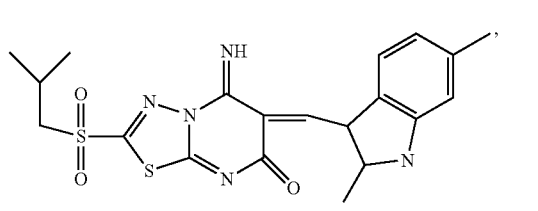
CD-008
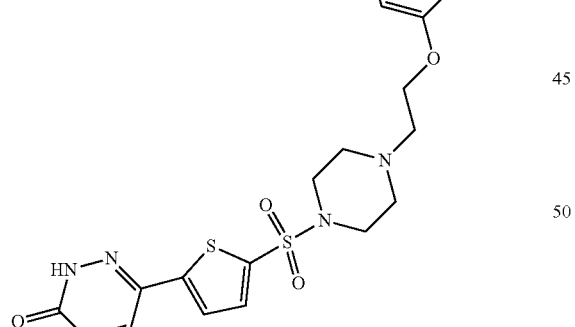
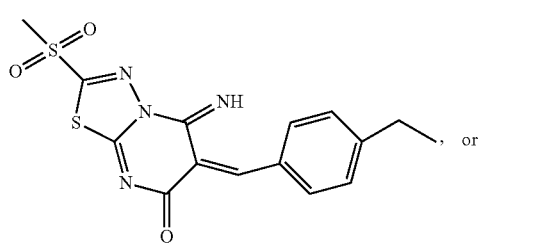
CD-007, or
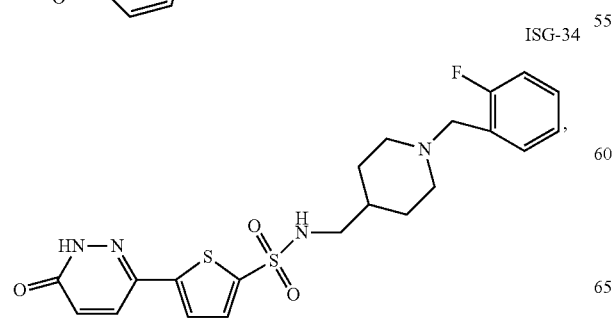
ISG-34
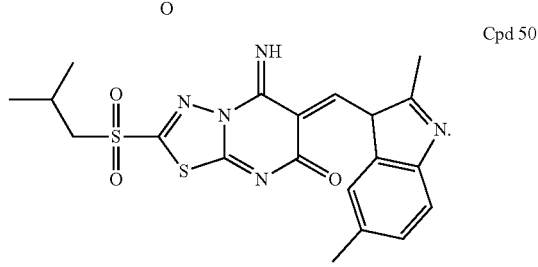
Cpd 50
In accordance with an embodiment of the invention, Y in formula I is S. For example, in accordance with an embodiment of the invention, Q in formula I is selected from the group consisting of:

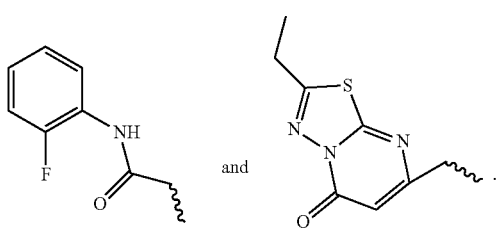

In accordance with an embodiment of the invention, R¹ in formula I is selected from the group consisting of:

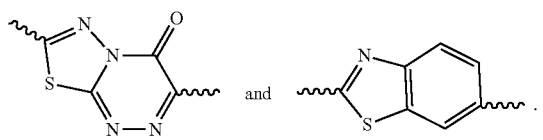

In accordance with an embodiment of the invention, R² in formula I is selected from the group consisting of:

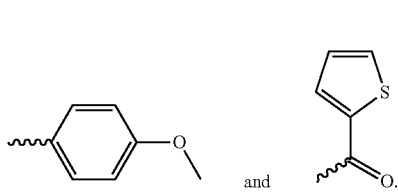

In accordance with an embodiment of the invention, the compound of formula I is:

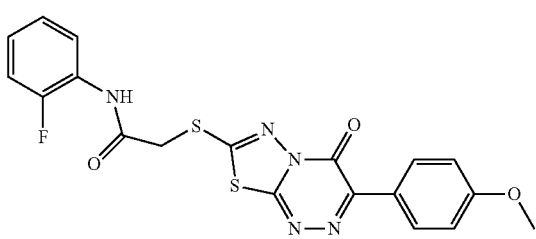

In accordance with an embodiment of the invention, Y of formula I is a bond. For example, in an embodiment of the invention, the compound of formula I is:

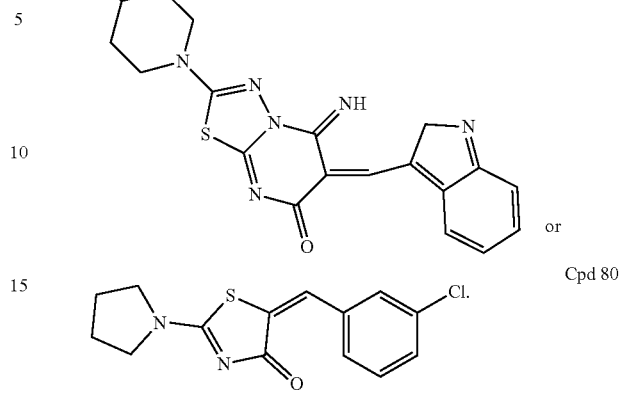

In accordance with an embodiment of the invention, Y of formula (I) is amido. In accordance with an embodiment of the invention, Q is heterocyclic amido, $R_1$ is a heterocyclic ring having at least one nitrogen atom, and $R_2$ is diazolyl. For example, in an embodiment of the invention, the compound of formula I is:

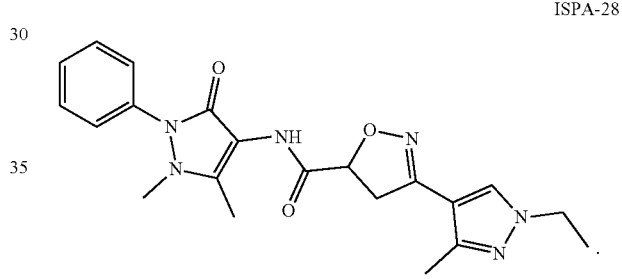

In an embodiment of the invention, the compound inhibits growth of *P. falciparum* Dd2.

Another embodiment of the invention provides a pharmaceutical composition comprising:

i) a compound of formula (I):

$$Q\text{-}Y\text{-}R^1\text{-}R^2 \qquad (I),$$

wherein:

Q is selected from the group consisting of a dioxo heterocyclyl ring fused to an aryl group, a heterocyclic amido group linked to a heterocyclic group, alkyl, a heterocyclic group fused to a heterocyclic amido group, arylamino carbonyl, amino, heteroyclic amido, and heterocyclic amino group, each of which, other than amino, is optionally substituted with one or more substituents selected from the group consisting of halo, hydroxy, mercapto, alkoxy, alkylthio, nitro, cyano, amino, alkyl, aryl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

Y is a bond, S, $SO_2$, or amido;

R¹ is divalent group selected from the group consisting of a heterocyclic ring having at least one nitrogen atom, piperidinyl, piperazinyl, aryl, a heterocyclic ring having at least one nitrogen atom linked to an alkylamino group, benzo fused heterocyclyl, heterocyclyl fused to an iminotetrahydropyrimidino group, and heterocyclyl fused to a heterocyclic amido group, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

R$^2$ is selected from the group consisting of arylalkenyl, heterocyclyl carbonylamino, heterocyclyl alkylamino, tetrahydroquinolinyl alkenyl, tetrahydroisoquinolinyl alkyl, indolylalkenyl, dihydroindolylalkenyl, aryl, aryloxyalkyl, arylalkyl, diazolyl, and quinolinylalkenyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

or a pharmaceutically acceptable salt thereof and ii) at least one other antimalarial compound.

The antimalarial compound may be any suitable antimalarial compound and may act by any mechanism and may, for example, inhibit a PSAC at any site. In an embodiment of the invention, the antimalarial compound is artemisinin, mefloquine, chloroquine, or derivatives thereof.

In an embodiment of the invention, the at least one other antimalarial compound is one or more compounds selected from the group consisting of:

a) a compound of formula II:

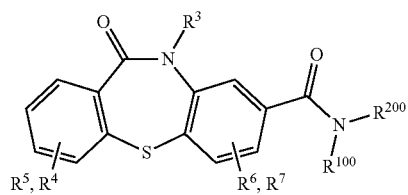

(II)

wherein R$^{100}$ is hydrogen or alkyl and R$^{200}$ is arylalkyl, optionally substituted on the aryl with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl; or R$^{200}$ is a group of formula (III):

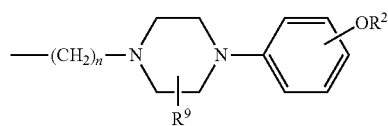

(III)

wherein n=0 to 6;

or R$^{100}$ and R$^{200}$ together with the N to which they are attached form a heterocycle of formula IV:

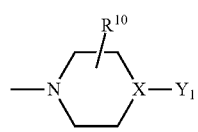

(IV)

wherein X is N or CH; and

Y$_1$ is aryl, alkylaryl, dialkylaryl, arylalkyl, alkoxyaryl, or heterocyclic, optionally substituted with one or more substituents selected from the group consisting of halo, hydroxyl, nitro, cyano, amino, aminoalkyl, alkylamino, alkylcarbonyl, alkoxycarbonyl, aminocarbonyl, and formyl; and R$^3$-R$^{10}$ are hydrogen or alkyl; or a pharmaceutically acceptable salt thereof;

(b) a compound of formula V:

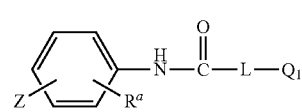

(V)

wherein

Z is a group having one or more 4-7 membered rings, wherein at least one of the rings has at least one heteroatom selected from the group consisting of O, S, and N; and when two or more 4-7 membered rings are present, the rings may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl;

R$^a$ is hydrogen, alkyl, or alkoxy;

L is a bond, alkyl, alkoxy, (CH$_2$)$_r$, or (CH$_2$O)$_s$, wherein r and s are independently 1 to 6;

Q$_1$ is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl; and when L is alkyl or alkoxy, Q$_1$ is absent;

or a pharmaceutically acceptable salt thereof; and (c) a compound of formula VI:

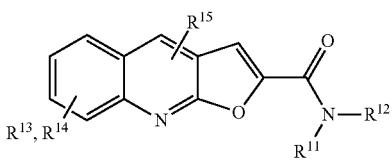

(VI)

wherein R$^{11}$ and R$^{12}$ are independently hydrogen, alkyl, cycloalkyl, or aryl which is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl;

R$^{13}$-R$^{15}$ are independently selected from the group consisting of alkyl, halo, alkoxy, hydroxy, nitro, cyano, amino, alkylamino, aminoalkyl, alkylcarbonyl, alkoxycarbonyl, aminocarbonyl, and formyl;

or a pharmaceutically acceptable salt thereof. In this regard, in an embodiment of the invention, the pharmaceutical composition comprises at least one compound of formula I in combination with one or more compounds disclosed in U.S. Patent Application Publication No. 2011/0144086, which is a United States national stage application of PCT/US09/50637, filed on Jul. 15, 2009, and which published as WO 2010/011537, each of which are incorporated herein by reference.

In accordance with an embodiment of the invention, the pharmaceutical composition comprises a compound of formula I and any one or more of

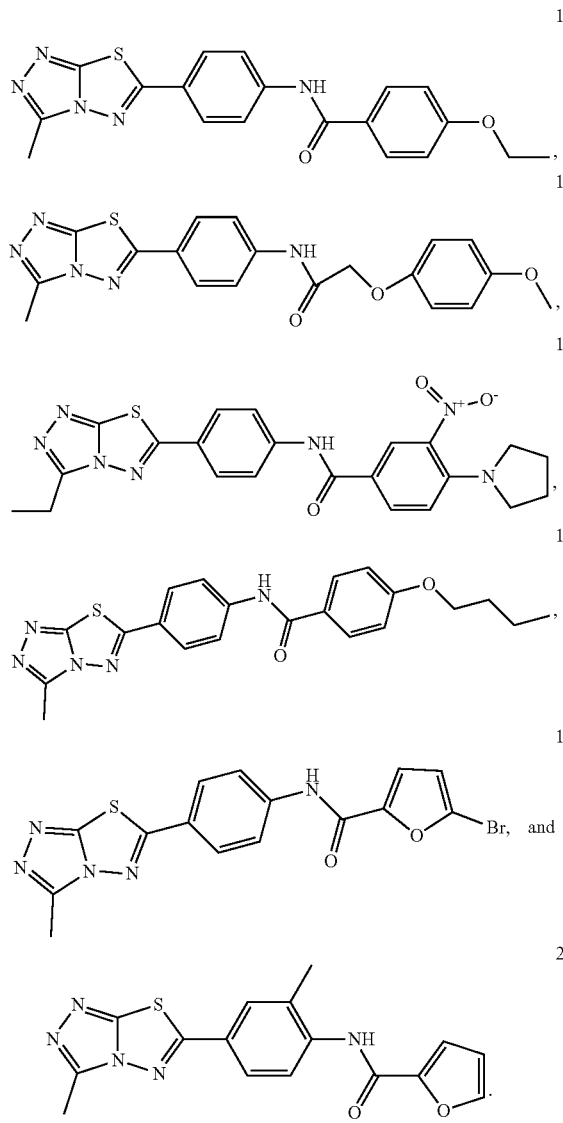

Another embodiment of the invention provides a method of treating or preventing malaria in an animal comprising administering to the animal an effective amount of a compound of formula I and at least one other antimalarial compound. In an embodiment, the at least one other antimalarial compound is one or more compound(s) selected from the group consisting of a compound of formula II, a compound of formula V, and a compound of formula VI.

Still another embodiment of the invention provides a method of inhibiting a plasmodial surface anion channel of a parasite in an animal comprising administering to the animal an effective amount of a compound of formula I and one or more compound(s) selected from the group consisting of a compound of formula II, a compound of formula V, and a compound of formula VI.

Referring now to terminology used generically herein, the term "alkyl" implies a straight or branched alkyl moiety containing from, for example, 1 to 12 carbon atoms, preferably from 1 to 8 carbon atoms, more preferably from 1 to 6 carbon atoms. Examples of such moieties include methyl, ethyl, propyl, isopropyl, n-butyl, sec-butyl, isobutyl, tert-butyl, pentyl, isoamyl, hexyl, octyl, dodecanyl, and the like.

The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2 π electrons, according to Hückel's Rule, wherein n=1, 2, or 3.

The term "heterocyclic" means a cyclic moiety having one or more heteroatoms selected from nitrogen, sulfur, and/or oxygen. Preferably, a heterocyclic is a 5 or 6-membered monocyclic ring and contains one, two, or three heteroatoms selected from nitrogen, oxygen, and/or sulfur. Examples of such heterocyclic rings are pyrrolinyl, pyranyl, piperidyl, tetrahydrofuranyl, tetrahydrothiopheneyl, and morpholinyl.

The term "alkoxy" embraces linear or branched alkyl groups that are attached to a an ether oxygen. The alkyl group is the same as described herein. Examples of such substituents include methoxy, ethoxy, t-butoxy, and the like.

The term "halo" as used herein, means a substituent selected from Group VIIA, such as, for example, fluorine, bromine, chlorine, and iodine.

For the purpose of the present invention, the term "fused" includes a polycyclic compound in which one ring contains one or more atoms preferably one, two, or three atoms in common with one or more other rings.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any subrange or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In accordance with an embodiment of the invention, $R^3$ in formula II is hydrogen. In accordance with the above embodiments, $R^4$—$R^7$ in formula II are hydrogen. In an example, $R^{100}$ in formula II is hydrogen and $R^{200}$ is a group of formula III, wherein n=1 to 6, preferably n=2 to 4.

In accordance with an embodiment of the invention, wherein $R^{100}$ and $R^{200}$ together with the N to which they are attached form a heterocycle of formula IV. For example, X in formula IV is N. In accordance with the invention, in formula IV, $Y_1$ is aryl which is optionally substituted with one or more substituents selected from the group consisting of halo, hydroxyl, nitro, cyano, amino, alkyl, alkoxy, aminoalkyl, alkylamino, alkylcarbonyl, alkoxycarbonyl, aminocarbonyl, and formyl. For example, in formula IV, $Y_1$ is phenyl, which is optionally substituted with one or more substituents selected from the group consisting of halo, hydroxyl, nitro, cyano, amino, alkyl, alkoxy, aminoalkyl, alkylamino, alkylcarbonyl, alkoxycarbonyl, aminocarbonyl, and formyl, specifically, $Y_1$ is phenyl or phenyl substituted with one or more substituents selected from the group consisting of methyl, chloro, fluoro, and methoxy.

In accordance with any of the embodiments above, the compound of formula II is:

1

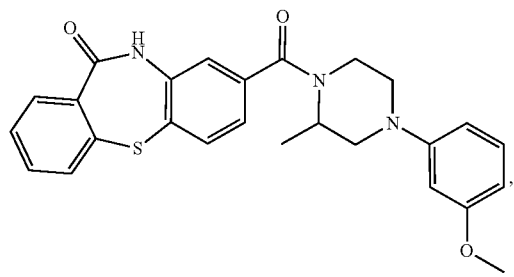

2

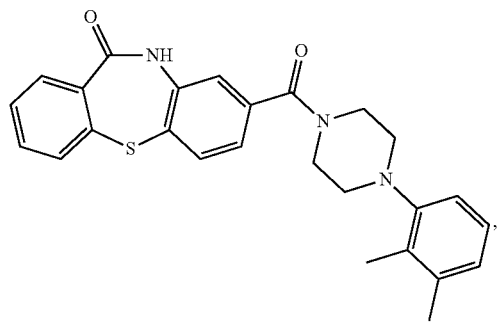

3

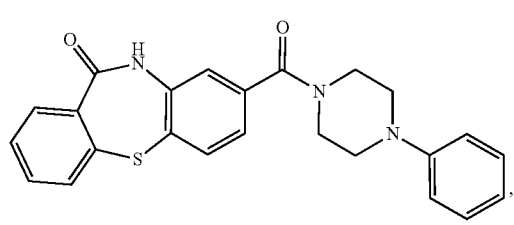

4

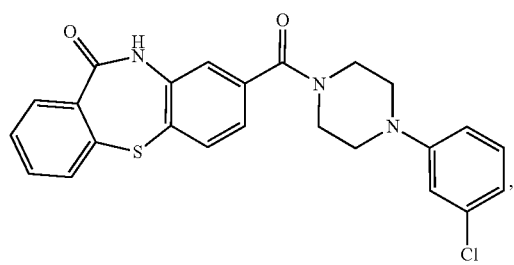

5

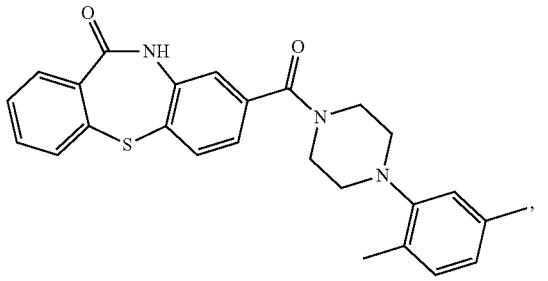

31

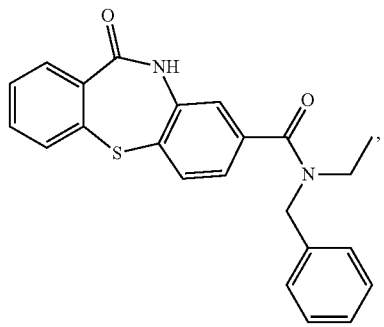

6

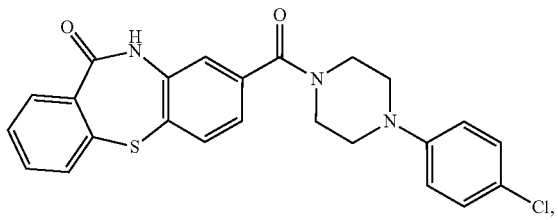

7

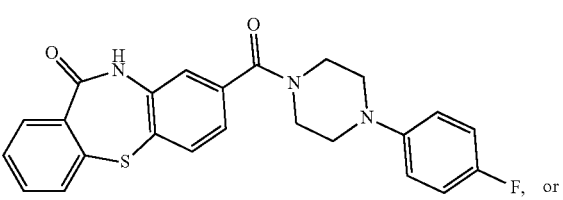

8

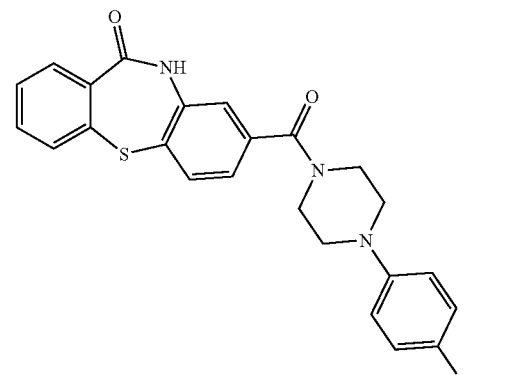

In accordance with another embodiment of the invention, X in formula IV is CH. In a particular embodiment, $Y_1$ is arylalkyl or heterocyclic, which is optionally substituted with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl. Illustratively, $Y_1$ is benzyl or piperidinyl, which is optionally substituted with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl. Examples of specific compounds of formula II are:

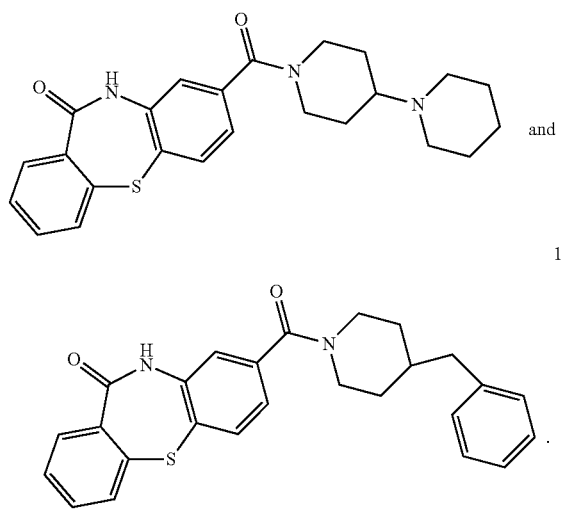

In another embodiment of the invention, $R^{100}$ in formula II is hydrogen and $R^{200}$ is arylalkyl, optionally substituted on the aryl with a substituent selected from the group consisting of halo, hydroxyl, nitro, cyano, amino, alkyl, aminoalkyl, alkylamino, alkylcarbonyl, and formyl. As an example, $R^{200}$ is arylalkyl, e.g., phenylalkyl such as phenyl butyl. A specific example of such a compound of formula II is:

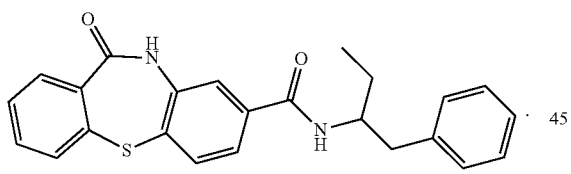

In accordance with an embodiment of the invention, a specific example of a compound of formula III is:

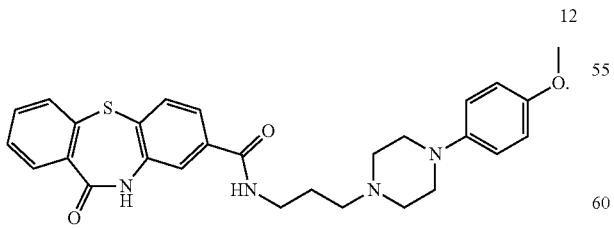

In accordance with another embodiment of the invention, in the compound of formula V, L is a bond or $(CH_2O)_s$, and $Q_1$ is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In accordance with an embodiment, wherein Z is a group having one or more 4-7 membered rings, wherein at least one of the rings has at least one heteroatom selected from the group consisting of O, S, and N; and when two or more 4-7 membered rings are present, they may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In the above embodiment, Z is a group having one or two 4-7 membered rings, wherein at least one of the rings has at least one heteroatom selected from the group consisting of O, S, and N; and when two 4-7 membered rings are present, they may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In a specific embodiment of the formula V, $Q_1$ is an aryl group, optionally substituted with an alkoxy group or $Q_1$ is a heterocyclic group which is saturated or unsaturated. For example, $Q_1$ is aryl such as phenyl or naphthyl.

Examples of compounds of formula IV are:

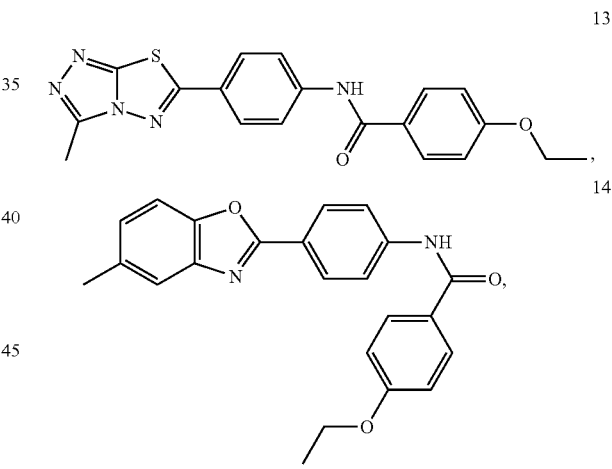

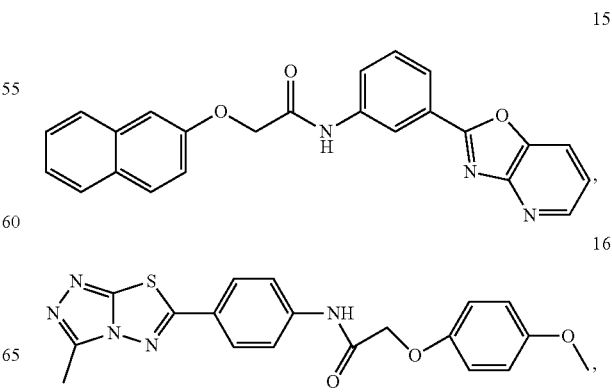

-continued

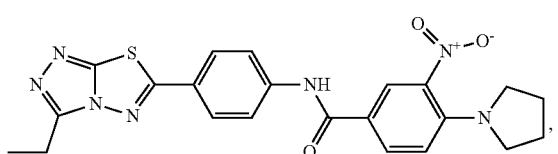

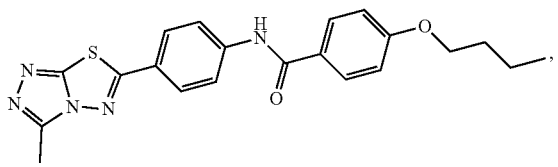

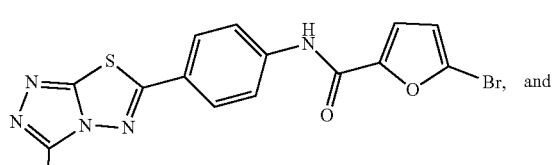

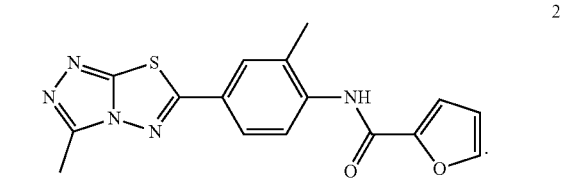

In accordance with an embodiment of the invention, in the compound of formula V, $Q_1$ is a heteroaromatic group, e.g., pyridyl. An example of such a compound is:

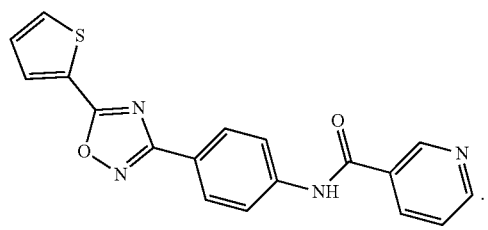

In accordance with another embodiment of the invention, in the compound of formula V, L is an alkyl group and $Q_1$ is absent. Examples of such compounds are:

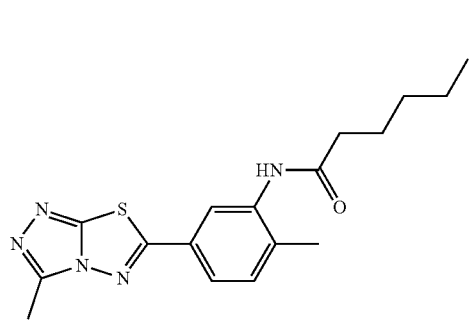
and

-continued

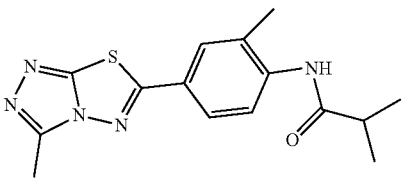

In accordance with another embodiment of the invention, in the compound of formula VI, $R^{13}$ is alkyl or alkoxy and $R^{14}$ and $R^{15}$ are hydrogen. In a particular embodiment, $R^{13}$ is methyl or methoxy.

In the above embodiments of the compound of formula VI, specifically, RH is alkyl and $R^{12}$ is alkyl, cycloalkyl, or aryl, wherein said aryl is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl. In a particular embodiment, $R^{12}$ is alkyl, cycloalkyl, or aryl, wherein said aryl is optionally substituted with one or more alkyl and/or alkoxy substituents.

Examples of compounds of formula VI are:

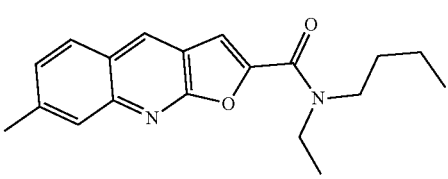

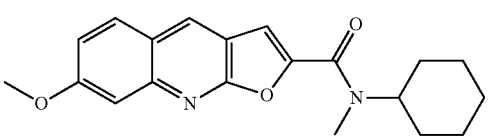

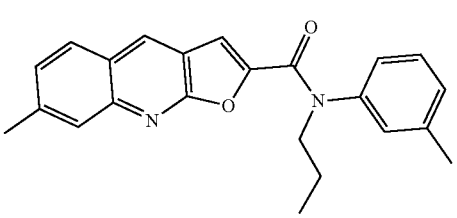
, and

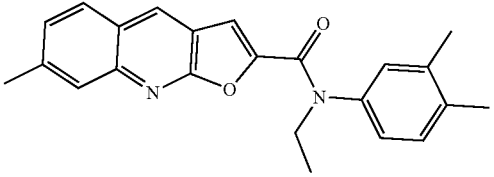

In accordance with an embodiment of the invention, in compound of formula VI, RH is hydrogen and RH is cycloalkyl or aryl, which is optionally substituted with one or more alkyl and/or alkoxy substituents. Exemplary compounds of formula VI are:

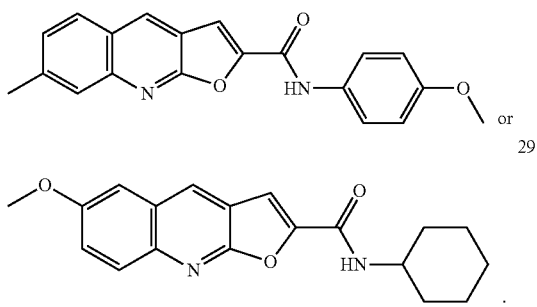

In accordance with the invention, an effective amount of a compound of formula I is administered in combination with any one or more compound(s) of formulas II, V, and VI, for example, a combination of compounds of formulas I and II, compounds of formulas I and V, compounds of formulas I and VI, compounds of formulas I, II and V, compounds of formulas I, II and VI, compounds of formulas I, V and VI, or compounds of formulas I, II, V, and VI, or pharmaceutically acceptable salts thereof, is administered. It is contemplated that such combinations provide synergy—enhanced killing of the parasite, when a combination of two or more compounds are employed. The extent of killing is greater than the sum of the individual killings.

The compounds of the invention can be prepared by suitable methods as would be known to those skilled in the art or obtained from commercial sources such as ChemDiv Inc., San Diego, Calif. or Peakdale Molecular Limited, High Peak, England. See also WO 00/27851 and U.S. Pat. Nos. 6,602,865 and 2,895,956.

Another embodiment of the invention provides a clag3 amino acid sequence comprising, consisting of, or consisting essentially of SEQ ID NO: 62, 64, 66, 72, 74, or 76, with the proviso that the amino acid sequence is not SEQ ID NO: 2, 4, or 78. SEQ ID NOs: 62, 64, 66, 74, and 76 correspond to amino acid residues 1063-1208, 1232-1417, 25-332, 488-907, and 925-1044 of the clag3.1 protein of the 3D7 parasite line. SEQ ID NO: 72 corresponds to amino acid residues 1063-1244 of the clag3.1 protein of the Dd2 parasite line. SEQ ID NOs: 62, 64, 66, 72, 74, and 76 are encoded by nucleotide sequence SEQ ID NOs: 63, 65, 67, 73, 75, and 77, respectively.

In this regard, an embodiment of the invention provides a clag3 amino acid sequence comprising, consisting of, or consisting essentially of SEQ ID NO: 62, 64, 66, 72, 74, or 76, with the proviso that the amino acid sequence is not SEQ ID NO: 2,4, or 78.

Another embodiment of the invention provides a nucleic acid comprising a nucleotide sequence encoding the inventive amino acid sequences, with the proviso that the nucleotide sequence is not SEQ ID NO: 1,3, or 79. For example, the nucleotide sequence comprises, consists, or consists essentially of SEQ ID NO: 63, 65, 67, 73, 75, or 77.

Further embodiments of the invention provide a recombinant expression vector comprising an inventive nucleic acid, an isolated host cell comprising the inventive recombinant expression vector, a population of cells comprising the inventive host cell, and an antibody, or antigen binding portion thereof, which specifically binds to an inventive amino acid sequence. The inventive amino acid sequence, nucleic acid, recombinant expression vector, host cell, population of cells, and/or antibody, or antigen binding portion thereof may be isolated or purified.

Still another embodiment of the invention provides a pharmaceutical composition comprising the inventive amino acid sequence, nucleic acid, recombinant expression vector, host cell, population of cells, and/or antibody, or antigen binding portion thereof, and a pharmaceutically acceptable carrier.

Yet another embodiment of the invention provides a method of treating or preventing malaria in an animal comprising administering to the animal an effective amount of the inventive amino acid sequence, nucleic acid, recombinant expression vector, host cell, population of cells, antibody, or antigen binding portion thereof, and/or pharmaceutical composition.

Yet another embodiment of the invention provides a method of stimulating an immune response against a plasmodial surface anion channel of a parasite in an animal comprising administering to the animal an effective amount of the inventive amino acid sequence, nucleic acid, recombinant expression vector, host cell, population of cells, antibody, or antigen binding portion thereof, and/or pharmaceutical composition. In an embodiment, stimulating an immune response comprises stimulating the production of antibodies that specifically bind to the plasmodial surface anion channel.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable carriers and their formulations are further described in A. R. Gennaro, ed., *Remington: The Science and Practice of Pharmacy* (19th ed.), Mack Publishing Company, Easton, Pa. (1995).

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The amount or dose of a compound of the invention or a salt thereof, or a composition thereof should be sufficient to affect a therapeutic or prophylactic response in the mammal. The appropriate dose will depend upon several factors. For instance, the dose also will be determined by the existence, nature and extent of any adverse side effects that might accompany the administration of a particular compound or salt. Ultimately, the attending physician will decide the dosage of the compound of the present invention with which to treat each individual patient, taking into consideration a variety of factors, such as age, body weight, general health, diet, sex, compound or salt to be administered, route of administration, and the severity of the condition being treated. By way of example and not intending to limit the invention, the dose of the compound(s) described herein can be about 0.1 mg to about 1 g daily, for example, about 5 mg to about 500 mg daily. Further examples of doses include but are not limited to: 0.1 mg, 0.15 mg, 0.2 mg, 0.25 mg, 0.5 mg, 0.6 mg, 0.75 mg, 1 mg, 1.5 mg, 2 mg, 3 mg, 4 mg, 5 mg, 6 mg, 7 mg, 8 mg, 9 mg, 10 mg, 12 mg, 15 mg, 17 mg, 20 mg, 25 mg, 30 mg, 35 mg, 40 mg, 45 mg, 50 mg, 55 mg, 60 mg, 70 mg, 75 mg, 80 mg, 85 mg, 90 mg, 95 mg, 100 mg, 125 mg, 140 mg, 150 mg, 175 mg, 200 mg, 225 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg/kg body weight per day.

The following examples further illustrate the invention but, of course, should not be construed as in any way limiting its scope.

EXAMPLES

Osmotic Lysis Experiments and High-Throughput Inhibitor Screen

Laboratory lines of P. falciparum were cultured by standard methods, enriched at the trophozoite stage using the Percoll-sorbitol method, washed, and resuspended at 25° C. and 0.15% hematocrit in 280 mM sorbitol, 20 mM Na-HEPES, 0.1 mg/ml BSA, pH 7.4 with indicated concentrations of inhibitors; uptake of proline, alanine, and phenyltrimethylammonium chloride (PhTMA-Cl) was similarly measured after iso-osmotic replacement for sorbitol. Osmotic swelling and lysis were continuously tracked by recording transmittance of 700-nm light through the cell suspension (DU640 spectrophotometer with Peltier temperature control, Beckman Coulter). Recordings were normalized to 100% osmotic lysis of infected cells at the transmittance plateau. Inhibitor dose responses were calculated by interpolation of the time required to reach fractional lysis thresholds. Dose responses were fitted to the sum of two Langmuir isotherms:

$$P=a/(1+(x/b))+(1-a)/(1+(x/c)) \quad \text{(Eq. S1)}$$

where P represents the normalized solute permeability in the presence of inhibitor at concentration x, and a, b, and c are constants.

High-throughput screens using this transmittance assay were performed identically with HB3- and Dd2-infected cells at room temperature using a commercial library of 50,000 compounds with >90% purity confirmed by NMR (ChemDiv). Screens were performed in 384-well format with individual wells containing a single compound at 10 μM final concentration. Each microplate had two types of controls. 32 positive control wells received PBS instead of sorbitol; erythrocytes in these wells do not lyse because PSAC has low Na$^+$ permeability. 32 negative control wells received sorbitol with DMSO but no test compound. Readings were taken at multiple timepoints to permit estimation of inhibitor affinity in a high-throughput format. The purity and molecular weight of ISPA-28 were confirmed by mass spectrometry.

The activity of each screening compound was calculated based on readings at the 2 h timepoint according to:

$$\% B = 100 * (A_{cpd} - \bar{A}_{neg})/(\bar{A}_{pos} - \bar{A}_{neg}) \quad \text{(Eq. S2)}$$

where % B is the normalized channel block and $A_{cpd}$ represents the absorbance from a well containing a test compound. $A_{neg}$ and $A_{pos}$ represent the mean absorbances of in-plate negative and positive control wells. % B is a quantitative measure of inhibitor activity.

Inhibitors having significantly differing efficacies against uptake by HB3- and Dd2-infected cells were selected using a weighted difference statistic (WDS), determined from % B values at the 2 h timepoint according to:

$$WDS = |B_{HB3} - \% B_{Dd2}|/(3 * \sigma_{pos}) \quad \text{(Eq. S3)}$$

where $\sigma_{pos}$ is the standard deviation of in-plate positive control wells. Isolate-specific inhibitors have WDS ≥1.0; larger values correspond to greater differences in efficacy against uptake by the two screened parasite lines. Analysis and data mining of the screens were automated using locally developed code (DIAdem 10.2 and DataFinder, National Instruments).

Electrophysiology

Recordings were obtained with quartz patch pipettes (1-3 MS2) and symmetric bath and pipette solutions of 1,000 mM choline chloride, 115 mM NaCl, 10 mM $MgCl_2$, 5 mM $CaCl_2$, 20 mM Na-HEPES, pH 7.4. Where present, ISPA-28 was added to both bath and pipette compartments. Seal resistances were >100 GΩ. Recordings were obtained at imposed membrane potentials of −100 mV, applied as steps from a holding potential of 0 mV, using an Axopatch 200B amplifier (Molecular Devices), low-pass filtered at 5 kHz (8-pole Bessel, Frequency Devices), digitized at 100 kHz, and recorded with Clampex 9.0 software (Molecular Devices).

Single channel open probabilities and gating analyses were determined using locally developed code (DIAdem 8.1, National Instruments). The code for tallying closed channel durations was applied to recordings obtained as voltage steps of 10 s duration to preserve seal integrity. It detects mid-threshold crossings, uses linear interpolation of adjacent sample times, and corrects for a Gaussian filter risetime of 66.4 μs as described in detail previously (Desai et al., *Nanomedicine,* 1: 58-66 (2005)). Durations were tallied into 16 bins/decade, normalized to percent of the total number of events, and displayed on square root plots, where time constants for simple exponentially decaying processes are visible as maxima (Sigworth et al., *Biophys. J.* 52: 1047-54 (1987)).

Quantitative Trait Locus (QTL) Analysis of ISPA-28 Efficacies

A distinct collection of 443 polymorphic microsatellite markers were selected that distinguish the Dd2 and HB3 parental lines (Su et al., *Science,* 286: 1351-53 (1999)). 5 additional single nucleotide polymorphisms within the chromosome 3 locus were identified by DNA sequencing and were used to genotype progeny clones. This genotype data was used to search for genetic loci associated with ISPA-28 efficacy in the genetic cross progeny by performing QTL analysis with R/qtl software (available at http://www.rqtl.org/) as described (Broman et al., *Bioinformatics,* 19: 889-90 (2003)). Because P. falciparum asexual stages are haploid, the analysis was analogous to that for recombinant inbred genetic crosses. Significance thresholds at the P=0.05 level were determined by permutation analysis. A secondary scan to search for additional QTL was carried out by controlling for the primary chromosome 3 locus as described in the R/qtl software package.

piggyBac Transposase-Mediated Complementation

Individual candidate genes and a conserved open reading frame within the mapped locus were evaluated using piggyBac transposase-mediated complementation (Balu et al. *PNAS*, 102: 16391-96 (2005)). Each candidate, along with its presumed endogenous 5' promoter region (1-2 kb upstream of the start ATG) and 3'UTR (0.5 kb downstream from the stop codon), was PCR amplified from HB3 genomic DNA with primers listed below in Table 1, and inserted into the multiple cloning site of the pXL-BacII-DHFR vector; ligation places the insert adjacent to the human dihydrofolate reductase gene (hDHFR), whose product permits selection by the antifolate WR99210. This integration cassette is flanked by two inverted terminal repeats (ITR) that are recognized by piggyBac. Transgene-bearing plasmids were cotransfected into Dd2 with pHTH, a helper plasmid that encodes the transposase but lacks a selectable marker. Expression of the transposase facilitates genomic integration of the transgene and hDHFR.

Dye-terminator sequencing of cDNA was used to confirm transgene expression based on detection of known polymorphic sites as doublet peaks in sequence chromatograms. Briefly, cDNA was generated by reverse transcription from total RNA with SuperScriptIII kit (Invitrogen) according to manufacturer instructions. Specific transcripts were then amplified with gene-specific primers. HB3 alleles noted as not expressed were either not detected by this method or not examined due to the lack of polymorphism between Dd2 and HB3.

TABLE 1

| gene | Forward Primer sequence | Reverse Primer sequence |
| --- | --- | --- |
| PFC0075C | ATACCGTCGAC TTGTCAATTTT TATGTTTGCAT AAACG (SEQ ID NO: 5) | AATTAGGTACCGT ACAAATAAATACA ATATTTTTCATAG CAA (SEQ ID NO: 6) |
| PFC0080C | TATCCGTCGAC TCTATTTACAC TCATGAAGACA GAGGTAA (SEQ ID NO: 7) | AATTAGGTACCCTT CATTGAAAATTTTA CAAGGGTATC (SEQ ID NO: 8) |
| PFC0085C | ATACCGTCGAC TATGAATGATT GTACTACTTTT GTAAGAAT (SEQ ID NO: 9) | AATATGGTACCTACA CATTGACATAGGGTA TCATCATT (SEQ ID NO: 10) |
| PFC0090W | ATACCGTCGAC CCTTTTTACAC GTATATTCGGA CAATC (SEQ ID NO: 11) | AATTAGGTACCGTTA ACACGAACAATTTTG CAGTATG (SEQ ID NO: 12) |
| PFC0095C | ATACCGTCGAC CAAAAAACCGA AATGGCATTTC (SEQ ID NO:13) | AATTAGGTACCATGA AATATGTAATACGTG GGTTAAAAG (SEQ ID NO: 14) |
| PFC0100C | ATACCGTCGAC TTCCATGTTTA AAGTGAAATTA GAAGATAT (SEQ ID NO: 15) | AATTAGGTACCCGAC ATTATGTTATTTCGG CGA (SEQ ID NO: 16) |
| PFC0105W | ATACCGTCGAC CAGTATATATA ATCAAATTGAG CTTAAAAAG (SEQ ID NO: 17) | AATTAGGTACCAGTG TTTTAAGGCAATAAT TATATTGTATT (SEQ ID NO: 18) |
| PFC0110W | TCGACCTCGAG CATAAAATTGT GTGTTTCATTA AAATCAT (SEQ ID NO: 19) | ACGTAGGGCCCATGT ATAAATGAAAAATGA ATGTGACTCTT (SEQ ID NO: 20) |
| PFC0115C | ATTCAGTCGAC AAGAAAAAGGT AATATTTTAGT ACACTCAA (SEQ ID NO: 21) | TATTCGGTACCTTTG TAATATACCTTTATG CGTTGACA (SEQ ID NO: 22) |
| PFC0120W | ATGCAGTCGAC ATGCACTCATT AATAATTTTAA ACCGT (SEQ ID NO: 23) | TCGATGGGCCCCTTT TCAATTAATTTTATA TTCTTTTGTTC (SEQ ID NO: 24) |
| PFC0125W | ATACCGTCGAC CCTGACGATGA ATTAATGATAT CACG (SEQ ID NO: 25) | TATAAGGTACCCAGG TTAATATAGCCAAAA TAAATTGAAA (SEQ ID NO: 26) |
| PFC0126C | ATAGAGTCGAC GGATATTAGCT GATAAAGCAGC AGC (SEQ ID NO: 27) | GATTTGGTACCTTTG TTTTCATGTCCCATC ATAATTC (SEQ ID NO: 28) |
| PFC0130C | ATACCGTCGAC TATTCTACTTA AAGATGAATAG CACATATG (SEQ ID NO: 29) | ACATTGGGCCCTTCC CCTCACATATCAATC ATAAAT (SEQ ID NO: 30) |
| ORF 147k | ATACAGTCGAC GCATCCTATTC CCATCCTTTCC T (SEQ ID NO: 31) | ACTGAGGGCCCGACA AGAAGCATTACAGAG AGCAA (SEQ ID NO: 32) |
| PFC0135c | ATACCGTCGAC ATTTTGCCCAA GAATATAAAAT AATAAGAT (SEQ ID NO: 33) | AATTAGGTACCCAGA GAAAGAAAAATGTCA ATATAAATAAA (SEQ ID NO: 34) |

Allelic Exchange of Clag3

Allelic exchange was achieved by single-site homologous recombination of a Dd2 clag3.1 transgene into the HB3 genomic clag3.2. A DNA fragment containing the 3'portion (3219 bp) of clag3.1 and its 3' UTR (441 bp) was amplified from Dd2 with primers (SEQ ID NO: 35)
5'-cataagcggccgcGCCATTCAGACCAAGCAAGG-3'
and (SEQ ID NO: 36)
5'-ttaaactgcagCTTTTCAATTAATTTTATATTCTTTTGTTC-3'.

The amplicon was cloned into the pHD22Y plasmid (Fidock et al., *PNAS*, 94: 10931-36 (1997)) between NotI and PstI sites. The final transfection plasmid (pHD22Y-120w-flag-PG1) was constructed by addition of DNA sequence encoding tetra-cysteines and the FLAG epitope tag (FLNCCPCC-MEPGSDYKDDDDK) (SEQ ID NO: 37) in frame before the gene's stop codon by standard site-directed mutagenesis. Homologous recombination into HB3 was detected by PCR five months after transfection. Recombinant parasites were enriched by sorbitol treatment with ISPA-28 and subjected to limiting dilution to yield the limiting dilution clone HB3$^{3rec}$.

Primers used for PCR verification of homologous recombination into the HB3 genome included those in Table 2:

TABLE 2

| primer | sequence |
|---|---|
| p1 | GTGGAATTGTGAGCGGATAACA (SEQ ID NO: 38) |
| p2 | TCATCGTCCTTATAGTCGGATCC (SEQ ID NO: 39) |
| P3 | ATGTTTTGTAATTTATGGGATAGCGA (SEQ ID NO: 40) |
| p4 | GTTGAGTACGCACTAATATGTCAATTTG (SEQ ID NO: 41) |
| P5 | AACCATAACATTATCATATATGTTAATTACAC (SEQ ID NO: 42) |

Southern Blot Hybridization

Genomic DNA was extracted using Wizard Genomic DNA extraction kit (Promega), digested with indicated restriction enzymes, resolved on a 0.7% agarose gel at 55 V for 18 hrs, and blotted onto positively charged Nylon membrane (Roche). A DNA probe complementary to hdhfr was prepared using primers (SEQ ID NO: 43)
(5'-ATTTCCAGAGAATGACCACAAC-3'
and (SEQ ID NO: 44)
5'-TTAAGATGGCCTGGGTGATTC-3')

and labeled with digoxigenin-dUTP. After prehybridization with DIG-Easy Hyb (Roche), the labeled probe was added and hybridized overnight at 39° C. The blot was washed with 0.1×SSC/0.5% SDS at 53° C., and blocked. Probe binding was then detected with anti-digoxigenin-AP Fab fragments at a dilution of 1:10,000 and CDP-Star substrate (Roche).

Quantification of Gene Expression by Real-Time PCR

Two-step real-time PCR was used to quantify expression of clag genes. Primers specific for each of the 5 clag genes were designed based on polymorphisms identified through DNA sequencing. Genomic DNA PCR using possible permutations of forward and reverse primers produced amplicons with only matched primer pairs, confirming specificity. Primers used included those in Table 3:

TABLE 3

| gene (parasite line) | Forward primer sequence | Reverse primer sequence |
|---|---|---|
| clag2 (all) | CTCTTACTACTTAT TATCTATCTCTCA (SEQ ID NO: 45) | CCAGGCGTAG GTCCTTTAC (SEQ ID NO: 46) |
| clag3.1 (Dd2, 7C12, 7C20, CH361) | ACCCATAACTACAT ATTTTCTAGTAATG (SEQ ID NO: 47) | GACAAGTTCCAGAA GCATCCT (SEQ ID NO: 48) |
| clag3.2 (HB3, HB3$^{3rec}$) | ACCCATAACTACAT ATTTTCTAGTAATG (SEQ ID NO: 49) | AGATTTAGTTACACT TGAAGAATTAGTATT (SEQ ID NO: 50) |
| clag3.2 (Dd2, 7C12,7C20, CH361) | ACCCATAACTACAT ATTTTCTAGTAATG (SEQ ID NO: 51) | GATTTATAACTAGG AGCACTACATTTA (SEQ ID NO: 52) |
| clag3.2 (HB3) | ACCCATAACTACAT ATTTTCTAGTAATG (SEQ ID NO: 53) | TTATAACCATTAGG AGCACTACTTTC (SEQ ID NO: 54) |
| chimeric clag3recom transgene (HB3$^{3rec}$) | ACCCATAACTACAT ATTTTCTAGTAATG (SEQ ID NO: 55) | GACAAGTTCCAGAA GCATCCT (SEQ ID NO: 56) |
| clag8 (all) | GTTACTACAACATT CCTGATTCAG (SEQ ID NO: 57) | AATGAAAATATAAA AATGCTGGGGGAT (SEQ ID NO: 58) |
| clag9 (Dd2, 7C12, 7C20, CH361) | TACCATTAGTGTTT TATACACTTAAGG (SEQ ID NO: 59) | CCAAAATATGGCCA AGTACTTGC (SEQ ID NO: 60) |

Total RNA was harvested from synchronous schizont-stage cultures with Trizol reagent (Invitrogen) following the manufacturer's protocol. Residual genomic DNA contaminant was removed by TURBO-DNA-free kit (Ambion). Reverse transcription was performed using SuperScriptIII kit (Invitrogen) with oligo-dT as primer. Negative control reactions that omitted reverse transcriptase were used to exclude samples contaminated with genomic DNA. Real-time PCR was performed with QuantiTect SyBr Green PCR kit (Qiagen) and the above clag gene-specific primer pairs. Amplification kinetics were followed in the iCycler iQ multicolor real-time PCR system (Bio-Rad). Serial dilution of parasite genomic DNA was used to construct the standard curve for each primer pair. rhopH2, rhopH3, and PF7_0073 were used as loading controls. The presented data are normalized to the total clag3 transcript abundance.

In Vitro Selections of Parasites with Altered ISPA Efficacy

PSAC-mediated osmotic lysis of infected cells in unbuffered 280 mM sorbitol solution containing ISPA compounds was used to select for parasites with altered inhibitor efficacy. This strategy is based on rescue of parasites whose channels are blocked by addition of ISPA; it is analogous to the use of sorbitol in synchronization of parasite culture (Lambros et al., *J. Parasitol.*, 65:418-20 (1979)). Optimal selection conditions were determined from lysis kinetics and dose responses. Synchronizations were performed on consecutive days using 30 min incubations of cultures at room temperature with 5 µM ISPA-28 or 4 µM ISPA-43. The marked difference in ISPA-28 affinity between channels associated with the two clag3 genes yielded rapid selection, typically within 4-6 synchronizations. Additional synchronizations were required in reverse selections using ISPA-43, consistent with a relatively modest difference in affinity.

Polyclonal Antibody Production

DNA sequence encoding the C-terminal 141 amino acids of the Dd2 clag3.1 product was cloned into pET-15b vector (Novagen) for over-expression in *E. coli*. Standard site-directed mutagenesis was used to introduce a C-terminal FLAG epitope tag yielding the final plasmid (pet15b-120w-4B) which encodes NH2—

(SEQ ID NO: 61)
MGSS<u>HHHHHH</u>SSGGT*KKYGYLGEVVIARLS*

*PKDKPVINYVHETNEDIMSNLRRYDMENAF*

*KNICAISTYVDDFAFFDDCGKNEQFLNERC*

*DYCPVIEEVEETQLFTTTGDKNTNKTTEIK*

*KQTSTYIDTEICIVINEADSADSDDEKDSD*

*TPDDELMISRFH*<u>DYKDDDDK</u>-CO₂H 61) (clag3.1 product italicized; hexa-histidine and FLAG tags underlined). Recombinant protein was produced in BL21 CodonPlus (DE3) RIL cell line (Agilent Technologies) after transformation with pET-15b-120w-4B and induction with 0.5 mM IPTG for 3 hours. The recombinant protein was harvested by sonication in the presence of protease inhibitors, bound to Ni-NTA Superflow beads (Qiagen), eluted with imidazole under optimized conditions, and dialyzed. Purity and size were confirmed on coomassie-stained SDS-PAGE gels prior to submission for standard mouse immunizations by Precision Antibody (Columbia, Md.), an OLAW certified facility. Antibody titers were >1:100,000 by ELISA.

Protease Susceptibility Studies

Percoll-enriched synchronous trophozoite-infected cells were washed and treated with 1-2 mg/mL pronase E from *Streptomyces griseus* (Sigma Aldrich) at 5% hematocrit in PBS supplemented with 0.6 mM $CaCl_2$) and 1 mM $MgCl_2$ for 1 h at 37° C. Reactions were terminated by addition of 20 volumes of ice cold PBS with protease inhibitors (1 mM PMSF, 2 µg/mL pepstatin, and 2 µg/mL leupeptin) and exhaustive washing. Effectiveness of the protease treatment and the block by protease inhibitors was evaluated by examining PSAC activity with sorbitol uptake measurements. Protease accessibility to erythrocyte cytosol was examined by measuring hemoglobin band intensity in coomassie-stained SDS-PAGE gels of total cell lysate. Band intensity was quantified with ImageJ software (http://rsbweb.nih.gov/) and revealed no detectable hemoglobin degradation (mean of 99±2% relative to untreated controls, n=7 separate trials).

Membrane Fractionation

Infected cells, with or without prior protease treatment, were hemolysed in 40 volumes of lysis buffer (7.5 mM $Na_2HPO_4$, 1 mM EDTA, pH 7.5) with protease inhibitors and ultracentrifuged (70,000×g, 4° C., 1 h). The supernatant was collected as the 'soluble' fraction before resuspending the pellet in 100 mM $Na_2CO_3$, pH 11 at 4° C. for 30 min before centrifugation (70,000×g). The "carbonate extract" supernatant was neutralized with 1/10 volume 1 M HCl. The final pellet was washed with lysis buffer before solubilization as the "membrane" fraction in 2% SDS.

Immunofluorescence Confocal Microscopy

Synchronous parasite cultures were washed and used to make thin smears on glass slides. The cells were air dried prior to fixation in 100% methanol (ice-cold for merozoites and RT for trophozoites) for 5 min. After incubation in 10% Goat Serum Blocking Solution (Invitrogen) with 0.1% Triton X-100, primary antibody against the clag3 recombinant protein and secondary antibody (Alexa Fluor 488 goat anti-mouse IgG, Invitrogen) were applied in the same buffer at 1:50 and 1:500 dilution, respectively with thorough washing between antibodies. Nuclei were stained with Hoechst 33342 before mounting in Fluoromount-G (SouthernBiotech). Dual color fluorescence images were taken on a Leica SP2 confocal microscope under a 100× oil immersion objective with serial 405 nm and 488 nm excitations. Images were processed in Imaris 6.0 (Bitplane AG) and uniformly deconvolved using Huygens Essential 3.1 (Scientific Volume Imaging BV).

Immunoblots

Protein samples were denatured and reduced in NuPAGE® LDS Sample Buffer (Invitrogen) with 100 mM DTT and run on NuPAGE® Novex 4-12% Bis-Tris gels in MES Buffer (Invitrogen), and transferred to nitrocellulose membrane. After blocking (3% fat-free milk in 150 mM NaCl, 20 mM TrisHCl, pH 7.4 with 0.1% Tween20), anti-recombinant clag3 product or anti-FLAG (Cell Signalling Technology), was applied at 1:3000 dilution in blocking buffer. After washing, binding was detected with HRP-conjugated secondary antibodies (Pierce) at 1:3000 dilution and chemiluminescent substrate (Immobilon, Millipore or SuperSignal West Pico, Pierce).

Computational Analyses

Phylogenetic analysis of clag products and the more distantly related RONs was conducted using an approximately-maximum-likelihood method implemented in the FastTree 2.1 program under default parameters (Price et al., *Mol. Biol. Evol.*, 26: 1641-50 (2009)). Transmembrane domains were predicted using the TMHMM and Phobius programs (Krogh et al., *J. Mol. Biol.*, 305: 657-80 (2001); Kall et al., *Bioinformatics*, 21 Suppl. 1: i251-57 (2005)). Improved confidence in transmembrane domain prediction was achieved by inputting multiple alignments of group 2 clag products from several plasmodial species in the Poly-Phobius mode.

Example 1

This example demonstrates the activity of compounds according to formulas (1a) and (2a) below against PSAC. This example also demonstrates the in vitro growth inhibitory activity of compounds (1a) and (2a) in nutrient-rich RPMI and PSAC-limiting medium (PLM). The compounds of formulas (1a) and (2a) are in accordance with an embodiment of the invention.

The concentration of a chemical inhibitor required to produce 50% block of PSAC-mediated solute uptake, $K_{0.5}$ for PSAC block (Table 4), was measured as described previously (*Biophysical J.* 84:116-23, 2003). The chemical inhibitors included:

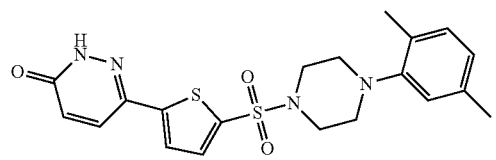

ISG-21 (1a)

and

-continued

ISG-28 (2a)

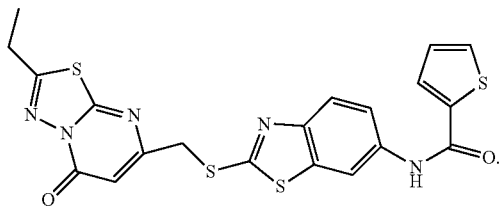

Briefly, *P. falciparum* trophozoites were obtained by in vitro culture in human erythrocytes, enriched by density gradient centrifugation, and used in a continuous light-scattering osmotic lysis assay in sorbitol lysis solution (in mM: 280 sorbitol, 20 Na-HEPES, 0.1 mg/ml BSA, pH 7.4). In this assay, increases in transmittance (% T, measured at 700 nm) correlated directly to lysis of infected RBCs and were plotted in arbitrary units. Uninfected RBCs lacked PSAC activity and had undetectably low sorbitol permeability. Uptake of other nutrient solutes and patch-clamp methods confirmed that this transmittance assay provides a quantitative measure of PSAC inhibition by compounds (1a) and (2a). The PSAC inhibitors of compounds (1a) and (2a) represent a novel strategy for intervention against malaria parasites because currently approved antimalarial drugs (artemisinin, mefloquine, and chloroquine) did not inhibit PSAC activity (Table 4).

In vitro parasite killing by PSAC inhibitors was quantified using a SYBR Green I-based fluorescence assay for parasite nucleic acid in 96-well format. Parasite cultures were synchronized by incubation in 5% D-sorbitol before seeding at 1% parasitemia and 2% hematocrit in standard media for parasite cultivation (RPMI 1640 supplemented with 25 mM HEPES, 50 mg/L hypoxanthine, and 10% regular serum) or in PSAC-limiting medium (PLM, a novel medium based on the RPMI 1640 formulation but with reduced concentrations of isoleucine, glutamine, and hypoxanthine, three nutrients whose uptake by infected cells is primarily via PSAC). While RPMI 1640 contained supraphysiological concentrations of these nutrients, the values in PLM were closer to those measured in plasma from healthy human donors.

Cultures were maintained for 3 days at 37° C. in 5% O2, 5% $CO_2$ without media change. After this incubation, Sybr Green I was added in 20 mM Tris, 10 mM EDTA, 0.016% saponin, 1.6% triton X100. Subsequent fluorescence measurements (excitation/emission at 485/528 nm) permitted quantification of parasite growth because the fluorescence of Sybr Green 1 was a measure of parasite nucleic acid content. Table 4 shows the concentration of each PSAC inhibitor (compounds of formulas (1a) or (2a)) or control antimalarial drug (artemisinin, mefloquine, or chloroquine) required to produce a 50% reduction in parasite survival in RPMI 1640 (RPMI $IC_{50}$) or PLM (PLM $IC_{50}$). Improved killing by PSAC inhibitors (compounds of formulas (1a) and (2a)) upon testing in PLM indicated that the PSAC inhibitors may have a novel mechanism of parasite killing. These data supported a role of PSAC in parasite nutrient acquisition because nutrient limitation improved PSAC inhibitor efficacy, but did not significantly alter killing by artemisinin, mefloquine, or chloroquine (see Ratio of $IC_{50}$ (RPMI/PLM)).

TABLE 4

| Structure | MW | clogP | $K_{0.5}$ for PSAC block, nM | RPMI $IC_{50}$, µM | PLM $IC_{50}$, µM | Ratio (RPMI/PLM) |
|---|---|---|---|---|---|---|
| Compound of formula (1a) | 431 | 3.5 | 3 | 1.5 | 0.0023 | 800 |
| Compound of formula (2a) | 486 | 5.3 | 10 | >30 | 0.3 | >100 |
| Artemisinin | 282 | 2.7 | inactive | 0.018 | 0.026 | 0.66 |
| Mefloquine | 378 | 3.7 | inactive | 0.022 | 0.033 | 0.66 |
| Chloroquine | 319 | 5.1 | inactive | 0.22 | 0.34 | 0.67 |

Example 2

This example demonstrates the identification of isolate-specific inhibitors, which effectively inhibit PSAC activity associated with a specific parasite line. This example also demonstrates that an inhibitor in accordance with the invention interacts directly with PSAC.

A search for small molecule inhibitors with differing efficacies against channels induced by divergent parasite lines was performed. Such inhibitors presumably bind to one or more variable sites on the channel, which may result either from polymorphisms in a parasite channel gene or from differing activation of human channels. To find these inhibitors, a transmittance-based assay that tracks osmotic lysis of infected cells in sorbitol, a sugar alcohol with increased permeability after infection was used (Wagner et al., *Biophys. J.*, 84: 116-23 (2003)). This assay had been adapted to 384-well format and used to find high affinity PSAC inhibitors (Pillai et al., *Mol. Pharmacol.*, 77: 724-33 (2010)). Here, this format was used to screen a library of compounds against erythrocytes infected with the HB3 and Dd2 *P. falciparum* lines. To maximize detection of hits, a low stringency was chosen in the screens by using library compounds at a high concentration (10 µM) and by reading each microplate at multiple timepoints (Pillai et al., *Mol. Pharmacol.*, 77: 724-33 (2010)). 8% of compounds met or exceeded the threshold of 50% normalized block at 2 h [% $B=100*(A_{cpd}-\overline{A}_{neg})/(\overline{A}_{pos}-\overline{A}_{neg})$], consistent with a low screening stringency. A weighted difference statistic (WDS) was defined that normalized measured differences in efficacy against HB3 and Dd2 channels to the standard deviation of positive control wells in each microplate [WDS=|% $B_{HB3}$-% $B_{Dd2}$|/(3*$\sigma_{pos}$)]. 86% of all compounds produced indistinguishable effects on the two parasite lines (WDS ≤1.0). Thus, most inhibitor binding sites were conserved.

Nevertheless, a small number of compounds produced significantly differing activities in the two screens. One such inhibitor, named ISPA-28 (for isolate-specific PSAC antagonist based on studies described below, Formula A below), was reproducibly more effective at inhibiting sorbitol uptake by Dd2- than HB3-infected cells. Secondary studies with ISPA-28 revealed an ~800-fold difference in half-maximal affinities ($K_{0.5}$ values of 56±5 nM vs. 43±2 µM for Dd2 and HB3, respectively; $P<10^{-10}$).

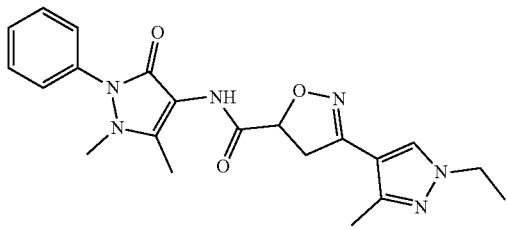

ISPA-28 (Formula A)

ISPA-28 effects on uptake of the amino acids alanine and proline as well as the organic cation phenyl-trimethylammonium (PhTMA), solutes with known increases in permeability after infection (Ginsburg et al., *Mol. Biochem. Parasitol.* 14: 313-22 (1985); Bokhari et al., *J. Membr. Biol.* 226: 27-34 (2008)), were also examined. Each solute's permeability was inhibited with dose responses matching those for sorbitol. Without being bound by a particular theory or mechanism, it is believed that these data provide evidence for a single shared transport mechanism used by these diverse solutes.

22 different laboratory parasite lines were next tested and significant transport inhibition was found with only Dd2 and W2. Because Dd2 was generated by prolonged drug selections starting with W2 (Wellems et al., *Nature,* 345: 253-55 (1990)), their channels' distinctive ISPA-28 affinities suggested a stable heritable element in the parasite genome.

To explore the mechanism of ISPA-28 block, patch-clamp of infected erythrocytes was performed. Using the whole-cell configuration, similar currents on HB3- and Dd2-infected cells in experiments without known inhibitors were observed. These currents exhibited inward rectification. Previous studies determined that they were carried primarily by anions with a permeability rank order of $SCN^->I^->Br^->Cl^-$ (Desai et al., *Nature,* 406: 1001-05 (2000)). 10 μM ISPA-28 reduced these currents, but had a significantly greater effect on Dd2-infected cells. In the cell-attached configuration with 1.1 M $Cl^-$ as the charge carrier, ion channel activity characteristic of PSAC was detected on both lines (~20 pS slope conductance with fast flickering gating, (Alkhalil et al., *Blood,* 104: 4279-86 (2004)); without inhibitor, channels from the two lines were indistinguishable. However, recordings with 10 μM ISPA-28 revealed a marked difference as Dd2 channels were near-fully inhibited whereas HB3 channels were largely unaffected. Thus, this compound's effects on single PSAC recordings parallel those on uptake of sorbitol and other organic solutes.

Closed durations from extended recordings were analyzed and it was determined that ISPA-28 imposed a distinct population of long block events, but only in recordings on Dd2-infected cells. At the same time, intrinsic channel closings, which occur in the absence of inhibitor, were conserved on both parasites and were not affected by ISPA-28.

Example 3

This example demonstrates the inheritance of ISPA-28 efficacy in a Dd2×HB3 genetic cross and that piggyback-mediated complementations implicate clag 3.1 and clag 3.2 in PSAC activity.

ISPA-28 efficacy against PSAC activity on red blood cells infected with recombinant progeny clones from the Dd2× HB3 genetic cross (Wellems et al., *Nature,* 345: 253-255 (1990)) was next examined. For each clone, sorbitol uptake was examined in the absence and presence of 7 μM ISPA-28, a concentration that optimally distinguishes the parental channel phenotypes, and quantified inhibition [% B=100* $(A_{cpd}-\bar{A}_{neg})/(\bar{A}_{pos}-\bar{A}_{neg})$]. Although a few of the 34 independent progeny clones exhibited intermediate channel inhibition, most resembled one or the other parent. Quantitative trait locus (QTL) analysis was used to search for associations between ISPA-28 efficacy and inheritance of available microsatellite markers. A primary scan identified a single significant peak having a logarithm of odds (LOD) score of 12.6 at the proximal end of chromosome 3. A secondary scan for residual effects did not find additional peaks reaching statistical significance.

The mapped locus contained 42 predicted genes. Although none had homology to classical ion channels from other organisms, many were conserved in other plasmodia, as expected for the responsible gene(s) from conservation of PSAC activity in malaria parasites (Lisk et al., *Eukaryot. Cell,* 4: 2153-59 (2005)). The mapped region was enriched in genes encoding proteins destined for export to host cytosol ($P<10^{-4}$ by simulation), as typical of apicomplexan subtelomeric regions. Some of the encoded proteins had one or more predicted transmembrane domains as usually involved in channel pore formation, but this criterion may miss some transport proteins. The PEXEL motif, which directs parasite proteins to the host cell (Marti et al., *Science,* 306: 1930-33 (2004)), was present in some genes, but this module is not universally required for export (Spielman et al., *Trends Parasitol.* 26: 6-10 (2010)). Thus, computational analyses suggested several candidates, but could not specifically implicate any as ion channel components.

A DNA transfection approach was chosen and piggyBac transposase was chosen to complement Dd2 parasites with the HB3 allele of individual candidate genes (Balu et al., *PNAS,* 102: 16391-96 (2005)). With this method, successfully transfected parasites will carry both parental alleles and therefore be merodiploid for candidate genes. Nevertheless, the marked difference in ISPA-28 efficacy between the parental lines would be expected to produce a detectable change in transport phenotype upon complementation with the responsible gene. The high efficiency of random integration conferred by piggyBac permits rapid examination of many genes (Balu et al., *BMC Microbiol.,* 9: 83 (2009)).

Fourteen genes were cloned with their endogenous 5' and 3' UTR regions from the HB3 parent into the pXL-BacII-DHFR plasmid; a 15$^{th}$ construct containing a conserved but not annotated open reading frame (ORF 147 kb) was also prepared. Each was transfected individually along with a helper plasmid encoding the transposase into Dd2 parasites. Selection for hDHFR expression yielded parasites that stably carried both Dd2 and HB3 alleles for each candidate. Because an altered channel phenotype presumably requires expression of the HB3 allele, reverse transcriptase PCR was used to amplify polymorphic regions of each gene and the amplicons were sequenced to determine if both parental alleles were transcribed; this approach confirmed expression of 12 candidates. ISPA-28 dose responses for inhibition of sorbitol uptake by erythrocytes infected with each transfectant were performed. Two transfectants, expressing HB3 alleles for PFC0110w (clag 3.2) and PFC0120w (clag 3.1), produced significant changes in ISPA-28 efficacy with $K_{0.5}$ values between those of Dd2 and HB3, as expected for cells carrying channels from both parental lines (P=0.01 and $P<10^{-7}$ in comparison to Dd2, respectively). Limiting dilution cloning of the PFC0120w transfectant yielded a clone, Dd2-pB120w, which had undergone at least one integration event; its ISPA-28 $K_{0.5}$ was indistinguishable from the transfection pool. For both genes, quantitative analyses suggested relatively low level expression of the HB3 allele because the transfectant $K_{0.5}$ values (95±8 and 140±12 nM) were closer to those of Dd2 than of HB3. Without being bound by a particular theory or mechanism, it is believed that expression levels of the two parental alleles may be influenced by the genomic environment of the integration site, relative promoter efficiencies, and a gene silencing mechanism examined below.

Example 4

This example confirms a role for clag 3.1. and clag 3.2 in PSAC activity. This example also demonstrates that clag3 gene silencing and switched expression determine inhibitor affinity.

To examine the unexpected possibility that clag3 products contribute to PSAC activity, an allelic exchange strategy was used to transfer potent ISPA-28 block from the Dd2 line to HB3 parasites. Because Dd2 parasites express clag3.1 but not clag3.2 (Kaneko et al., *Mol. Biochem. Parasitol.*, 143: 20-28 (2005)), their clag3.1 gene presumably encodes high ISPA-28 affinity. Therefore, a transfection plasmid was constructed carrying a 3.2 kb fragment from the 3' end of the Dd2 clag3.1 allele, an in-frame C-terminal FLAG tag followed by a stop codon, and the fragment gene's 3' untranslated region (pHD22Y-120w-flag-PG1). Because this plasmid carries only a gene fragment and lacks a leader sequence to drive expression, an altered transport phenotype requires recombination into the parasite genome. HB3 was transfected with this plasmid and PCR was used to screen for integration into each of the five endogenous clag genes. This approach detected recombination into the HB3 clag3.2 gene; limiting dilution cloning yielded HB3$^{3rec}$, a clone carrying a single site integration event without residual episomal plasmid. DNA sequencing indicated recombination between single nucleotide polymorphisms at 3718 and 4011 bp from the HB3 clag3.2 start codon. This recombination site corresponded to successful transfer of downstream polymorphisms including a recognized hypervariable region at 4266-4415 bp; contamination with other laboratory parasite lines was excluded by fingerprinting.

Figure 2:
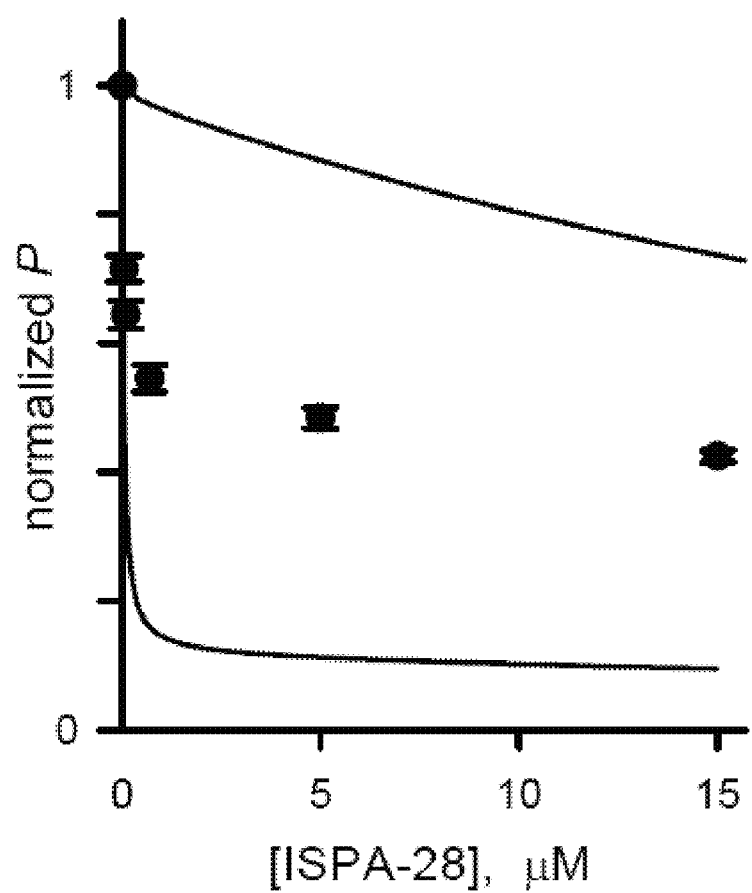

PSAC activity on HB3$^{3rec}$ exhibited a marked increase in ISPA-28 efficacy (FIG. 1), further supporting a role for clag3 genes in sorbitol and nutrient uptake. Although this allelic exchange strategy yielded a gene replacement in contrast to the complementations achieved with piggyBac, the channel's ISPA-28 affinity was again intermediate between those of HB3 and Dd2 (FIG. 2). Without being bound by a particular theory or mechanism, it is believed that several mechanisms may contribute to the quantitatively incomplete transfer of inhibitor affinity. First, two or more polymorphic sites on the protein might contribute to ISPA-28 binding. If some of these sites are upstream from the recombination event, the resulting chimeric protein may have functional properties distinct from those of either parental line. Second, the channel may contain additional unidentified subunits; here, transfection to replace each contributing HB3 gene with Dd2 alleles might be required to match the ISPA-28 affinity of Dd2. Finally, in addition to the chimeric clag3.2$_{BB3}$-3.1$_{Dd2}$ gene produced by transfection, HB3$^{3rec}$ also carries the clag3.1 gene endogenous to HB3 parasites. Expression of both paralogs could also produce an intermediate ISPA-28 affinity.

To explore these possibilities, a cell-attached patch-clamp was performed on HB3$^{3rec}$-infected cells. Individual channel molecules exhibiting ISPA-28 potencies matching those of each parental line were identified. These recordings excluded scenarios that require a homogenous population of channels.

In addition to the complex behavior of HB3$^{3rec}$, it was noticed that certain progeny from the genetic cross had lower ISPA-28 affinity than Dd2 despite inheriting the mapped chromosome 3 locus fully from the Dd2 parent. Because subtelomeric multigene families in *P. falciparum* are susceptible to recombination and frequent gene conversion events (Freitas-Junior et al., *Nature*, 407: 1018-22 (2000)), both clag3 paralogs and neighboring genomic DNA from 7C20 and Dd2 were sequenced but no DNA-level differences were found. Epigenetic mechanisms that may influence ISPA-28 affinity were therefore considered. clag3.1 and clag3.2 have been reported to undergo mutually exclusive expression (Cortes et al., *PLoS Pathog.*, 3: e107 (2007)). Monoallelic expression and switching, also documented for other gene families in *P. falciparum* (Chen et al. *Nature*, 394: 392-95 (1998); Lavazec et al., *Mol. Microbiol.*, 64: 1621-34 (2007)), allow individual parasites to express a single member of a multigene family. Daughter parasites resulting from asexual reproduction continue exclusive expression of the same gene through incompletely understood epigenetic mechanisms (Howitt et al., *Mol. Microbiol.*, 73: 1171-85 (2009)). After a few generations, some daughters may switch to expression of another member of the gene family, affording diversity that contributes to immune evasion (Sherf et al., *Annu. Rev. Microbiol.*, 62: 445-70 (2008)).

Reverse transcriptase PCR was performed and it was found that Dd2 expresses clag3.1 almost exclusively while the three discordant progeny express clag3.2 at measurable levels, suggesting epigenetic regulation. Selective pressure was therefore applied to progeny cultures with osmotic lysis in sorbitol solutions containing ISPA-28. Inclusion of ISPA-28 preferentially spares infected cells whose channels have high inhibitor affinity: these cells incur less sorbitol uptake and do not lyse. These selections, applied on multiple consecutive days, yielded marked reductions in parasitemia. Surviving parasites exhibited improved ISPA-28 affinity quantitatively matching that of the Dd2 parent. Identical selections applied to HB3 and three progeny inheriting its chromosome 3 locus did not change ISPA-28 affinity, excluding effects of the selections on unrelated genomic sites.

Real time qPCR using primers specific for each of the 5 clag genes revealed that selection with sorbitol and ISPA-28 reproducibly increased clag3.1 expression while decreasing that of clag3.2 in progeny inheriting the Dd2 locus. Selections applied to the parental HB3 line were without effect, consistent with its unchanged inhibitor affinity. These selections did not alter relative expression of other paralogs (clag2, clag8, and clag9).

Selections were also applied to HB3$^{3rec}$, which carries a chimeric clag3.2$_{HB3}$-3.1$_{Dd2}$ transgene and the clag3.1 gene native to HB3. In contrast to the lack of effect on the isogenic HB3 line, these synchronizations increased the transfectant's ISPA-28 affinity to a $K_{0.5}$ of 51±9 nM, matching that of Dd2 channels. This change in channel phenotype correlated with a near exclusive expression of the transgene, confirming that expression of HB3 clag3.1 by a subset of cells accounts for the intermediate ISPA-28 affinity. These findings also delimit the determinants of ISPA-28 binding to polymorphic sites within the Dd2 clag3.1 gene fragment transferred to HB3$^{3rec}$.

Without being bound to a particular theory or mechanism, it is believed that expression switching in *P. falciparum* multigene families occurs over several generations and should lead to a drift in population phenotype. After selection of the chimeric gene in HB3$^{3rec}$, continued in vitro propagation yielded a gradual decay in ISPA-28 affinity that correlated with decreasing transgene expression. As with other multigene families (Lavazec et al., *Mol. Microbiol.*, 64: 1621-34 (2007)), several factors may affect the steady-state ISPA-28 affinity and relative expression levels for the two clag3 genes upon continued culture without selective pressure.

Example 5

This example demonstrates reverse selection with ISPA-43 and a clag3 mutation in a leupeptin-resistant PSAC mutant.

A PSAC inhibitor with reversed specificity for the two Dd2 clag3 products was next sought. To this end, hits from the high-throughput screen of Example 2 were surveyed using the progeny clone 7C$_{20}$ before and after selection for clag3.1 expression. This secondary screen identified ISPA-43 as a PSAC inhibitor with an allele specificity opposite that of ISPA-28 (Formula B below ($K_{0.5}$ of 32 and 3.9 μM for channels associated with clag3.1 and clag3.2 genes from Dd2, respectively).

A stable parasite mutant with altered PSAC selectivity, gating, and pharmacology was recently generated by in vitro selection of HB3 with leupeptin (Lisk et al., *Antimicrob. Agents Chemother.*, 52: 2346-54 (2008)). Clag3 genes were sequenced from this mutant, HB3-leuR1, and identified a point mutation within its clag3.2 gene that changes the conserved A1210 to a threonine, consistent with a central role of clag3 genes in solute uptake. HB3-leuR1 silences its unmodified clag3.1 and preferentially expresses the mutated clag3.2 (expression ratio of 19.2±1.5), as required for a direct effect on PSAC behavior. Because this mutation is within a predicted transmembrane domain, it may directly account for the observed changes in channel gating and selectivity.

ISPA-43 Formula B

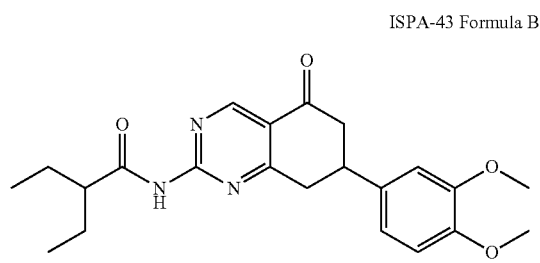 [SMILES: CCC(CC)C(=O)Nc1ncc2c(n1)CC(c1ccc(OC)c(OC)c1)CC2=O]

Sorbitol synchronizations with 4 μM ISPA-43 were then applied to the clag3.1-expressing 7C20 culture and achieved robust reverse selection: the surviving parasites exhibited both low ISPA-28 affinity and a reversed clag3 expression profile. Thus, inhibitors can be used in purifying selections of either clag3 gene. Because ISPA-28 affinity can be reduced either through drift without selective pressure or by selection for the alternate paralog with an inhibitor having reversed specificity, these studies alleviate concerns about indirect effects of exposure to sorbitol or individual inhibitors.

A stable parasite mutant with altered PSAC selectivity, gating, and pharmacology was recently generated by in vitro selection of HB3 with leupeptin (Lisk et al., *Antimicrob. Agents Chemother.*, 52: 2346-54 (2008)). Clag3 genes from this mutant, HB3-leuR1, were sequenced and a point mutation was identified within its clag3.2 gene that changed the conserved A1210 to a threonine, consistent with a central role of clag3 genes in solute uptake. HB3-leuR1 silenced its unmodified clag3.1 and preferentially expressed the mutated clag3.2 (expression ratio of 19.2±1.5), as required for a direct effect on PSAC behavior. Without being bound by a particular theory or mechanism, it is believed that because this mutation is within a predicted transmembrane domain, it may directly account for the observed changes in channel gating and selectivity.

Example 6

This example demonstrates that clag3 products are exposed at the host erythrocyte surface.

To directly contribute to PSAC activity, it is believed that at least some of the clag3 product would associate with the host membrane, presumably as an integral membrane protein. Polyclonal antibodies were therefore raised to a carboxy-terminal recombinant fragment conserved between the two clag3 products. Confocal microscopy with this antibody confirmed reports localizing these proteins to the host cytosol and possibly the erythrocyte membrane as well as within rhoptries of invasive merozoites (Vincensini et al., *Mol. Biochem. Parasitol.*, 160: 81-89 (2008)). To obtain more conclusive evidence, immunoblotting was used to examine susceptibility of these proteins to extracellular protease. Without protease treatment, a single ~160 kDa band was detected in whole-cell lysates, consistent with the expected size of clag3 products. Treatment with pronase E under conditions designed to prevent digestion of intracellular proteins reduced the amount of the full-length protein and revealed a 35 kDa hydrolysis fragment. In contrast, a monoclonal antibody against KAHRP, a parasite protein that interacts with the host membrane cytoskeleton but is not exposed (Kilejian et al., *Mol. Biochem. Parasitol.*, 44: 175-81 (1991)), confirmed that intracellular proteins are resistant to hydrolysis under these conditions. As reported for another protease (Baumeister et al., *Mol. Microbiol.*, 60: 493-04 (2006)), pronase E treatment significantly reduced PSAC-mediated sorbitol uptake; this effect was sensitive to protease inhibitors, suggesting that proteolysis at one or more exposed sites interferes with transport.

Ultracentrifugation of infected cell lysates revealed that the clag3 product is fully membrane-associated; a fraction could however be liberated by treatment with $Na_2CO_3$, which strips membranes of peripheral proteins (Fujiki et al., *J. Cell Biol.*, 93: 97-102 (1982)). Because this fraction was protease insensitive, it reflects an intracellular pool of clag3 product loosely associated with membranes. The C-terminal hydrolysis fragment was present only in the carbonate-resistant insoluble fraction, indicating an integral membrane protein.

Because the polyclonal antibodies might cross-react with clag products from other chromosomes, protease sensitivity was next examined in HB3$^{3rec}$, whose chimeric clag3 transgene encodes a C-terminal FLAG tag. Anti-FLAG antibody recognized a single integral membrane protein in HB3$^{3rec}$ and no proteins from the parental HB3 line, indicating specificity for the recombinant gene product. Treatment with pronase E prior to cell lysis and fractionation revealed a hydrolysis fragment indistinguishable from that seen with the antibody raised against the native protein's C-terminus.

The following procedures were followed for the experiments described in Examples 7-10:

Parasite Cultivation, Design of PLM and Growth Inhibition Studies

Asexual stage *P. falciparum* laboratory lines were propagated by standard methods in RPMI 1640 supplemented with 25 mM HEPES, 31 mM NaHCO$_3$, 0.37 mM hypoxanthine, 10 µg/mL gentamicin, and 10% pooled human serum. PLM is based on this standard medium and was designed after surveying parasite growth in media lacking individual constituents with known PSAC permeability: hypoxanthine, calcium panthothenate, and the amino acids Cys, Glu, Gln, Ile, Met, Pro, and Tyr (Saliba et al., *J. Biol. Chem.*, 273: 10190-10195 (1998)). PLM contained reduced concentrations of isoleucine (11.4 µM), glutamine (102 µM), and hypoxanthine (3.01 µM); human serum was exhaustively dialyzed against distilled H$_2$O prior to supplementation in this medium.

Growth inhibition experiments were quantified using a SYBR Green I-based fluorescence assay for parasite nucleic acid in 96-well format, as described previously (Pillai et al., *Mol. Pharmacol.*, 77: 724-733 (2010)). Ring-stage synchronized cultures were seeded at 1% parasitemia and 2% hematocrit in standard medium or PLM and maintained for 72 h at 37° C. in 5% O$_2$, 5% CO$_2$ without media change. Cultures were then lysed in 20 mM Tris, 10 mM EDTA, 0.016% saponin, and 1.6% triton X100, pH 7.5 with SYBR Green I at twice the manufacture's recommended concentration (Invitrogen, Carlsbad, Calif.). After a 45 min incubation, parasite DNA content was quantified by measuring fluorescence (excitation/emission wavelengths, 485/528 nm). For each inhibitor concentration, the mean of triplicate measurements was calculated after subtraction of background fluorescence from matched cultures killed by 20 µM chloroquine. Growth inhibition studies with the HB3$^{3rec}$ parasite were performed after transport-based selection with ISPA-28 to achieve expression of the chimeric clag3 gene generated by allelic exchange transfection.

Transport Inhibition Assays

Inhibitor affinity for PSAC block was determined using a quantitative transmittance assay based on osmotic lysis of infected cells in sorbitol (Wagner et al., *Biophys. J.*, 84: 116-123 (2003)). Parasite cultures were enriched at the trophozoite stage using the Percoll-sorbitol method, washed, and resuspended at 37° C. and 0.15% hematocrit in 280 mM sorbitol, 20 mM Na-HEPES, 0.1 mg/ml BSA, pH 7.4 with indicated concentrations of inhibitors. PSAC-mediated sorbitol uptake produces osmotic lysis, which was continuously tracked by measuring transmittance of 700 nm light through the cell suspension (DU640 spectrophotometer with Peltier temperature control, Beckman Coulter). Inhibitor dose responses were calculated from the time required to reach fractional lysis thresholds. ISPA-28 dose responses were fitted to the sum of two Langmuir isotherms (Eq/S1). Other inhibitors had dose responses that are adequately fitted by a single Langmuir isotherm.

To examine possible inhibitor metabolism in parasite culture, Dd2 parasites were cultivated in standard media with 40 µM ISPA-28 at 37° C. for 72 h. After centrifugation, the culture supernatant was used as a source of ISPA-28 for comparison to freshly-prepared compound in transport inhibition studies.

QTL Analysis

We sought genetic loci associated with ISPA-28 growth inhibitory efficacy in the Dd2×HB3 genetic cross (Wellems et al., *Nature*, 345: 253-255 (1990)) using 448 previously selected polymorphic markers that distinguish the Dd2 and HB3 parental lines (Nguitragool et al., *Cell*, 145: 665-677 (2011)). QTL analysis was performed using R/qtl software (freely available at http://www.rqtl.org/) as described (Broman et al., *Bioinformatics*, 19: 889-890 (2003)) and conditions suitable for the haploid asexual parasite. A P=0.5 significance threshold was estimated with permutation analysis. Growth inhibition data at 0.3 and 10 µM ISPA-28 identified the same locus reported with 3 µM ISPA-28. Additional QTL were sought with secondary scans by controlling for the clag3 locus.

Quantitative RT-PCR

Two-step real-time PCR was used to quantify clag gene expression using allele-specific primers developed previously (Nguitragool et al., *Cell*, 145: 665-677 (2011)). RNA was harvested from schizont-stage cultures with TRIzol reagent (Invitrogen), treated with DNase to remove residual genomic DNA contaminant, and used for reverse transcription (SuperScriptIII and oligo-dT priming, Invitrogen). Negative control reactions without reverse transcriptase confirmed there was no genomic DNA contamination. Real-time PCR was performed with QuantiTect SyBr Green PCR kit (Qiagen), the iCycler iQ multicolor real-time PCR system (Bio-Rad), and clag gene-specific primers. Serial dilution of parasite genomic DNA was used to construct the standard curve for each primer pair. PF7_0073 was used as a loading control as it is constitutively expressed. Transcript abundance for each clag gene was then determined from amplification kinetics.

PCR Studies for Clag3 Recombination

The clag3 locus of Dd2-PLM28 was characterized with genomic DNA and allele-specific primers:

```
3.1f
                                        (SEQ ID NO: 68)
(5'-GTGCAATATATCAAAGTGTACATGCA-3'), 3.1r
                                        (SEQ ID NO: 69)
(5'-AAGAAAATAAATGCAAAACAAGTTAGA-3'), 3.2f
                                        (SEQ ID NO: 41)
(5'-GTTGAGTACGCACTAATATGTCAATTTG-3'),
and 3.2r
                                        (SEQ ID NO: 42)
(5'-AACCATAACATTATCATATATGTTAATTACAC-3').
``` cDNA Prepared from schizontstage cultures was also used with these primers to examine expression of both native and chimeric clag3 genes.

Southern Blot

A clag3-specific probe was prepared by PCR amplification from Dd2 genomic DNA using 5'-ATTTA-CAAACAAAGAAGCTCAAGAGGA-3' (SEQ ID NO: 70) and 5'-TTTTCTATATCTTCATTTTCTTTAATTGTTC-3' (SEQ ID NO: 71) in the presence of Digoxygenin (DIG)-dUTP (Roche). Probe specificity was confirmed by blotting against full-length PCR amplicons of the five clag genes generated from Dd2 genomic DNA with primers.

Genomic DNA was digested with indicated restriction enzymes (New England BioLabs), subjected to electrophoresis in 0.7% agarose, acid depurinated, transferred and crosslinked to Nylon membranes. The blot was then hybridized overnight at 39° C. with the above DIG-labeled probe in DIG Easy Hyb (Roche), and washed with low and high stringency buffers (2×SSC, 0.1% SDS, 23° C. followed by 1×SSC, 0.5% SDS, 50° C.) prior to DIG immunodetection according to the manufacturer's instructions.

Mammalian Cytotoxicity

Cytotoxicity of PSAC inhibitors was measured with human HeLa cells (ATCC # CLL-2) in 96-well plates at 4000 cells/well. Cultures were incubated with each inhibitor at 37° C. for 72 h in Minimal Essential Medium (Gibco/Invitrogen, Carlsbad, Calif.) supplemented with 10% fetal calf serum. Cell viability was quantified using the vital stain MTS [3-(4,5-dimethylthiazol-2-yl)-5-(3-carboxymethonyphenol)-2-(4-sulfophenyl)-2H-tetrazolium, inner salt], as described (Marshall et al., *Growth Regul.*, 5: 69-84 (1995)). The reported $CC_{50}$ value is the concentration of an inhibitor that reduces conversion of MTS to formazan by 50%.

Example 7

This example demonstrates that ISPA-28 kills Dd2 cells in vitro when nutrient availability in the media is reduced.

ISPA-28 blocks PSAC on Dd2-infected cells with high affinity and has only weak activity against channels from HB3 parasites ($K_{0.5}$ of 56±5 nM and 43±2 μM, respectively) (Nguitragool et al., *Cell*, 145: 665-677 (2011)). If channel activity serves a role in the growth of the intracellular parasite, this small molecule inhibitor would be expected to interfere with propagation of Dd2 cultures but spare those of HB3. The initial in vitro parasite growth studies revealed an insignificant difference with both parasite lines exhibiting sustained growth in RPMI-based media despite high ISPA-28 concentrations ($IC_{50}$ values >40 μM each, P=0.35 for a difference).

It was determined that ISPA-28 efficacy against Dd2 channels is not compromised by metabolism of the inhibitor under in vitro culture conditions. ISPA-28 is also not significantly adsorbed by serum protein or lipids, a phenomenon known to reduce activity of some PSAC inhibitors and many therapeutics (Matsuhisa et al., *Chem. Engineering J.*, 34: B21-B27 (1987)). Thus, ISPA-28 does not to inhibit the growth of Dd2 parasites under standard in vitro culture conditions.

One possibility is that channel activity is involved in the survival of malaria parasites, but that the low level transport remaining in the presence of inhibitor adequately meets parasite demands under standard in vitro culture conditions. Consistent with this, sustained channel-mediated uptake in Dd2-infected erythrocytes even with high ISPA-28 concentrations was observed. Significantly less residual uptake was observed with compound (31), a broad spectrum PSAC inhibitor with a comparable inhibitory $K_{0.5}$ value for Dd2 channels (Pillai et al., *Mol. Pharmacol.*, 77: 724-733 (2010)). (P<10-4 for comparison of these inhibitors at 10 μM). The unexpected difference in residual channel activity with these inhibitors may account for their differing efficacies against in vitro parasite growth ($IC_{50}$ values of ~50 μM and 4.7 μM, respectively; Table 5).

TABLE 5

| Compound Name | Structure | Transport inhibition $K_{0.5}$, nM | RPMI growth $IC_{50}$, μM | PLM growth $IC_{50}$, μM | $IC_{50}$ ratio |
|---|---|---|---|---|---|
| furosemide | 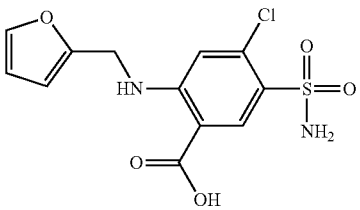 [SMILES: NS(=O)(=O)c1cc(C(=O)O)c(NCc2ccco2)cc1Cl] | 2700 | >200 | 21 | >9.5 |
| dantrolene | 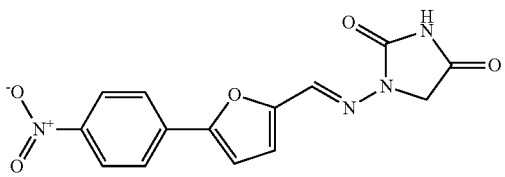 | 1200 | 42 | 3.8 | 18 |
| (24) | 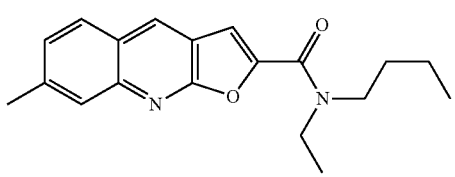 24 | 87 | 23 | 0.27 | 114 |
| (25) | 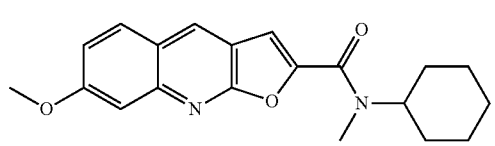 25 | 33 | 15 | 0.17 | 86 |

TABLE 5-continued

| Compound Name | Structure | Transport inhibition $K_{0.5}$, nM | RPMI growth $IC_{50}$, μM | PLM growth $IC_{50}$, μM | $IC_{50}$ ratio |
|---|---|---|---|---|---|
| (280) | 280 | 6 | 18 | 0.23 | 270 |
| (31) | 31 | 84 | 4.7 | 0.41 | 15 |
| (3) (TP-52) | 3 | 25 | 7.3 | 0.19 | 38 |
| Cpd 80 | 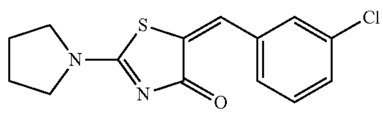 [SMILES: O=C1N=C(N2CCCC2)S/C1=C/c1cccc(Cl)c1] | 44 | 12.5 | 0.17 | 130 |
| Cpd 50 | 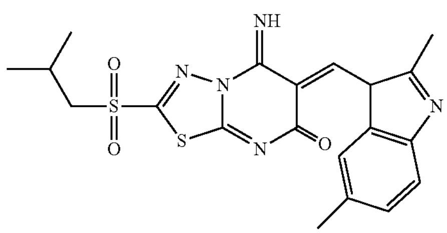 [SMILES: CC1=Nc2ccc(C)cc2C1/C=C1/C(=N)N2N=C(S(=O)(=O)CC(C)C)SC2=NC1=O] | 81 | >30 | 2.0 | >15 |
| ISG-21 | 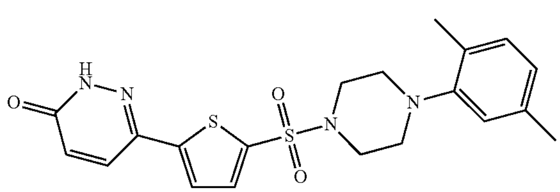 [SMILES: Cc1ccc(C)c(N2CCN(S(=O)(=O)c3ccc(-c4ccc(=O)[nH]n4)s3)CC2)c1] | 2.6 | 1.5 | 0.002 | 800 |
| chloroquine | | inactive | 0.22 | 0.34 | 0.67 |
| mefloquine | | inactive | 0.022 | 0.033 | 0.66 |
| artemisinin | | inactive | 0.018 | 0.026 | 0.66 |

Without being bound to a particular theory or mechanism, it is believed that incomplete block with high ISPA-28 concentrations despite a low $K_{0.5}$ value for Dd2 channels suggests a complex mechanism of inhibition. While dantrolene and furosemide dose responses are adequately fitted by the equation that assumes a 1:1 stoichiometry for inhibitor and channel molecules, the ISPA-28 dose response was not well fit. An improved fit was obtained with a two-component Langmuir equation. Because this two-component equation is compatible with several possible mechanisms, the ISPA-28 stoichiometry and precise mode of channel block has not yet been determined.

Without being bound by a particular theory or mechanism, it is believed that if PSAC functions in nutrient acquisition for the intracellular parasite (Desai et al., *Nature*, 406: 1001-1005 (2000)), then the incomplete inhibition by ISPA-28 may permit adequate nutrient uptake. Many nutrients are present at supraphysiological concentrations in the general purpose RPMI 1640 medium (Sato et al., *Curr. Protoc. Cell Biol.*, 1: Unit1.2 (2001)). The large inward concentration gradient for nutrients in this medium could sustain parasite nutrient uptake despite near-complete channel block. Nutrients with PSAC-mediated uptake were surveyed and isoleucine, glutamine, and hypoxanthine were selected because their isolated removal from media adversely affected parasite cultures. Isoleucine and glutamine dose responses revealed that both could be reduced by >90% with negligible effects on propagation of either HB3 or Dd2, consistent with nutrient excess in standard media. Threshold concentrations of these amino acids as well as of hypoxanthine, a purine with high PSAC permeability, were selected (Gero et al., *Adv. Exp. Med. Biol.*, 309A: 169-172 (1991); Asahi et al., *Parasitology*, 113: 19-23 (1996)). To reduce the inward gradient for nutrient uptake, a PSAC-limiting medium (PLM) was prepared that uses these threshold values while following the RPMI 1640 formulation for all other solutes. Without being bound by a particular theory or mechanism, it is believed that the reduced nutrient content of the PLM medium more closely mimics the nutrient availability under in vivo physiological conditions as compared to RPMI 1640 medium. Both Dd2 and HB3 parasites could be propagated continuously in PLM (>2 weeks), though at somewhat reduced rates. It was observed that cultures with low parasitemias grew well in PLM, but that rates decreased with higher parasite burden, consistent with nutrient limitation and competition between infected cells in culture.

Figure 3A:
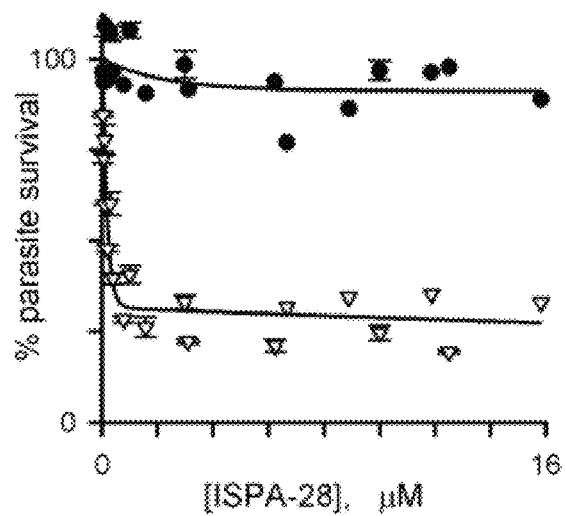
FIG. 3A is a graph showing % survival of Dd2 (open triangles) or HB3 (filled circles) in PLM medium as a function of ISPA-28 concentration (04). Solid lines represent the best fits to a two-component exponential decay.

In contrast to the poor ISPA-28 efficacy against parasite growth in the standard RPMI 1640 medium, studies using PLM revealed potent killing of Dd2 parasites and continued weak activity against HB3 ($I_{C50}$ values of 0.66±0.20 04 and 52±19 04, respectively; P<10-4; FIG. 3A). Although there is a nonlinear relationship between nutrient uptake and parasite growth, these $I_{C50}$ values are in reasonable agreement with the transport $_{K0.5}$ values for PSAC block by ISPA-28.

Example 8

This example demonstrates the ISPA-28 growth inhibition phenotype in the progeny of a Dd2×HB3 genetic cross.

Figure 3B:
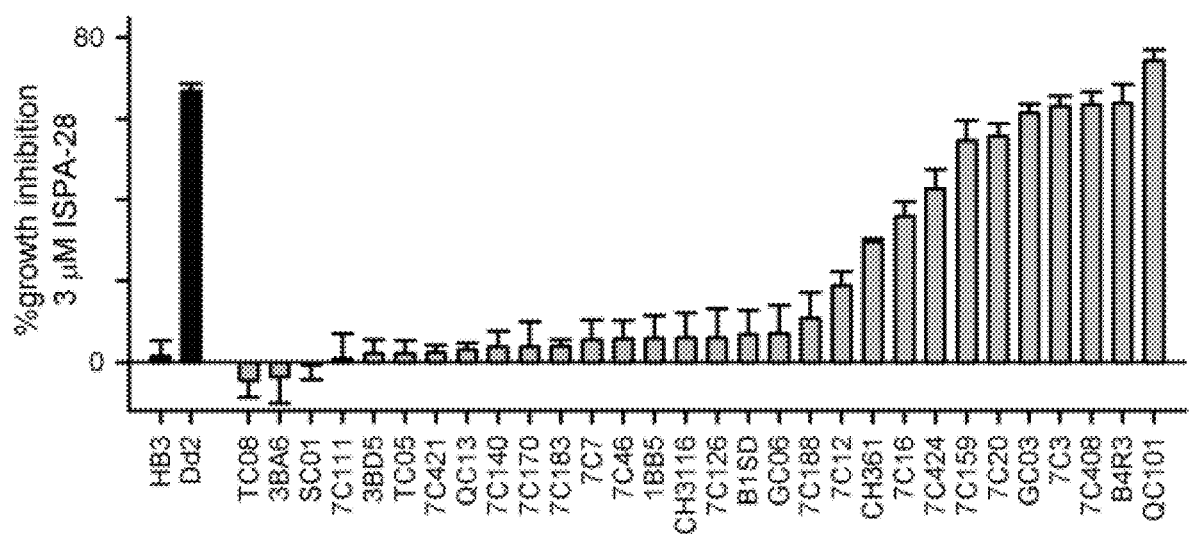
FIG. 3B is a graph showing mean±SEM % parasite growth inhibition by 3 μM ISPA-28 for indicated parental lines and progeny clones.

Linkage analysis using an independent transport phenotype and this genetic cross have recently implicated two clag3 genes from parasite chromosome 3 in PSAC-mediated solute uptake at the host membrane (Nguitragool et al., *Cell*, 145: 665-677 (2011)). Here, the growth inhibition studies revealed a broad range of ISPA-28 efficacies for progeny clones, with many progeny resembling one or the other parent. Because HB3 and some progeny had high growth $IC_{50}$ values that could not be precisely estimated, linkage analysis was performed using growth inhibition at 3 μM ISPA-28, a concentration that optimally distinguishes the parental phenotypes (FIG. 3B). This analysis identified a primary association of ISPA-28 growth inhibition with the clag3 locus, providing evidence for a role of this locus in inhibition of both solute transport and parasite killing by ISPA-28. Additional contributing peaks were sought by removing the effects of the clag3 locus; this approach did not identify other statistically significant genomic loci.

The mapped locus is at the proximal end of the parasite chromosome 3 and contains approximately 40 genes. To determine whether clag3 genes are responsible for ISPA-28 mediated killing, growth inhibition studies were performed with HB3$^{3rec}$, a parasite clone generated by allelic exchange transfection of HB3 to replace the 3' end of the native clag3.2 gene with the corresponding fragment from the clag3.1 of Dd2. When this chimeric gene is expressed, HB3$^{3rec}$ exhibits high affinity inhibition by ISPA-28 ($K_{0.5}$ of 51±9 nM, P=0.88 for no difference from Dd2) (Nguitragool et al., *Cell*, 145: 665-677 (2011)). Here, HB3$^{3rec}$ was used in growth inhibition studies with PLM and it was found that it is sensitive to ISPA-28 at levels matching Dd2. Because HB3$^{3rec}$ is otherwise isogenic with the resistant HB3 line, this finding indicates that ISPA-28 kills parasites primarily via action on the clag3 product and associated channel activity. Furthermore, the requirement for nutrient restriction to detect ISPA-28 mediated killing supports a role of PSAC in parasite nutrient acquisition.

Example 9

This example demonstrates the selection of resistant clag3 alleles though ISPA-28 mediated killing.

Most laboratory parasite lines carry two copies of clag3 genes, both on the Watson strand of the chromosome 3 locus. Epigenetic mechanisms control expression of these genes with individual parasites preferentially expressing one of the two alleles. Upon asexual replication, most daughter parasites continue to express the same allele, but a few undergo switching and express the other allele. In vivo, gene switching is used by malaria parasites and other pathogens to evade host immune responses against crucial surface-exposed antigens.

ISPA-28 was previously used to examine clag3 gene switching (Nguitragool et al., *Cell*, 145: 665-677 (2011)). This compound is a potent and specific inhibitor of channels associated with expression of the Dd2 clag3.1 gene; it has little or no activity against channels formed by expression of Dd2 clag3.2 or of either clag3 in unrelated parasite lines. The ISPA-28 binding site was delimited to the C-terminus of the clag3.1 product; a short hypervariable domain within this region is exposed at the erythrocyte surface and may define the ISPA-28 binding pocket. ISPA-28 was used to select for cells expressing the Dd2 clag3.1 allele through osmotic lysis in solutions containing ISPA-28 and sorbitol, a sugar alcohol with high PSAC permeability. Sorbitol selects for this allele because osmotic lysis eliminates infected cells whose channels are not blocked by ISPA-28. Of note, these selections were performed on three progeny clones inheriting the Dd2 clag3 locus, but not on Dd2 as this parental line already expresses clag3.1 exclusively. These selections were without effect on HB3 or progeny clones that inherit its clag3 locus because neither of the two HB3 alleles encodes high affinity ISPA-28 inhibition.

Figure 4A:
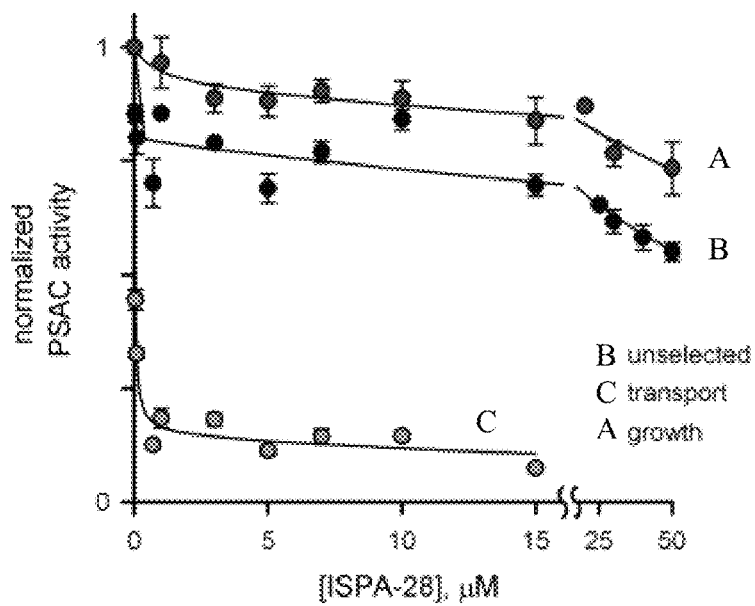
FIG. 4A is a graph showing mean±SEM ISPA-28 dose responses for PSAC inhibition before (B) and after transport selection of the 7C20 line (C) followed by PLM growth selection (A).
Figure 4B:
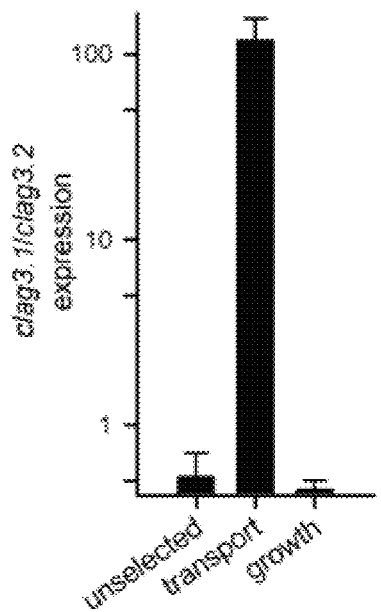
FIG. 4B is a graph showing expression ratio for the two clag3 alleles clag3.1 and clag3.2 before (unselected) and after (transport) selection of the 7C20 line followed by PLM growth selection (growth). Bars represent mean±SEM of replicates from 2-4 separate trials each.

Here, it was hypothesized that in vitro growth inhibition by ISPA-28 may also select for cells expressing individual clag3 genes. Without being bound by a particular theory or mechanism, it is believed that while sorbitol-induced osmotic lysis selects for cells that express the ISPA-28 sensitive clag3.1, growth inhibition in PLM should favor cells expressing the resistant clag3.2 allele because only parasites whose channels are not blocked by ISPA-28 will meet their nutrient demands. The progeny clone 7C20, which carries the Dd2 clag3 locus and expresses both alleles in unselected cultures (FIGS. 4A-4B), was examined. After selection with osmotic lysis in sorbitol and ISPA-28, surviving parasites had PSAC inhibitor affinity matching the Dd2 parent and predominantly expressed the clag3.1 allele. The culture was then propagated in PLM containing 5 µM ISPA-28 for a total of 10 days; microscopic examination of smears during this treatment revealed near complete sterilization of the culture. Transport studies on parasites surviving this second treatment revealed a marked reduction in ISPA-28 affinity, indicating that in vitro propagation with PSAC inhibitors can be used to select for altered channel phenotypes. RT-PCR confirmed strong negative selection against clag3.1 to yield a parasite population that preferentially expresses clag3.2. There were also modest changes in expression of clag genes on other chromosomes, suggesting that these paralogs may also contribute to PSAC activity. The opposing effects of ISPA-28 on in vitro growth inhibition and on susceptibility to transport-induced osmotic lysis permit purifying selections of either clag3 allele and reveal a strict correlation with channel phenotype.

Surprisingly, the Dd2 parental line retains exclusive expression of clag3.1 in unselected cultures despite being isogenic with 7C20 at the clag3 locus (Nguitragool et al., *Cell*, 145: 665-677 (2011)). To explore possible mechanisms, it was sought to select Dd2 parasites expressing the alternate clag3.2 allele. Transport selection was tried using osmotic lysis with ISPA-43, a structurally distinct PSAC inhibitor with 10-fold higher affinity for channels formed by expression of the Dd2 clag3.2 than of clag3.1. Although this approach has been successfully used to select for 7C20 parasites expressing clag3.2 (Nguitragool et al., *Cell*, 145: 665-677 (2011), it was insufficient to affect channel phenotype in Dd2 parasites despite repeated selections over 4 months.

Figure 5A:
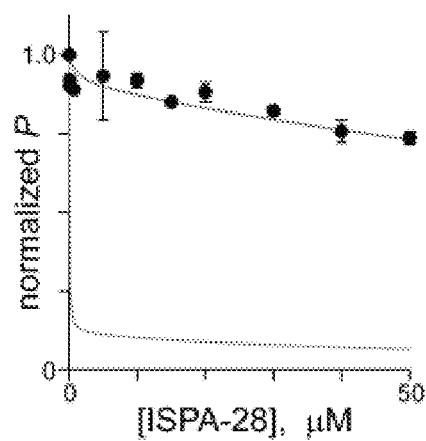
FIG. 5A is a graph showing ISPA-28 dose response for PSAC inhibition in the Dd2-PLM28 line (black circles, mean±SEM of up to 5 measurements each). Solid lines reflect the dose responses for clag3.1 and clag3.2 expression in 7C20 (bottom and top lines, respectively).

Negative selection was attempted with growth inhibition in PLM containing ISPA-28. After 2 cycles of drug pressure with 5 µM ISPA-28 for a total of 17 days, resistant cells were identified and characterized after limiting dilution to obtain the clone Dd2-PLM28. Consistent with killing primarily via PSAC inhibition, transport studies using this resistant clone revealed a marked reduction in inhibitor affinity (FIG. 5A). Although the ISPA-28 dose response quantitatively matched that of 7C20 parasites after identical PLM-based selection (upper solid line, FIG. 5A), full length clag3.2 transcript was still undetectable, excluding the simple prediction of gene switching. Spontaneous recombination between the two clag3 genes was considered, and a chimeric clag3 transcript was identified using a forward clag3.1 primer and a reverse clag3.2 primer; PCR confirmed that this chimera is present in the selected parasite's genome but absent from the original Dd2 line. Southern blotting with a clag3 specific probe detected three discrete bands in the selected clone but only the expected two bands in unselected Dd2 parasites, implicating a recombination event to produce three clag3 genes in Dd2-PLM28. The size of the new band, ~16 kb, is consistent with homologous recombination between clag3.1 and clag3.2 in Dd2-PLM28. DNA sequencing indicated that the chimeric gene derives its 5' untranslated region and the first ~70% of the gene from clag3.1. After a crossover between single nucleotide polymorphisms at 3680 and 3965 bp from the start codon, the gene carries the 3' end of clag3.2. Thus, the chimeric gene is driven by the clag3.1 promoter, but encodes a protein with the C-terminal variable domain of clag3.2. This altered C-terminus accounts for the reduced ISPA-28 efficacy against nutrient uptake and, hence, survival of this clone in the selection. Without being bound by a particular theory or mechanism, it is believed that the proposed homologous recombination also produces a parasite having a single clag3 gene and high ISPA-28 affinity, but that recombinant is not expected to survive growth inhibition selection in PLM with ISPA-28.

Figure 5B:
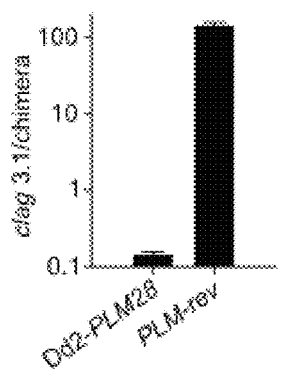
FIG. 5B is a graph showing the ratio quantifying relative expression of clag3 and the chimeric gene in Dd2-PLM28 before and after transport-based selection for clag3.1 using ISPA-28 (PLM28-rev) presented on a log scale.

Quantitative RT-PCR was then used to examine transcription of clag genes in Dd2-PLM28 and found that the chimeric gene is preferentially expressed (8.9±1.3 fold greater than clag3.1, $P<0.002$). Transport-based selection in sorbitol with ISPA-28 was used to examine whether Dd2-PLM28 can undergo expression switching. This second selection yielded parasites that express the native clag3.1 almost exclusively (PLM-rev, FIG. 5B). Transport studies revealed an ISPA-28 dose response identical to that of the original Dd2 line, as expected. Thus, the new chimeric clag3 gene can undergo epigenetic silencing and switching with clag3.1. DNA sequencing of the gene's promoter region did not reveal any mutations relative to that of 7C20.

Without being bound by a particular theory or mechanism, it is believed that recombination between the two clag3 genes occurs with relative ease, consistent with reports of frequent recombination events in the parasite's subtelomeric regions (Freitas-Junior et al., *Nature*, 407: 1018-22 (2000)). It is also believed that such recombination events may serve to increase diversity in PSAC phenotypes, apparent here as affording survival of a parasite with three clag3 genes under selective pressure.

Example 10

This example demonstrates the comparison of growth inhibitory effects of PSAC inhibitors in PLM and standard media.

Furosemide and dantrolene are known non-specific inhibitors with relatively low PSAC affinity. These compounds are also adsorbed by serum, but are approved therapeutics in other human diseases. They are only weakly effective against parasite growth in standard medium, but have significantly improved activity in PLM. Eight high affinity PSAC inhibitors from 5 distinct scaffolds recently identified by high-throughput screening were also tested (Pillai et al., *Mol. Pharmacol.*, 77: 724-733 (2010)). Each exhibited significantly improved potency when nutrient concentrations are reduced, strengthening the evidence for the channel's role in nutrient acquisition. The extent of improved efficacy was variable, but many compounds exhibited a >100-fold improvement in parasite killing upon nutrient restriction ($IC_{50}$ ratio, Table 5). Factors such as the stoichiometry of inhibitor:channel interaction and resultant changes in the concentration dependence of channel block, compound stability in culture, and adsorption by serum may influence this ratio.

To explore therapeutic potential, HeLa cell cytotoxicity was examined in vitro. Several potent PSAC inhibitors were found to be nontoxic and highly specific for parasite killing (Table 6).

TABLE 6

| PSAC Inhibitor | HeLa cell $CC_{50}$, µM | specificity (HeLa $CC_{50}$/parasite PLM $IC_{50}$) |
|---|---|---|
| (24) | 30 | 110 |
| (280) | >100 | >430 |
| (31) | >100 | >240 |
| (3) | >100 | >530 |
| Cpd 50 | >100 | >50 |
| ISG-21 | 86 | 43,000 |

Finally, in vitro growth inhibition experiments were performed with chloroquine, mefloquine, and artemisinin, approved antimalarial drugs that work at unrelated targets within the intracellular parasite. These drugs do not inhibit PSAC-mediated solute uptake. In contrast to improved killing by PSAC inhibitors, these drugs were modestly less effective in PLM than in RPMI (Table 5), excluding non-specific effects of modified in vitro growth conditions. Without being bound by a particular theory or mechanism, it is believed that the robust improvement in parasite killing for PSAC inhibitors upon nutrient restriction is in contrast to the effect on existing antimalarial drugs and, therefore, implicates a novel mechanism of action. Because both isolate-specific and broad spectrum PSAC inhibitors exhibit improved efficacy in PLM, these studies provide experimental evidence for a role of PSAC in nutrient uptake by the intracellular parasite.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising:
i) a compound of formula (I):

$$Q-Y-R^1-R^2 \quad (I),$$

wherein:
Q is a heterocyclic amido group linked to a heterocyclic group, optionally substituted with one or more substituents selected from the group consisting of halo, hydroxy, mercapto, alkoxy, alkylthio, nitro, cyano, amino, alkyl, aryl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;
Y is $SO_2$;
$R^1$ is piperidinyl which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;
$R^2$ is aryloxyalkyl which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;
or a pharmaceutically acceptable salt thereof; and
ii) at least one other antimalarial compound.

2. The pharmaceutical composition of claim 1, wherein the at least one other antimalarial compound is selected from the group consisting of:
a) a compound of formula II:

<img formula (II)> wherein $R^{100}$ is hydrogen or alkyl and $R^{200}$ is arylalkyl, optionally substituted on the aryl with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl; or $R^{200}$ is a group of formula (III):

<img formula (III)>

$$-(CH_2)_n-N\bigcirc N-\bigcirc-OR^2$$
with $R^9$ on piperazine N wherein n=0 to 6;
or $R^{100}$ and $R^{200}$ together with the N to which they are attached form a heterocycle of formula IV:

<img formula (IV)> wherein X is N or CH; and
$Y_1$ is aryl, alkylaryl, dialkylaryl, arylalkyl, alkoxyaryl, or heterocyclic, optionally substituted with one or more substituents selected from the group consisting of halo, hydroxyl, nitro, cyano, amino, aminoalkyl, alkylamino, alkylcarbonyl, alkoxycarbonyl, aminocarbonyl, and formyl; and
$R^3$-$R^{10}$ are hydrogen or alkyl; or a pharmaceutically acceptable salt thereof;
(b) a compound of formula V:

<img formula (V)> wherein
Z is a group having one or more 4-7 membered rings, wherein at least one of the rings has at least one heteroatom selected from the group consisting of O, S, and N; and when two or more 4-7 membered rings are present, the rings may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl;

$R^a$ is hydrogen, alkyl, or alkoxy;

L is a bond, alkyl, alkoxy, $(CH_2)_r$, or $(CH_2O)_s$, wherein r and s are independently 1 to 6;

$Q_1$ is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl; and when L is alkyl or alkoxy, $Q_1$ is absent;

or a pharmaceutically acceptable salt thereof; and (c) a compound of formula VI:

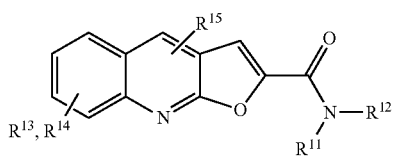

(VI)

wherein $R^{11}$ and $R^{12}$ are independently hydrogen, alkyl, cycloalkyl, or aryl which is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl;

$R^{13}$-$R^{15}$ are independently selected from the group consisting of alkyl, halo, alkoxy, hydroxy, nitro, cyano, amino, alkylamino, aminoalkyl, alkylcarbonyl, alkoxycarbonyl, aminocarbonyl, and formyl;

or a pharmaceutically acceptable salt thereof.

3. The pharmaceutical composition of claim 1, wherein Q is

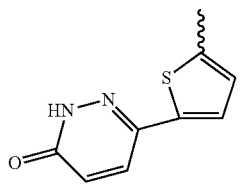

4. The pharmaceutical composition of claim 1, wherein $R^1$ is

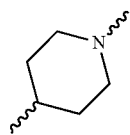

5. The pharmaceutical composition of claim 1, wherein $R^2$ is

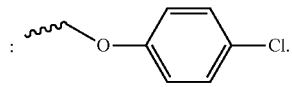

6. The pharmaceutical composition of claim 2, wherein the compound of formula (II) is:

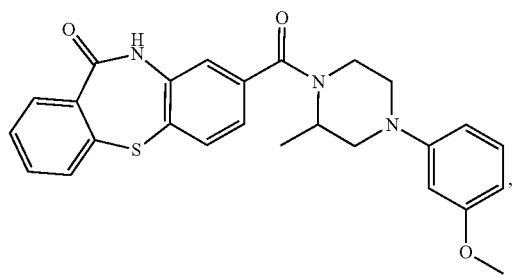

1

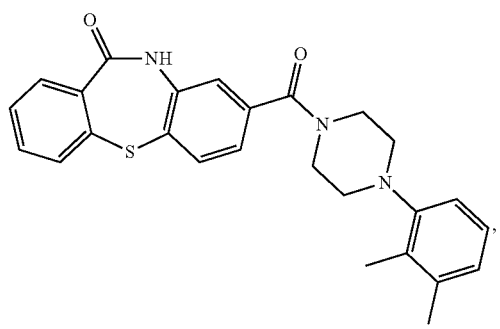

2

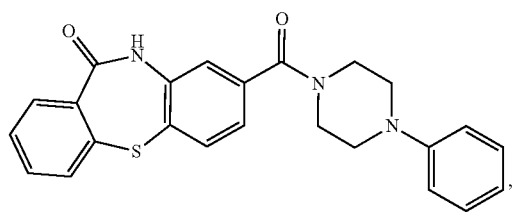

3

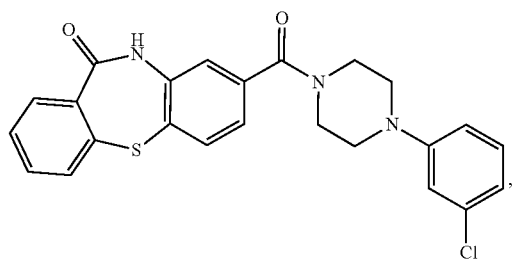

4

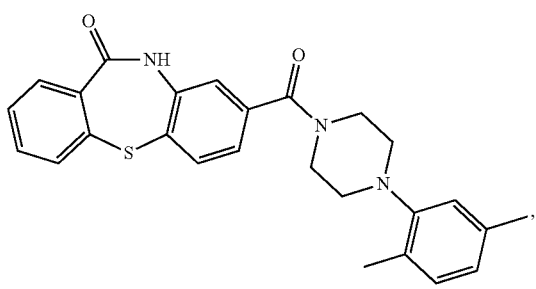
5
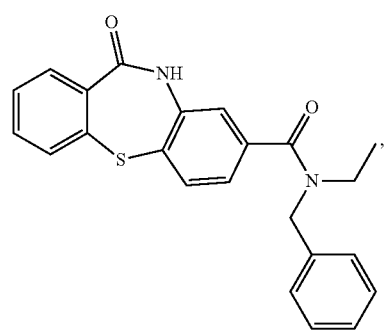
31
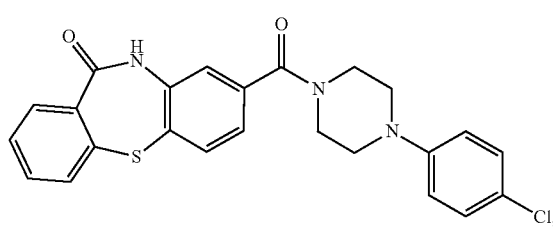
6
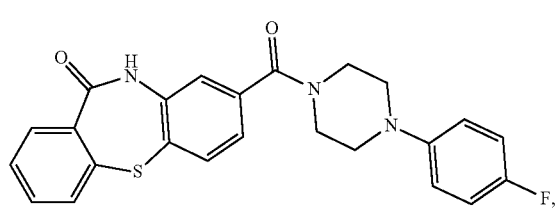
7
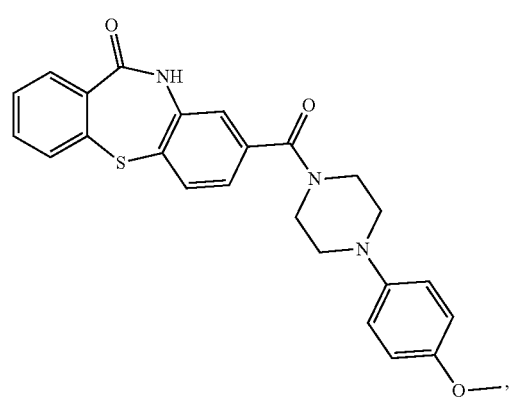
8
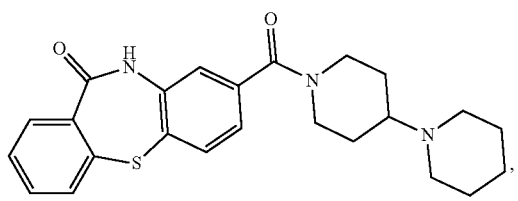
9
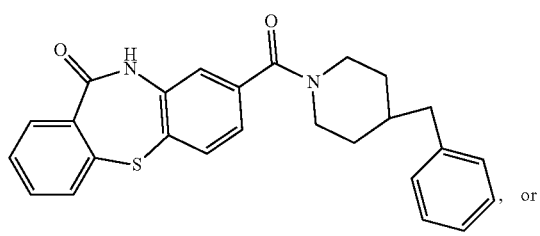
10
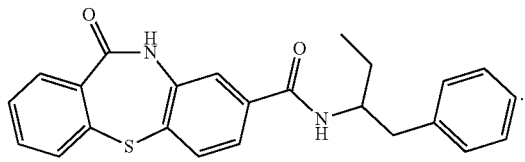
, or
11
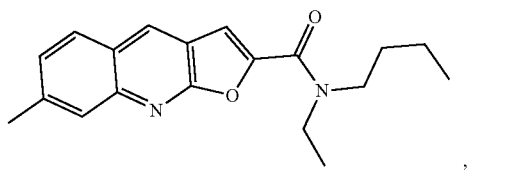
7. The pharmaceutical composition of claim 2, wherein the compound of formula (VI) is:
24
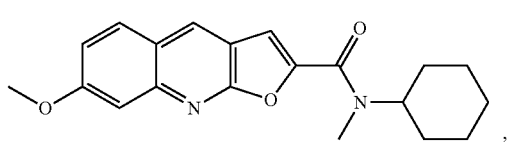
25
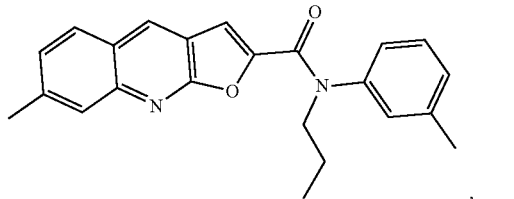
26
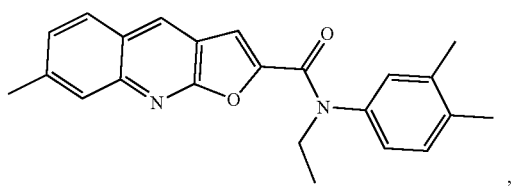
27

28
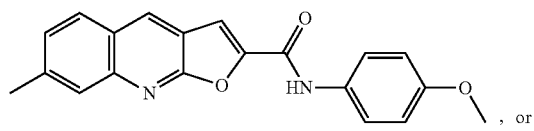
, or
29
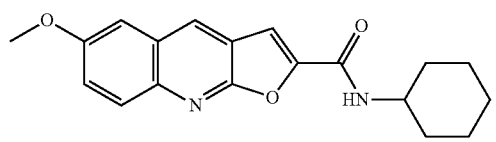
8. A pharmaceutical composition comprising (i) a compound of ISG-23 or a pharmaceutically acceptable salt thereof wherein ISG-23 comprises the structure of
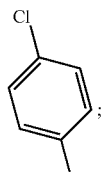
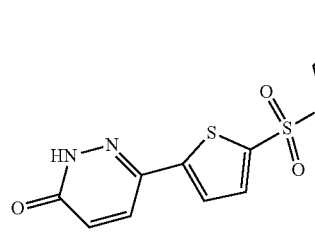
MB-23
and (ii) at least one other antimalarial compound.
* * * * *

SEQUENCE LISTING

<160> NUMBER OF SEQ ID NOS: 79

<210> SEQ ID NO 1
<211> LENGTH: 4254
<212> TYPE: DNA
<213> ORGANISM: Plasmodium falciparum

<400> SEQUENCE: 1

```
atggtttcat ttttaaaac  tccaatcttt  attttaatta  tcttttata   cttaaatgaa    60 aaggtaatat gttcaataaa tgaaaatcaa aatgaaaatg ataccattag tcaaaatgtc   120
aaccaacatg aaaatattaa tcaaaatgta aatgataatg acaatattga acaattaaaa   180
tccatgattg gaaatgatga actacataag aatttaacaa tattagaaaa attaattta    240 gagtctttag aaaaagataa attaaaatat cctctcctta aacaaggaac tgaacaattg   300
atagatatat caaaatttaa taaaaaaaat attacagatg cggatgatga aacgtacatc   360
atacccaccg tccaatcaac gtttcacgat attgtgaaat acgaacatct tataaaagaa   420
caatcaatag aaatttacaa ttctgatata tcagataaaa ttaagaaaaa aatttttata   480
gtaagaacat tgaaaaccat aaaattaatg cttataccat taaactcgta caaacaaaat   540
aatgacttga aatctgcact cgaagaatta aataatgtat ttacaaacaa agaagctcaa   600
gaggaaagca gtccaatagg cgaccatggg acattcttta gaaattgtt  aacacatgtt   660 agaacaatta aagaaaatga agatatagaa aataaaggag aaacacttat attaggcgat   720
aataaaatag atgtaatgaa ttcaaacgat ttctttttta caaccaactc aaatgtaaaa   780
```

```
tttatggaaa atttagatga tataacaaat caatatggat taggtttgat taatcatcta      840
ggtcctcatt taatagcctt gggtcatttt accgtattaa aattagcact aaaaaattac      900
aaaaactatt ttgaagcaaa aagtattaaa tttttttagtt ggcaaaaaat tttagagttc      960
tccatgtctg atagatttaa agttcttgat atgatgtgtg accatgaatc tgtatactat     1020
tccgaaaaaa aacgtagaaa aacatattta aaagttgaca gatcaaatac atctatggaa     1080
tgtaatatat tggaatattt attacattat tttaataaat accaactaga aataattaaa     1140
actacacaag atactgattt tgacttacat ggtatgatgg aacataaata tataaaagat     1200
tatttctttt catttatgtg taatgatcct aaagaatgta ttatttatca tacgaatcaa     1260
tttaaaaaag aagccaacga agaaaacaca tttcctgaac aagaagaacc taaccgtcaa     1320
ataagtgcat ttaatttata tttaaattat tattatttca tgaaacgtta tagttcatat     1380
ggagtaaaaa agacattata tgttcattta ttaaatttaa ctggactttt aaattatgat     1440
acaagagcat acgtgacatc actttatttta ccaggatatt acaacgctgt cgaaatgtct     1500
tttacggaag aaaaagagtt ttccaaactt tttgaaagct taatacaatg tattgaaaaa     1560
tgccattcag accaagcaag gcaaatatca aaagatagta atttacttaa taatataaca     1620
aaatgtgatt tgtgtaaagg agcctttttta tatgctaata tgaaattcga tgaagttcct     1680
tcaatgttgc aaaaattttta cgtatattta actaaaggtc tcaaaataca aaaagtatca     1740
tcactaatca aaacgctaga tatatatcaa gattacagca attacttatc acatgatatt     1800
aattggtaca cattcctatt tttatttaga cttacaagtt ttaaagaaat tgcaaagaaa     1860
aatgttgctg aagcaatgta tttaaatata aaagatgaag acacattcaa caaaacggta     1920
gtaacaaact attggtaccc atctcctata aaaaaatatt atacattata tgttagaaaa     1980
catataccaa ataatttagt agatgaattg gagaaattaa tgaaaagtgg cactttagaa     2040
aaaatgaaaa aatctctcac cttttttagta catgtgaatt cattttttaca attagatttt     2100 ttccatcaat taaatgaacc acctcttgga ttacctcgat catatccatt atcgttagtt     2160
ctcgaacata aatttaaaga atggatgaac agttcgccag caggtttcta ttttttcaaat     2220 tatcaaaatc catatatcag aaaagatttg catgataaag ttttatcaca aaaatttgaa     2280
ccacctaaaa tgaatcagtg gaacaaagtt ttgaaatcat taattgaatg cgcatatgat     2340
atgtattttg aacagagaca tgttaaaaat ttatataaat atcataacat ttataatata     2400
aataacaaat taatgttaat gcgagattca atcgatttgt ataaaaacaa ttttgacgat     2460
gtgttatttt ttgcggatat atttaatatg agaaaatata tgacagctac accagtatat     2520
aaaaaagtaa aagacagagt gtaccataca ttgcatagta ttacaggaaa ttctgtcaat     2580
ttttataaat atggtattat atatggattt aaagtaaaca aagaaatatt aaagaagtt      2640 gtcgatgaat tgtattccat ctataatttt aacaccgaca tatttacgga tacttccttt     2700
ttacaaaccg tttatttatt atttagaaga atagaagaaa cctataggac caaagaaga      2760 gatgataaaa ttagtgtgaa taacgttttt ttcatgaatg ttgctaataa ttattccaaa     2820
ttaaacaaag aagaaagaga aatcgaaata cataattcca tggcatcaag atattatgca     2880
aaaacgatgt ttgcagcatt tcaaatgtta ttttcaacaa tgttgagcaa caatgtagat     2940
aatcttgata agcatatgg attaagtgaa aatatccaag tagcaacaag tacttccgct     3000
tttcttactt ttgcatatgt atataacgga agtataatgg atagtgtgac taacagttta     3060
ttgccaccat atgcgaagaa acctataaca caattaaaat atggaaaaac cttcgttttc     3120
```

-continued

```
tcaaactatt tcatgctagc atccaaaatg tatgatatgt taaattataa aaatttaagt    3180
cttttatgtg aatatcaggc tgtggcaagt gccaatttct actctgctaa aaaggtaggt    3240
cagtttcttg gaagaaaatt tttacccata actacatatt ttctagtaat gagaattagt    3300
tggacacatg cttttacaac tggacaacat ttgattagcg cttttggttc cccaagttct    3360
actgctaatg gtaaaagtaa tgctagtggt tataaatccc ctgaaagttt tttcttcact    3420
cacggacttg ctgctgaagc atccaaatat ttatttttt attttttcac aaatttatac    3480
cttgatgcct acaaatcttt tcctggagga tttggtcctg caataaaaga acaaactcaa    3540
catgttcaag aacaaaccta cgaacgcaaa ccgtcagttc atagttttaa tagaaatttt    3600
ttcatggaac tcgtaaatgg attcatgtat gccttttgtt tttttgcaat ttctcaaatg    3660
tatgcatatt ttgaaaatat taattttat attacaagta atttccgttt cttggataga    3720
tattatggtg tattcaataa atattttata aactatgcca taattaaact taagaaaatt    3780
actagtgatc ttttaataaa atatgaacgt gaggcttatt taagtatgaa aaaatatggt    3840
tatttaggtg aagttattgc agctagactt tctccaaaag ataaaattat gaattatgtg    3900
cacgaaacta acgaagatat catgagtaat ttaagaagat atgatatgga aaatgctttc    3960
aaaaacaaaa tgtcaacata tgtagatgat tttgcttttt ttgatgattg cggaaaaaat    4020
gaacaatttt taaatgagag atgtgattat tgtcctgtaa ttgaagaggt cgaagaaaca    4080
caattattta ctaccactgg tgataaaaac actaataaga ccacggaaat aaaaaaacaa    4140
actagtacat atattgatac tgaaaaaatg aatgaagcgg attctgctga tagcgacgat    4200
gaaaaggatt ctgatactcc tgacgatgaa ttaatgatat cacgatttca ctaa         4254
```

<210> SEQ ID NO 2
<211> LENGTH: 1417
<212> TYPE: PRT
<213> ORGANISM: Plasmodium falciparum

<400> SEQUENCE: 2

```
Met Val Ser Phe Phe Lys Thr Pro Ile Phe Ile Leu Ile Ile Phe Leu
1               5                   10                  15

Tyr Leu Asn Glu Lys Val Ile Cys Ser Ile Asn Glu Asn Gln Asn Glu
            20                  25                  30

Asn Asp Thr Ile Ser Gln Asn Val Asn Gln His Glu Asn Ile Asn Gln
        35                  40                  45

Asn Val Asn Asp Asn Asp Asn Ile Glu Gln Leu Lys Ser Met Ile Gly
    50                  55                  60

Asn Asp Glu Leu His Lys Asn Leu Thr Ile Leu Glu Lys Leu Ile Leu
65                  70                  75                  80

Glu Ser Leu Glu Lys Asp Lys Leu Lys Tyr Pro Leu Leu Lys Gln Gly
                85                  90                  95

Thr Glu Gln Leu Ile Asp Ile Ser Lys Phe Asn Lys Lys Asn Ile Thr
            100                 105                 110

Asp Ala Asp Asp Glu Thr Tyr Ile Ile Pro Thr Val Gln Ser Thr Phe
        115                 120                 125

His Asp Ile Val Lys Tyr Glu His Leu Ile Lys Glu Gln Ser Ile Glu
    130                 135                 140

Ile Tyr Asn Ser Asp Ile Ser Asp Lys Ile Lys Lys Ile Phe Ile
145                 150                 155                 160

Val Arg Thr Leu Lys Thr Ile Lys Leu Met Leu Ile Pro Leu Asn Ser
                165                 170                 175
```

```
Tyr Lys Gln Asn Asn Asp Leu Lys Ser Ala Leu Glu Glu Leu Asn Asn
            180                 185                 190

Val Phe Thr Asn Lys Glu Ala Gln Glu Glu Ser Ser Pro Ile Gly Asp
            195                 200             205

His Gly Thr Phe Phe Arg Lys Leu Leu Thr His Val Arg Thr Ile Lys
        210                 215                 220

Glu Asn Glu Asp Ile Glu Asn Lys Gly Glu Thr Leu Ile Leu Gly Asp
225                 230                 235                 240

Asn Lys Ile Asp Val Met Asn Ser Asn Asp Phe Phe Thr Thr Asn
                245                 250                 255

Ser Asn Val Lys Phe Met Glu Asn Leu Asp Asp Ile Thr Asn Gln Tyr
            260                 265                 270

Gly Leu Gly Leu Ile Asn His Leu Gly Pro His Leu Ile Ala Leu Gly
        275                 280                 285

His Phe Thr Val Leu Lys Leu Ala Leu Lys Asn Tyr Lys Asn Tyr Phe
    290                 295                 300

Glu Ala Lys Ser Ile Lys Phe Phe Ser Trp Gln Lys Ile Leu Glu Phe
305                 310                 315                 320

Ser Met Ser Asp Arg Phe Lys Val Leu Asp Met Met Cys Asp His Glu
                325                 330                 335

Ser Val Tyr Tyr Ser Glu Lys Lys Arg Arg Lys Thr Tyr Leu Lys Val
            340                 345                 350

Asp Arg Ser Asn Thr Ser Met Glu Cys Asn Ile Leu Glu Tyr Leu Leu
        355                 360                 365

His Tyr Phe Asn Lys Tyr Gln Leu Glu Ile Ile Lys Thr Thr Gln Asp
    370                 375                 380

Thr Asp Phe Asp Leu His Gly Met Met Glu His Lys Tyr Ile Lys Asp
385                 390                 395                 400

Tyr Phe Phe Ser Phe Met Cys Asn Asp Pro Lys Glu Cys Ile Ile Tyr
                405                 410                 415

His Thr Asn Gln Phe Lys Lys Glu Ala Asn Glu Glu Asn Thr Phe Pro
            420                 425                 430

Glu Gln Glu Glu Pro Asn Arg Gln Ile Ser Ala Phe Asn Leu Tyr Leu
        435                 440                 445

Asn Tyr Tyr Tyr Phe Met Lys Arg Tyr Ser Ser Tyr Gly Val Lys Lys
    450                 455                 460

Thr Leu Tyr Val His Leu Leu Asn Leu Thr Gly Leu Leu Asn Tyr Asp
465                 470                 475                 480

Thr Arg Ala Tyr Val Thr Ser Leu Tyr Leu Pro Gly Tyr Tyr Asn Ala
                485                 490                 495

Val Glu Met Ser Phe Thr Glu Glu Lys Glu Phe Ser Lys Leu Phe Glu
            500                 505                 510

Ser Leu Ile Gln Cys Ile Glu Lys Cys His Ser Asp Gln Ala Arg Gln
        515                 520                 525

Ile Ser Lys Asp Ser Asn Leu Leu Asn Asn Ile Thr Lys Cys Asp Leu
    530                 535                 540

Cys Lys Gly Ala Phe Leu Tyr Ala Asn Met Lys Phe Asp Glu Val Pro
545                 550                 555                 560

Ser Met Leu Gln Lys Phe Val Tyr Leu Thr Lys Gly Leu Lys Ile
                565                 570                 575

Gln Lys Val Ser Ser Leu Ile Lys Thr Leu Asp Ile Tyr Gln Asp Tyr
            580                 585                 590

Ser Asn Tyr Leu Ser His Asp Ile Asn Trp Tyr Thr Phe Leu Phe Leu
```

```
                    595                 600                 605
        Phe Arg Leu Thr Ser Phe Lys Glu Ile Ala Lys Lys Asn Val Ala Glu
        610                 615                 620

Ala Met Tyr Leu Asn Ile Lys Asp Glu Asp Thr Phe Asn Lys Thr Val
        625                 630                 635                 640

Val Thr Asn Tyr Trp Tyr Pro Ser Pro Ile Lys Lys Tyr Tyr Thr Leu
                        645                 650                 655

Tyr Val Arg Lys His Ile Pro Asn Asn Leu Val Asp Glu Leu Glu Lys
                        660                 665                 670

Leu Met Lys Ser Gly Thr Leu Glu Lys Met Lys Lys Ser Leu Thr Phe
                        675                 680                 685

Leu Val His Val Asn Ser Phe Leu Gln Leu Asp Phe Phe His Gln Leu
        690                 695                 700

Asn Glu Pro Pro Leu Gly Leu Pro Arg Ser Tyr Pro Leu Ser Leu Val
        705                 710                 715                 720

Leu Glu His Lys Phe Lys Glu Trp Met Asn Ser Ser Pro Ala Gly Phe
                        725                 730                 735

Tyr Phe Ser Asn Tyr Gln Asn Pro Tyr Ile Arg Lys Asp Leu His Asp
                        740                 745                 750

Lys Val Leu Ser Gln Lys Phe Glu Pro Pro Lys Met Asn Gln Trp Asn
                        755                 760                 765

Lys Val Leu Lys Ser Leu Ile Glu Cys Ala Tyr Asp Met Tyr Phe Glu
        770                 775                 780

Gln Arg His Val Lys Asn Leu Tyr Lys Tyr His Asn Ile Tyr Asn Ile
        785                 790                 795                 800

Asn Asn Lys Leu Met Leu Met Arg Asp Ser Ile Asp Leu Tyr Lys Asn
                        805                 810                 815

Asn Phe Asp Asp Val Leu Phe Phe Ala Asp Ile Phe Asn Met Arg Lys
                        820                 825                 830

Tyr Met Thr Ala Thr Pro Val Tyr Lys Lys Val Lys Asp Arg Val Tyr
                        835                 840                 845

His Thr Leu His Ser Ile Thr Gly Asn Ser Val Asn Phe Tyr Lys Tyr
        850                 855                 860

Gly Ile Ile Tyr Gly Phe Lys Val Asn Lys Glu Ile Leu Lys Glu Val
        865                 870                 875                 880

Val Asp Glu Leu Tyr Ser Ile Tyr Asn Phe Asn Thr Asp Ile Phe Thr
                        885                 890                 895

Asp Thr Ser Phe Leu Gln Thr Val Tyr Leu Leu Phe Arg Arg Ile Glu
                        900                 905                 910

Glu Thr Tyr Arg Thr Gln Arg Arg Asp Asp Lys Ile Ser Val Asn Asn
                        915                 920                 925

Val Phe Phe Met Asn Val Ala Asn Asn Tyr Ser Lys Leu Asn Lys Glu
                        930                 935                 940

Glu Arg Glu Ile Glu Ile His Asn Ser Met Ala Ser Arg Tyr Tyr Ala
        945                 950                 955                 960

Lys Thr Met Phe Ala Ala Phe Gln Met Leu Phe Ser Thr Met Leu Ser
                        965                 970                 975

Asn Asn Val Asp Asn Leu Asp Lys Ala Tyr Gly Leu Ser Glu Asn Ile
                        980                 985                 990

Gln Val Ala Thr Ser Thr Ser Ala  Phe Leu Thr Phe Ala  Tyr Val Tyr
                        995                 1000                1005

Asn Gly  Ser Ile Met Asp Ser  Val Thr Asn Ser Leu  Leu Pro Pro
                        1010                1015                1020
```

```
Tyr Ala Lys Lys Pro Ile Thr Gln Leu Lys Tyr Gly Lys Thr Phe
1025                1030                1035

Val Phe Ser Asn Tyr Phe Met Leu Ala Ser Lys Met Tyr Asp Met
1040                1045                1050

Leu Asn Tyr Lys Asn Leu Ser Leu Leu Cys Glu Tyr Gln Ala Val
1055                1060                1065

Ala Ser Ala Asn Phe Tyr Ser Ala Lys Lys Val Gly Gln Phe Leu
1070                1075                1080

Gly Arg Lys Phe Leu Pro Ile Thr Thr Tyr Phe Leu Val Met Arg
1085                1090                1095

Ile Ser Trp Thr His Ala Phe Thr Thr Gly Gln His Leu Ile Ser
1100                1105                1110

Ala Phe Gly Ser Pro Ser Ser Thr Ala Asn Gly Lys Ser Asn Ala
1115                1120                1125

Ser Gly Tyr Lys Ser Pro Glu Ser Phe Phe Thr His Gly Leu
1130                1135                1140

Ala Ala Glu Ala Ser Lys Tyr Leu Phe Phe Tyr Phe Phe Thr Asn
1145                1150                1155

Leu Tyr Leu Asp Ala Tyr Lys Ser Phe Pro Gly Gly Phe Gly Pro
1160                1165                1170

Ala Ile Lys Glu Gln Thr Gln His Val Gln Glu Gln Thr Tyr Glu
1175                1180                1185

Arg Lys Pro Ser Val His Ser Phe Asn Arg Asn Phe Phe Met Glu
1190                1195                1200

Leu Val Asn Gly Phe Met Tyr Ala Phe Cys Phe Phe Ala Ile Ser
1205                1210                1215

Gln Met Tyr Ala Tyr Phe Glu Asn Ile Asn Phe Tyr Ile Thr Ser
1220                1225                1230

Asn Phe Arg Phe Leu Asp Arg Tyr Tyr Gly Val Phe Asn Lys Tyr
1235                1240                1245

Phe Ile Asn Tyr Ala Ile Ile Lys Leu Lys Glu Ile Thr Ser Asp
1250                1255                1260

Leu Leu Ile Lys Tyr Glu Arg Glu Ala Tyr Leu Ser Met Lys Lys
1265                1270                1275

Tyr Gly Tyr Leu Gly Glu Val Ile Ala Ala Arg Leu Ser Pro Lys
1280                1285                1290

Asp Lys Ile Met Asn Tyr Val His Glu Thr Asn Glu Asp Ile Met
1295                1300                1305

Ser Asn Leu Arg Arg Tyr Asp Met Glu Asn Ala Phe Lys Asn Lys
1310                1315                1320

Met Ser Thr Tyr Val Asp Asp Phe Ala Phe Phe Asp Asp Cys Gly
1325                1330                1335

Lys Asn Glu Gln Phe Leu Asn Glu Arg Cys Asp Tyr Cys Pro Val
1340                1345                1350

Ile Glu Glu Val Glu Glu Thr Gln Leu Phe Thr Thr Thr Gly Asp
1355                1360                1365

Lys Asn Thr Asn Lys Thr Thr Glu Ile Lys Lys Gln Thr Ser Thr
1370                1375                1380

Tyr Ile Asp Thr Glu Lys Met Asn Glu Ala Asp Ser Ala Asp Ser
1385                1390                1395

Asp Asp Glu Lys Asp Ser Asp Thr Pro Asp Asp Glu Leu Met Ile
1400                1405                1410
```

Ser Arg Phe His
    1415

<210> SEQ ID NO 3
<211> LENGTH: 4251
<212> TYPE: DNA
<213> ORGANISM: Plasmodium falciparum

<400> SEQUENCE: 3

| | | | | | |
|---|---|---|---|---|---|
| atggtttcat | ttttaagac | tccgatcatt | attttttttt | tcctcttatg | tttaaatgaa | 60 |
| aaggtattat | gttcaataaa | tgaaaatgaa | aatttaggcg | aaaataaaaa | cgaaaatgca | 120 |
| aatgtaaaca | cacctgaaaa | tttaaataaa | cttctaaatg | agtatgacaa | tattgaacaa | 180 |
| ttaaaatcca | tgataggaaa | tgatgaacta | cataagaatt | taacaatatt | agaaaaatta | 240 |
| attttagagt | ctctagaaaa | agataaatta | aaatatcctc | tccttaaaca | aggaactgaa | 300 |
| caattgatag | atatatcaaa | atttaataaa | aaaaatatta | cagatgcgga | tgatgaaacg | 360 |
| tacatcatac | ctaccgtcca | atcaagcttt | cacgatattg | taaatatgaa | acatcttata | 420 |
| aaagaacaat | caatagaaat | ttataattct | gatatatcag | ataaaattaa | gaaaaaaata | 480 |
| tttattgtaa | gaacattgaa | acaataaaa | ttaatgctta | taccattaaa | ttcatacaaa | 540 |
| caaaataatg | atttgaaatc | tgcgctcgaa | gaattaaata | atgtatttac | aaacaaagaa | 600 |
| gctcaaaagg | aaagcagtcc | aataggcgac | catgggacat | tctttagaaa | attgttaaca | 660 |
| catgttagaa | caattaaaga | aaatgaagat | atagaaaata | aaggagaaac | acttatatta | 720 |
| ggcgataata | aaatagatgt | aatgaattca | aacgatttct | tttttacaac | caactcaaat | 780 |
| gtaaaattta | tggaaaattt | agatgatata | acaaatcaat | atggattagg | tttgattaat | 840 |
| catttgggtc | ctcatttaat | agccttggga | cattttgttg | tattaaaatt | agcactaaaa | 900 |
| aattacaaaa | attattttga | agcaaaaaat | ataaatttt | ttagttggca | aaaaatttta | 960 |
| gagttctcca | tgtctgatag | atttaaggtt | cttgatatga | tgtgtaacca | tgaatctgta | 1020 |
| tattattccg | aaaaaaaacg | tagaaagaca | tatttaaaag | tcgacagatc | aagcacatct | 1080 |
| atggaatgta | atatattgga | atatttatta | cattatttta | ataaatacca | actagaaata | 1140 |
| attaaaacta | cacaagatac | agatttcgat | ttacatggta | tgatggaaca | taaatatata | 1200 |
| aaagattatt | tcttttcatt | tatgtgtaac | gatcctaaag | aatgtattat | ttatcatacg | 1260 |
| aatcaattta | aaaagaaagc | taacgaagaa | aacactttc | ctgaacaaga | agaacctaac | 1320 |
| cgtcaaataa | gtgcatttaa | tttatattta | aattattatt | atttcatgaa | acgttatagt | 1380 |
| tcatatggaa | caaaaaaaac | attatatgtt | catttattaa | atttaactgg | acttttaaac | 1440 |
| catgatacaa | gagcatacgt | gacatcccctt | tatttaccag | atattacaa | cgctgtcgaa | 1500 |
| atgtctttta | cggacgataa | agagttttcc | acacttttg | aaagcttaat | acaatgtatt | 1560 |
| gaaaaatgcc | attcagacca | agcaaggcaa | atatcaaaag | atagtaattt | acttaataat | 1620 |
| ataacaaaat | gtgatttgtg | taaaggagcc | ttttatatg | ctaatatgaa | attcgatgaa | 1680 |
| gttccttcaa | tgttgcaaaa | attttacgta | tatttaacta | aaggtctcaa | aatacaaaaa | 1740 |
| gtatcatcac | taatcaaaac | gctagatata | tatcaagatt | acagtaattt | cttatcacat | 1800 |
| gatattaatt | ggtacacatt | cctattttta | tttagactta | caagttttaa | agaaattgca | 1860 |
| aataaaaatg | ttgctgaagc | aatgtattta | aatataaaag | atgaagacac | attcaacaaa | 1920 |
| acgatagtaa | caaactattg | gtacccatct | cctataaaaa | aatattatac | attatatgtt | 1980 |
| agaaaacata | taccaaataa | tttagtagat | gaattagaga | aattaatgaa | aagtggcact | 2040 |

```
ttagaaaaaa tgaaaaaatc tctcaccttt ttagtacatg tgaattcatt tttacaatta      2100
gattttttcc atcaattaaa tgaaccacct cttggattac ctcgatcata tccattatcg      2160
ttagttctcg aacataaatt taaagaatgg atggacagtt cgccagcagg tttctatttt      2220
tcaaattatc aaaatccata tatcagaaaa gatttgcatg ataaagtttt atcacaaaaa      2280
tttgaaccac ctaaaatgaa tcagtggaac aaagttttga atcattaat tgaatgcgca       2340 tatgatatgt attttgaaca gagacatgtt aaaaatttat ataaatatca taacattttat     2400 aatataaata acaaattaat gttaatgcga gattcaatcg atttgtataa aaacaatttt     2460
gacgatgtgt tattttttgc ggatatattt aaatgagaa atatatgac agctacacca      2520 gtatataaaa aagtaaaaga ccgagtgtac catacattgc atagtattac aggaaattct     2580
gtcaattttt ataaatatgg tattatatat ggatttaaag taaacaaaga aatattaaaa    2640
gaagttgtcg atgaattgta ttccatctat aattttaaca ccgacatatt tacggatact    2700 tccttttttac aaaccgttta tttattattt agaagaatag aagaaaccta taggacccaa   2760
agaagagatg ataaaattag tgtgaataac gttttttttca tgaatgttgc taataattat    2820
tccaaattaa acaagaaga aagagaaatc gaaatacata attccatggc atcaagatat      2880
tatgcaaaaa cgatgtttgc agcatttcaa atgttatttt caacaatgtt gagcaacaat    2940
gtagataatc ttgataaagc atatggatta agtgaaaata tccaagtagc aacaagtact    3000
tccgcttttc ttactttttgc atatgtatat aacggaagta aatgagatag tgtgactaac   3060
agtttattgc caccatatgc gaagaaacct ataacacaat taaaatatgg aaaaaaccttc    3120 gttttctcaa actatttcat gctagcatcc aaaatgtatg atatgttaaa ttataaaaat    3180
ttaagtcttt tatgtgaata tcaggctgtg gcaagtgcca atttctactc tgctaaaaag    3240
gtaggtcagt ttcttggaag aaaattttta cccataacta catattttct agtaatgaga    3300
attagttgga cacatgcttt tacaactgga caacatttga tttgcgcttt tgatcccaaa    3360
agatgtactc ctgattgtaa aaatagtact agttataaat ctcctcaaag ttttttttttac  3420 ggttggcctc ctagttcaga aacatatttg ttcttttatt ttttcacaaa tttataccctt   3480 gatgcctata aatctttcc tggaggattt ggtcctgcaa taaagaaca aactcaacat     3540 gttcaagaac aaacctacga acgcaaaccg tcagttcata gttttaatag aaatttttc     3600 atggaactcg taaatggatt catgtatgcc ttttgttttt ttgcaatttc tcaaatgtat    3660
gcatattttg aaaatattaa ttttttatatt acaagtaatt tccgtttctt ggatagatat   3720
tatggtgtat tcaataaata ttttataaac tatgccataa ttaaacttaa agaaattact   3780
agtgatcttt taataaaata tgaacgtgag gcttatttaa gtatgaaaaa atatggttat    3840
ttaggtgaag ttattgcagc tagacttttct ccaaaagata aaattatgaa ttatgtgcac   3900
gaaactaacg aagatatcat gagtaattta agaagatatg atatggaaaa tgctttcaaa   3960
aacaaaatgg ttacttatgt ggatgacttt gcttttttg atgattgtgg caaaaatgaa    4020
caatttttaa atgaaagatg tgattattgc cctgtaattg aagaggtgga agaaacacaa   4080
ttatttacta cccactggtga taaaaatact aatgagacca cggaaataaa aaaacaaact   4140
agtacatata ttgatactga aaaaatgaat gaagcggatt ctgctgatag cgacgatgaa    4200
aaggattttg atactcctga caatgaatta atgatcgcac gatttcatta a            4251
```

<210> SEQ ID NO 4
<211> LENGTH: 1416
<212> TYPE: PRT
<213> ORGANISM: Plasmodium falciparum

<400> SEQUENCE: 4

```
Met Val Ser Phe Phe Lys Thr Pro Ile Ile Ile Phe Phe Leu Leu
1               5                   10                  15

Cys Leu Asn Glu Lys Val Leu Cys Ser Ile Asn Glu Asn Glu Asn Leu
            20                  25                  30

Gly Glu Asn Lys Asn Glu Asn Ala Asn Val Asn Thr Pro Glu Asn Leu
            35                  40                  45

Asn Lys Leu Leu Asn Glu Tyr Asp Asn Ile Glu Gln Leu Lys Ser Met
        50                  55                  60

Ile Gly Asn Asp Glu Leu His Lys Asn Leu Thr Ile Leu Glu Lys Leu
65                  70                  75                  80

Ile Leu Glu Ser Leu Glu Lys Asp Lys Leu Lys Tyr Pro Leu Leu Lys
                85                  90                  95

Gln Gly Thr Glu Gln Leu Ile Asp Ile Ser Lys Phe Asn Lys Lys Asn
            100                 105                 110

Ile Thr Asp Ala Asp Asp Glu Thr Tyr Ile Ile Pro Thr Val Gln Ser
        115                 120                 125

Ser Phe His Asp Ile Val Lys Tyr Glu His Leu Ile Lys Glu Gln Ser
    130                 135                 140

Ile Glu Ile Tyr Asn Ser Asp Ile Ser Asp Lys Ile Lys Lys Ile
145                 150                 155                 160

Phe Ile Val Arg Thr Leu Lys Thr Ile Lys Leu Met Leu Ile Pro Leu
                165                 170                 175

Asn Ser Tyr Lys Gln Asn Asn Asp Leu Lys Ser Ala Leu Glu Glu Leu
            180                 185                 190

Asn Asn Val Phe Thr Asn Lys Glu Ala Gln Lys Glu Ser Ser Pro Ile
            195                 200                 205

Gly Asp His Gly Thr Phe Phe Arg Lys Leu Leu Thr His Val Arg Thr
    210                 215                 220

Ile Lys Glu Asn Glu Asp Ile Glu Asn Lys Gly Glu Thr Leu Ile Leu
225                 230                 235                 240

Gly Asp Asn Lys Ile Asp Val Met Asn Ser Asn Asp Phe Phe Phe Thr
                245                 250                 255

Thr Asn Ser Asn Val Lys Phe Met Glu Asn Leu Asp Asp Ile Thr Asn
            260                 265                 270

Gln Tyr Gly Leu Gly Leu Ile Asn His Leu Gly Pro His Leu Ile Ala
        275                 280                 285

Leu Gly His Phe Val Val Leu Lys Leu Ala Leu Lys Asn Tyr Lys Asn
    290                 295                 300

Tyr Phe Glu Ala Lys Asn Ile Lys Phe Phe Ser Trp Gln Lys Ile Leu
305                 310                 315                 320

Glu Phe Ser Met Ser Asp Arg Phe Lys Val Leu Asp Met Met Cys Asn
                325                 330                 335

His Glu Ser Val Tyr Tyr Ser Glu Lys Lys Arg Arg Lys Thr Tyr Leu
            340                 345                 350

Lys Val Asp Arg Ser Ser Thr Ser Met Glu Cys Asn Ile Leu Glu Tyr
        355                 360                 365

Leu Leu His Tyr Phe Asn Lys Tyr Gln Leu Glu Ile Ile Lys Thr Thr
    370                 375                 380

Gln Asp Thr Asp Phe Asp Leu His Gly Met Met Glu His Lys Tyr Ile
385                 390                 395                 400

Lys Asp Tyr Phe Phe Ser Phe Met Cys Asn Asp Pro Lys Glu Cys Ile
```

```
                405                 410                 415
Ile Tyr His Thr Asn Gln Phe Lys Lys Glu Ala Asn Glu Asn Thr
                420                 425                 430

Phe Pro Glu Gln Glu Glu Pro Asn Arg Gln Ile Ser Ala Phe Asn Leu
                435                 440                 445

Tyr Leu Asn Tyr Tyr Tyr Phe Met Lys Arg Tyr Ser Ser Tyr Gly Thr
                450                 455                 460

Lys Lys Thr Leu Tyr Val His Leu Leu Asn Leu Thr Gly Leu Leu Asn
465                 470                 475                 480

His Asp Thr Arg Ala Tyr Val Thr Ser Leu Tyr Leu Pro Gly Tyr Tyr
                485                 490                 495

Asn Ala Val Glu Met Ser Phe Thr Asp Lys Glu Phe Ser Thr Leu
                500                 505                 510

Phe Glu Ser Leu Ile Gln Cys Ile Glu Lys Cys His Ser Asp Gln Ala
                515                 520                 525

Arg Gln Ile Ser Lys Asp Ser Asn Leu Leu Asn Asn Ile Thr Lys Cys
                530                 535                 540

Asp Leu Cys Lys Gly Ala Phe Leu Tyr Ala Asn Met Lys Phe Asp Glu
545                 550                 555                 560

Val Pro Ser Met Leu Gln Lys Phe Tyr Val Tyr Leu Thr Lys Gly Leu
                565                 570                 575

Lys Ile Gln Lys Val Ser Ser Leu Ile Lys Thr Leu Asp Ile Tyr Gln
                580                 585                 590

Asp Tyr Ser Asn Phe Leu Ser His Asp Ile Asn Trp Tyr Thr Phe Leu
                595                 600                 605

Phe Leu Phe Arg Leu Thr Ser Phe Lys Glu Ile Ala Asn Lys Asn Val
                610                 615                 620

Ala Glu Ala Met Tyr Leu Asn Ile Lys Asp Glu Asp Thr Phe Asn Lys
625                 630                 635                 640

Thr Ile Val Thr Asn Tyr Trp Tyr Pro Ser Pro Ile Lys Lys Tyr Tyr
                645                 650                 655

Thr Leu Tyr Val Arg Lys His Ile Pro Asn Asn Leu Val Asp Glu Leu
                660                 665                 670

Glu Lys Leu Met Lys Ser Gly Thr Leu Glu Lys Met Lys Lys Ser Leu
                675                 680                 685

Thr Phe Leu Val His Val Asn Ser Phe Leu Gln Leu Asp Phe His
                690                 695                 700

Gln Leu Asn Glu Pro Pro Leu Gly Leu Pro Arg Ser Tyr Pro Leu Ser
705                 710                 715                 720

Leu Val Leu Glu His Lys Phe Lys Glu Trp Met Asp Ser Ser Pro Ala
                725                 730                 735

Gly Phe Tyr Phe Ser Asn Tyr Gln Asn Pro Tyr Ile Arg Lys Asp Leu
                740                 745                 750

His Asp Lys Val Leu Ser Gln Lys Phe Glu Pro Pro Lys Met Asn Gln
                755                 760                 765

Trp Asn Lys Val Leu Lys Ser Leu Ile Glu Cys Ala Tyr Asp Met Tyr
                770                 775                 780

Phe Glu Gln Arg His Val Lys Asn Leu Tyr Lys Tyr His Asn Ile Tyr
785                 790                 795                 800

Asn Ile Asn Asn Lys Leu Met Leu Met Arg Asp Ser Ile Asp Leu Tyr
                805                 810                 815

Lys Asn Asn Phe Asp Asp Val Leu Phe Phe Ala Asp Ile Phe Asn Met
                820                 825                 830
```

```
Arg Lys Tyr Met Thr Ala Thr Pro Val Tyr Lys Lys Val Lys Asp Arg
        835                 840                 845

Val Tyr His Thr Leu His Ser Ile Thr Gly Asn Ser Val Asn Phe Tyr
850                 855                 860

Lys Tyr Gly Ile Ile Tyr Gly Phe Lys Val Asn Lys Glu Ile Leu Lys
865                 870                 875                 880

Glu Val Val Asp Glu Leu Tyr Ser Ile Tyr Asn Phe Asn Thr Asp Ile
                885                 890                 895

Phe Thr Asp Thr Ser Phe Leu Gln Thr Val Tyr Leu Leu Phe Arg Arg
            900                 905                 910

Ile Glu Glu Thr Tyr Arg Thr Gln Arg Arg Asp Asp Lys Ile Ser Val
        915                 920                 925

Asn Asn Val Phe Phe Met Asn Val Ala Asn Asn Tyr Ser Lys Leu Asn
    930                 935                 940

Lys Glu Glu Arg Glu Ile Glu Ile His Asn Ser Met Ala Ser Arg Tyr
945                 950                 955                 960

Tyr Ala Lys Thr Met Phe Ala Ala Phe Gln Met Leu Phe Ser Thr Met
                965                 970                 975

Leu Ser Asn Asn Val Asp Asn Leu Asp Lys Ala Tyr Gly Leu Ser Glu
            980                 985                 990

Asn Ile Gln Val Ala Thr Ser Thr Ser Ala Phe Leu Thr Phe Ala Tyr
        995                 1000                1005

Val Tyr Asn Gly Ser Ile Met Asp Ser Val Thr Asn Ser Leu Leu
    1010                1015                1020

Pro Pro Tyr Ala Lys Lys Pro Ile Thr Gln Leu Lys Tyr Gly Lys
1025                1030                1035

Thr Phe Val Phe Ser Asn Tyr Phe Met Leu Ala Ser Lys Met Tyr
    1040                1045                1050

Asp Met Leu Asn Tyr Lys Asn Leu Ser Leu Leu Cys Glu Tyr Gln
1055                1060                1065

Ala Val Ala Ser Ala Asn Phe Tyr Ser Ala Lys Lys Val Gly Gln
    1070                1075                1080

Phe Leu Gly Arg Lys Phe Leu Pro Ile Thr Thr Tyr Phe Leu Val
1085                1090                1095

Met Arg Ile Ser Trp Thr His Ala Phe Thr Thr Gly Gln His Leu
    1100                1105                1110

Ile Cys Ala Phe Asp Pro Lys Arg Cys Thr Pro Asp Cys Lys Asn
1115                1120                1125

Ser Thr Ser Tyr Lys Ser Pro Gln Ser Phe Phe Tyr Gly Trp Pro
    1130                1135                1140

Pro Ser Ser Glu Thr Tyr Leu Phe Phe Tyr Phe Phe Thr Asn Leu
1145                1150                1155

Tyr Leu Asp Ala Tyr Lys Ser Phe Pro Gly Gly Phe Gly Pro Ala
    1160                1165                1170

Ile Lys Glu Gln Thr Gln His Val Gln Glu Gln Thr Tyr Glu Arg
1175                1180                1185

Lys Pro Ser Val His Ser Phe Asn Arg Asn Phe Phe Met Glu Leu
    1190                1195                1200

Val Asn Gly Phe Met Tyr Ala Phe Cys Phe Phe Ala Ile Ser Gln
1205                1210                1215

Met Tyr Ala Tyr Phe Glu Asn Ile Asn Phe Tyr Ile Thr Ser Asn
    1220                1225                1230
```

```
Phe Arg Phe Leu Asp Arg Tyr Tyr Gly Val Phe Asn Lys Tyr Phe
    1235                1240                1245

Ile Asn Tyr Ala Ile Ile Lys Leu Lys Glu Ile Thr Ser Asp Leu
    1250                1255                1260

Leu Ile Lys Tyr Glu Arg Glu Ala Tyr Leu Ser Met Lys Lys Tyr
    1265                1270                1275

Gly Tyr Leu Gly Glu Val Ile Ala Ala Arg Leu Ser Pro Lys Asp
    1280                1285                1290

Lys Ile Met Asn Tyr Val His Glu Thr Asn Glu Asp Ile Met Ser
    1295                1300                1305

Asn Leu Arg Arg Tyr Asp Met Glu Asn Ala Phe Lys Asn Lys Met
    1310                1315                1320

Val Thr Tyr Val Asp Asp Phe Ala Phe Phe Asp Asp Cys Gly Lys
    1325                1330                1335

Asn Glu Gln Phe Leu Asn Glu Arg Cys Asp Tyr Cys Pro Val Ile
    1340                1345                1350

Glu Glu Val Glu Glu Thr Gln Leu Phe Thr Thr Thr Gly Asp Lys
    1355                1360                1365

Asn Thr Asn Glu Thr Thr Glu Ile Lys Lys Gln Thr Ser Thr Tyr
    1370                1375                1380

Ile Asp Thr Glu Lys Met Asn Glu Ala Asp Ser Ala Asp Ser Asp
    1385                1390                1395

Asp Glu Lys Asp Phe Asp Thr Pro Asp Asn Glu Leu Met Ile Ala
    1400                1405                1410

Arg Phe His
    1415

<210> SEQ ID NO 5
<211> LENGTH: 38
<212> TYPE: DNA
<213> ORGANISM: Artificial Sequence
<220> FEATURE:
<223> OTHER INFORMATION: Synthetic

<400> SEQUENCE: 5
ataccgtcga cttgtcaatt tttatgtttg cataaacg                              38

<210> SEQ ID NO 6
<211> LENGTH: 42
<212> TYPE: DNA
<213> ORGANISM: Artificial Sequence
<220> FEATURE:
<223> OTHER INFORMATION: Synthetic

<400> SEQUENCE: 6
aattaggtac cgtacaaata aatacaatat ttttcatagc aa                         42

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
tatccgtcga ctctatttac actcatgaag acagaggtaa                            40

<210> SEQ ID NO 8
<211> LENGTH: 38
<212> TYPE: DNA
```

```
<213> ORGANISM: Artificial Sequence
<220> FEATURE:
<223> OTHER INFORMATION: Synthetic

<400> SEQUENCE: 8
aattaggtac ccttcattga aaattttaca agggtatc                              38

<210> SEQ ID NO 9
<211> LENGTH: 41
<212> TYPE: DNA
<213> ORGANISM: Artificial Sequence
<220> FEATURE:
<223> OTHER INFORMATION: Synthetic

<400> SEQUENCE: 9
ataccgtcga ctatgaatga ttgtactact tttgtaagaa t                          41

<210> SEQ ID NO 10
<211> LENGTH: 38
<212> TYPE: DNA
<213> ORGANISM: Artificial Sequence
<220> FEATURE:
<223> OTHER INFORMATION: Synthetic

<400> SEQUENCE: 10
aatatggtac ctacacattg acatagggta tcatcatt                              38

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
ataccgtcga cccttttttac acgtatattc ggacaatc                             38

<210> SEQ ID NO 12
<211> LENGTH: 37
<212> TYPE: DNA
<213> ORGANISM: Artificial Sequence
<220> FEATURE:
<223> OTHER INFORMATION: Synthetic

<400> SEQUENCE: 12
aattaggtac cgttaacacg aacaattttg cagtatg                               37

<210> SEQ ID NO 13
<211> LENGTH: 33
<212> TYPE: DNA
<213> ORGANISM: Artificial Sequence
<220> FEATURE:
<223> OTHER INFORMATION: Synthetic

<400> SEQUENCE: 13
ataccgtcga ccaaaaaacc gaaatggcat ttc                                   33

<210> SEQ ID NO 14
<211> LENGTH: 39
<212> TYPE: DNA
<213> ORGANISM: Artificial Sequence
<220> FEATURE:
<223> OTHER INFORMATION: Synthetic

<400> SEQUENCE: 14
aattaggtac catgaaatat gtaatacgtg ggttaaaag                             39
```

<210> SEQ ID NO 15
<211> LENGTH: 41
<212> TYPE: DNA
<213> ORGANISM: Artificial Sequence
<220> FEATURE:
<223> OTHER INFORMATION: Synthetic

<400> SEQUENCE: 15
ataccgtcga cttccatgtt taaagtgaaa ttagaagata t    41

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
aattaggtac ccgacattat gttatttcgg cga    33

<210> SEQ ID NO 17
<211> LENGTH: 42
<212> TYPE: DNA
<213> ORGANISM: Artificial Sequence
<220> FEATURE:
<223> OTHER INFORMATION: Synthetic

<400> SEQUENCE: 17
ataccgtcga ccagtatata taatcaaatt gagcttaaaa ag    42

<210> SEQ ID NO 18
<211> LENGTH: 41
<212> TYPE: DNA
<213> ORGANISM: Artificial Sequence
<220> FEATURE:
<223> OTHER INFORMATION: Synthetic

<400> SEQUENCE: 18
aattaggtac cagtgtttta aggcaataat tatattgtat t    41

<210> SEQ ID NO 19
<211> LENGTH: 40
<212> TYPE: DNA
<213> ORGANISM: Artificial Sequence
<220> FEATURE:
<223> OTHER INFORMATION: Synthetic

<400> SEQUENCE: 19
tcgacctcga gcataaaatt gtgtgtttca ttaaaatcat    40

<210> SEQ ID NO 20
<211> LENGTH: 41
<212> TYPE: DNA
<213> ORGANISM: Artificial Sequence
<220> FEATURE:
<223> OTHER INFORMATION: Synthetic

<400> SEQUENCE: 20
acgtagggcc catgtataaa tgaaaaatga atgtgactct t    41

<210> SEQ ID NO 21
<211> LENGTH: 41
<212> TYPE: DNA
<213> ORGANISM: Artificial Sequence
<220> FEATURE:

<223> OTHER INFORMATION: Synthetic

<400> SEQUENCE: 21
attcagtcga caagaaaaag gtaatatttt agtacactca a        41

<210> SEQ ID NO 22
<211> LENGTH: 38
<212> TYPE: DNA
<213> ORGANISM: Artificial Sequence
<220> FEATURE:
<223> OTHER INFORMATION: Synthetic

<400> SEQUENCE: 22
tattcggtac ctttgtaata tacctttatg cgttgaca        38

<210> SEQ ID NO 23
<211> LENGTH: 38
<212> TYPE: DNA
<213> ORGANISM: Artificial Sequence
<220> FEATURE:
<223> OTHER INFORMATION: Synthetic

<400> SEQUENCE: 23
atgcagtcga catgcactca ttaataattt taaaccgt        38

<210> SEQ ID NO 24
<211> LENGTH: 41
<212> TYPE: DNA
<213> ORGANISM: Artificial Sequence
<220> FEATURE:
<223> OTHER INFORMATION: Synthetic

<400> SEQUENCE: 24
tcgatgggcc cctttttcaat taattttata ttcttttgtt c        41

<210> SEQ ID NO 25
<211> LENGTH: 37
<212> TYPE: DNA
<213> ORGANISM: Artificial Sequence
<220> FEATURE:
<223> OTHER INFORMATION: Synthetic

<400> SEQUENCE: 25
ataccgtcga ccctgacgat gaattaatga tatcacg        37

<210> SEQ ID NO 26
<211> LENGTH: 40
<212> TYPE: DNA
<213> ORGANISM: Artificial Sequence
<220> FEATURE:
<223> OTHER INFORMATION: Synthetic

<400> SEQUENCE: 26
tataaggtac ccaggttaat atagccaaaa taaattgaaa        40

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
atagagtcga cggatattag ctgataaagc agcagc        36

```
<210> SEQ ID NO 28
<211> LENGTH: 37
<212> TYPE: DNA
<213> ORGANISM: Artificial Sequence
<220> FEATURE:
<223> OTHER INFORMATION: Synthetic

<400> SEQUENCE: 28
gatttggtac ctttgttttc atgtcccatc ataattc                              37

<210> SEQ ID NO 29
<211> LENGTH: 41
<212> TYPE: DNA
<213> ORGANISM: Artificial Sequence
<220> FEATURE:
<223> OTHER INFORMATION: Synthetic

<400> SEQUENCE: 29
ataccgtcga ctattctact taaagatgaa tagcacatat g                         41

<210> SEQ ID NO 30
<211> LENGTH: 36
<212> TYPE: DNA
<213> ORGANISM: Artificial Sequence
<220> FEATURE:
<223> OTHER INFORMATION: Synthetic

<400> SEQUENCE: 30
acattgggcc cttcccctca catatcaatc ataaat                               36

<210> SEQ ID NO 31
<211> LENGTH: 34
<212> TYPE: DNA
<213> ORGANISM: Artificial Sequence
<220> FEATURE:
<223> OTHER INFORMATION: Synthetic

<400> SEQUENCE: 31
atacagtcga cgcatcctat tcccatcctt tcct                                 34

<210> SEQ ID NO 32
<211> LENGTH: 35
<212> TYPE: DNA
<213> ORGANISM: Artificial Sequence
<220> FEATURE:
<223> OTHER INFORMATION: Synthetic

<400> SEQUENCE: 32
actgagggcc cgacaagaag cattacagag agcaa                                35

<210> SEQ ID NO 33
<211> LENGTH: 41
<212> TYPE: DNA
<213> ORGANISM: Artificial Sequence
<220> FEATURE:
<223> OTHER INFORMATION: Synthetic

<400> SEQUENCE: 33
ataccgtcga cattttgccc aagaatataa aataataaga t                         41

<210> SEQ ID NO 34
<211> LENGTH: 41
<212> TYPE: DNA
<213> ORGANISM: Artificial Sequence
<220> FEATURE:
<223> OTHER INFORMATION: Synthetic
```

<400> SEQUENCE: 34
aattaggtac ccagagaaag aaaaatgtca atataaataa a          41

<210> SEQ ID NO 35
<211> LENGTH: 33
<212> TYPE: DNA
<213> ORGANISM: Artificial Sequence
<220> FEATURE:
<223> OTHER INFORMATION: Synthetic

<400> SEQUENCE: 35
cataagcggc cgcgccattc agaccaagca agg          33

<210> SEQ ID NO 36
<211> LENGTH: 41
<212> TYPE: DNA
<213> ORGANISM: Artificial Sequence
<220> FEATURE:
<223> OTHER INFORMATION: Synthetic

<400> SEQUENCE: 36
ttaaactgca gcttttcaat taattttata ttcttttgtt c          41

<210> SEQ ID NO 37
<211> LENGTH: 21
<212> TYPE: PRT
<213> ORGANISM: Artificial Sequence
<220> FEATURE:
<223> OTHER INFORMATION: Synthetic

<400> SEQUENCE: 37

Phe Leu Asn Cys Cys Pro Cys Cys Met Glu Pro Gly Ser Asp Tyr Lys
1               5                   10                  15

Asp Asp Asp Asp Lys
            20

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
gtggaattgt gagcggataa ca          22

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
tcatcgtcct tatagtcgga tcc          23

<210> SEQ ID NO 40
<211> LENGTH: 26
<212> TYPE: DNA
<213> ORGANISM: Artificial Sequence
<220> FEATURE:
<223> OTHER INFORMATION: Synthetic

<400> SEQUENCE: 40
atgttttgta atttatggga tagcga          26

<210> SEQ ID NO 41
<211> LENGTH: 28
<212> TYPE: DNA
<213> ORGANISM: Artificial Sequence
<220> FEATURE:
<223> OTHER INFORMATION: Synthetic

<400> SEQUENCE: 41
gttgagtacg cactaatatg tcaatttg                                    28

<210> SEQ ID NO 42
<211> LENGTH: 32
<212> TYPE: DNA
<213> ORGANISM: Artificial Sequence
<220> FEATURE:
<223> OTHER INFORMATION: Synthetic

<400> SEQUENCE: 42
aaccataaca ttatcatata tgttaattac ac                               32

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
atttccagag aatgaccaca ac                                          22

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
ttaagatggc ctgggtgatt c                                           21

<210> SEQ ID NO 45
<211> LENGTH: 27
<212> TYPE: DNA
<213> ORGANISM: Artificial Sequence
<220> FEATURE:
<223> OTHER INFORMATION: Synthetic

<400> SEQUENCE: 45
ctcttactac ttattatcta tctctca                                     27

<210> SEQ ID NO 46
<211> LENGTH: 19
<212> TYPE: DNA
<213> ORGANISM: Artificial Sequence
<220> FEATURE:
<223> OTHER INFORMATION: Synthetic

<400> SEQUENCE: 46
ccaggcgtag gtcctttac                                              19

<210> SEQ ID NO 47
<211> LENGTH: 28
<212> TYPE: DNA
<213> ORGANISM: Artificial Sequence
<220> FEATURE:

<223> OTHER INFORMATION: Synthetic

<400> SEQUENCE: 47
acccataact acatattttc tagtaatg                               28

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
gacaagttcc agaagcatcc t                                     21

<210> SEQ ID NO 49
<211> LENGTH: 28
<212> TYPE: DNA
<213> ORGANISM: Artificial Sequence
<220> FEATURE:
<223> OTHER INFORMATION: Synthetic

<400> SEQUENCE: 49
acccataact acatattttc tagtaatg                               28

<210> SEQ ID NO 50
<211> LENGTH: 30
<212> TYPE: DNA
<213> ORGANISM: Artificial Sequence
<220> FEATURE:
<223> OTHER INFORMATION: Synthetic

<400> SEQUENCE: 50
agatttagtt acacttgaag aattagtatt                            30

<210> SEQ ID NO 51
<211> LENGTH: 28
<212> TYPE: DNA
<213> ORGANISM: Artificial Sequence
<220> FEATURE:
<223> OTHER INFORMATION: Synthetic

<400> SEQUENCE: 51
acccataact acatattttc tagtaatg                               28

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
gatttataac taggagcact acattta                               27

<210> SEQ ID NO 53
<211> LENGTH: 28
<212> TYPE: DNA
<213> ORGANISM: Artificial Sequence
<220> FEATURE:
<223> OTHER INFORMATION: Synthetic

<400> SEQUENCE: 53
acccataact acatattttc tagtaatg                               28

```
<210> SEQ ID NO 54
<211> LENGTH: 26
<212> TYPE: DNA
<213> ORGANISM: Artificial Sequence
<220> FEATURE:
<223> OTHER INFORMATION: Synthetic

<400> SEQUENCE: 54
ttataaccat taggagcact actttc                                          26

<210> SEQ ID NO 55
<211> LENGTH: 28
<212> TYPE: DNA
<213> ORGANISM: Artificial Sequence
<220> FEATURE:
<223> OTHER INFORMATION: Synthetic

<400> SEQUENCE: 55
acccataact acatattttc tagtaatg                                        28

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
gacaagttcc agaagcatcc t                                               21

<210> SEQ ID NO 57
<211> LENGTH: 24
<212> TYPE: DNA
<213> ORGANISM: Artificial Sequence
<220> FEATURE:
<223> OTHER INFORMATION: Synthetic

<400> SEQUENCE: 57
gttactacaa cattcctgat tcag                                            24

<210> SEQ ID NO 58
<211> LENGTH: 27
<212> TYPE: DNA
<213> ORGANISM: Artificial Sequence
<220> FEATURE:
<223> OTHER INFORMATION: Synthetic

<400> SEQUENCE: 58
aatgaaaata taaaaatgct gggggat                                         27

<210> SEQ ID NO 59
<211> LENGTH: 27
<212> TYPE: DNA
<213> ORGANISM: Artificial Sequence
<220> FEATURE:
<223> OTHER INFORMATION: Synthetic

<400> SEQUENCE: 59
taccattagt gttttataca cttaagg                                         27

<210> SEQ ID NO 60
<211> LENGTH: 23
<212> TYPE: DNA
<213> ORGANISM: Artificial Sequence
<220> FEATURE:
<223> OTHER INFORMATION: Synthetic
```

<400> SEQUENCE: 60
ccaaaatatg gccaagtact tgc                                            23

<210> SEQ ID NO 61
<211> LENGTH: 164
<212> TYPE: PRT
<213> ORGANISM: Artificial Sequence
<220> FEATURE:
<223> OTHER INFORMATION: Synthetic

<400> SEQUENCE: 61

Met Gly Ser Ser His His His His His Ser Ser Gly Gly Thr Lys
1               5                   10                  15

Lys Tyr Gly Tyr Leu Gly Glu Val Ile Ala Ala Arg Leu Ser Pro Lys
            20                  25                  30

Asp Lys Ile Met Asn Tyr Val His Glu Thr Asn Glu Asp Ile Met Ser
        35                  40                  45

Asn Leu Arg Arg Tyr Asp Met Glu Asn Ala Phe Lys Asn Lys Met Ser
    50                  55                  60

Thr Tyr Val Asp Asp Phe Ala Phe Phe Asp Asp Cys Gly Lys Asn Glu
65                  70                  75                  80

Gln Phe Leu Asn Glu Arg Cys Asp Tyr Cys Pro Val Ile Glu Glu Val
                85                  90                  95

Glu Glu Thr Gln Leu Phe Thr Thr Gly Asp Lys Asn Thr Asn Lys
            100                 105                 110

Thr Thr Glu Ile Lys Lys Gln Thr Ser Thr Tyr Ile Asp Thr Glu Lys
        115                 120                 125

Met Asn Glu Ala Asp Ser Ala Asp Ser Asp Glu Lys Asp Ser Asp
    130                 135                 140

Thr Pro Asp Asp Glu Leu Met Ile Ser Arg Phe His Asp Tyr Lys Asp
145                 150                 155                 160

Asp Asp Asp Lys

<210> SEQ ID NO 62
<211> LENGTH: 146
<212> TYPE: PRT
<213> ORGANISM: Plasmodium falciparum

<400> SEQUENCE: 62

Cys Glu Tyr Gln Ala Val Ala Ser Ala Asn Phe Tyr Ser Ala Lys Lys
1               5                   10                  15

Val Gly Gln Phe Leu Gly Arg Lys Phe Leu Pro Ile Thr Thr Tyr Phe
            20                  25                  30

Leu Val Met Arg Ile Ser Trp Thr His Ala Phe Thr Thr Gly Gln His
        35                  40                  45

Leu Ile Ser Ala Phe Gly Ser Pro Ser Thr Ala Asn Gly Lys Ser
    50                  55                  60

Asn Ala Ser Gly Tyr Lys Ser Pro Glu Ser Phe Phe Thr His Gly
65                  70                  75                  80

Leu Ala Ala Glu Ala Ser Lys Tyr Leu Phe Phe Tyr Phe Thr Asn
                85                  90                  95

Leu Tyr Leu Asp Ala Tyr Lys Ser Phe Pro Gly Gly Phe Gly Pro Ala
            100                 105                 110

Ile Lys Glu Gln Thr Gln His Val Gln Glu Gln Thr Tyr Glu Arg Lys
        115                 120                 125

Pro Ser Val His Ser Phe Asn Arg Asn Phe Phe Met Glu Leu Val Asn

<210> SEQ ID NO 63
<211> LENGTH: 438
<212> TYPE: DNA
<213> ORGANISM: Plasmodium falciparum

<400> SEQUENCE: 63

```
tgtgaatatc aggctgtggc aagtgccaat ttctactctg ctaaaaaggt aggtcagttt      60
cttggaagaa aattttacc cataactaca tattttctag taatgagaat tagttggaca     120
catgctttta caactggaca acatttgatt agcgcttttg gttccccaag ttctactgct    180
aatggtaaaa gtaatgctag tggttataaa tcccctgaaa gttttttctt cactcacgga    240
cttgctgctg aagcatccaa atatttattt ttttattttt tcacaaattt ataccttgat    300
gcctacaaat cttttcctgg aggatttggt cctgcaataa agaacaaac tcaacatgtt     360
caagaacaaa cctacgaacg caaaccgtca gttcatagtt ttaatagaaa ttttttcatg    420
gaactcgtaa atggattc                                                   438
```

<210> SEQ ID NO 64
<211> LENGTH: 186
<212> TYPE: PRT
<213> ORGANISM: Plasmodium falciparum

<400> SEQUENCE: 64

```
Thr Ser Asn Phe Arg Phe Leu Asp Arg Tyr Tyr Gly Val Phe Asn Lys
  1               5                  10                  15

Tyr Phe Ile Asn Tyr Ala Ile Ile Lys Leu Lys Glu Ile Thr Ser Asp
             20                  25                  30

Leu Leu Ile Lys Tyr Glu Arg Glu Ala Tyr Leu Ser Met Lys Lys Tyr
         35                  40                  45

Gly Tyr Leu Gly Glu Val Ile Ala Ala Arg Leu Ser Pro Lys Asp Lys
     50                  55                  60

Ile Met Asn Tyr Val His Glu Thr Asn Glu Asp Ile Met Ser Asn Leu
 65                  70                  75                  80

Arg Arg Tyr Asp Met Glu Asn Ala Phe Lys Asn Lys Met Ser Thr Tyr
                 85                  90                  95

Val Asp Asp Phe Ala Phe Phe Asp Asp Cys Gly Lys Asn Glu Gln Phe
            100                 105                 110

Leu Asn Glu Arg Cys Asp Tyr Cys Pro Val Ile Glu Glu Val Glu Glu
        115                 120                 125

Thr Gln Leu Phe Thr Thr Thr Gly Asp Lys Asn Thr Asn Lys Thr Thr
    130                 135                 140

Glu Ile Lys Lys Gln Thr Ser Thr Tyr Ile Asp Thr Glu Lys Met Asn
145                 150                 155                 160

Glu Ala Asp Ser Ala Asp Ser Asp Glu Lys Asp Ser Asp Thr Pro
                165                 170                 175

Asp Asp Glu Leu Met Ile Ser Arg Phe His
            180                 185
```

<210> SEQ ID NO 65
<211> LENGTH: 558
<212> TYPE: DNA
<213> ORGANISM: Plasmodium falciparum

<400> SEQUENCE: 65

```
acaagtaatt tccgtttctt ggatagatat tatggtgtat tcaataaata ttttataaac    60
tatgccataa ttaaacttaa agaaattact agtgatcttt taataaaata tgaacgtgag   120
gcttatttaa gtatgaaaaa atatggttat ttaggtgaag ttattgcagc tagactttct   180
ccaaaagata aaattatgaa ttatgtgcac gaaactaacg aagatatcat gagtaattta   240
agaagatatg atatggaaaa tgctttcaaa acaaaatgt caacatatgt agatgatttt   300
gcttttttg atgattgcgg aaaaaatgaa caattttaa atgagagatg tgattattgt   360
cctgtaattg aagaggtcga agaaacacaa ttatttacta ccactggtga taaaaacact   420
aataagacca cggaaataaa aaacaaact agtacatata ttgatactga aaaaatgaat   480
gaagcggatt ctgctgatag cgacgatgaa aaggattctg atactcctga cgatgaatta   540
atgatatcac gatttcac                                                558
```

<210> SEQ ID NO 66
<211> LENGTH: 308
<212> TYPE: PRT
<213> ORGANISM: Plasmodium falciparum

<400> SEQUENCE: 66

```
Ser Ile Asn Glu Asn Gln Asn Glu Asn Asp Thr Ile Ser Gln Asn Val
1               5                   10                  15

Asn Gln His Glu Asn Ile Asn Gln Asn Val Asn Asp Asn Asp Asn Ile
            20                  25                  30

Glu Gln Leu Lys Ser Met Ile Gly Asn Asp Glu Leu His Lys Asn Leu
        35                  40                  45

Thr Ile Leu Glu Lys Leu Ile Leu Glu Ser Leu Glu Lys Asp Lys Leu
    50                  55                  60

Lys Tyr Pro Leu Leu Lys Gln Gly Thr Glu Gln Leu Ile Asp Ile Ser
65                  70                  75                  80

Lys Phe Asn Lys Lys Asn Ile Thr Asp Ala Asp Glu Thr Tyr Ile
                85                  90                  95

Ile Pro Thr Val Gln Ser Thr Phe His Asp Ile Val Lys Tyr Glu His
            100                 105                 110

Leu Ile Lys Glu Gln Ser Ile Glu Ile Tyr Asn Ser Asp Ile Ser Asp
        115                 120                 125

Lys Ile Lys Lys Lys Ile Phe Ile Val Arg Thr Leu Lys Thr Ile Lys
    130                 135                 140

Leu Met Leu Ile Pro Leu Asn Ser Tyr Lys Gln Asn Asn Asp Leu Lys
145                 150                 155                 160

Ser Ala Leu Glu Glu Leu Asn Asn Val Phe Thr Asn Lys Glu Ala Gln
                165                 170                 175

Glu Glu Ser Ser Pro Ile Gly Asp His Gly Thr Phe Phe Arg Lys Leu
            180                 185                 190

Leu Thr His Val Arg Thr Ile Lys Glu Asn Glu Asp Ile Glu Asn Lys
        195                 200                 205

Gly Glu Thr Leu Ile Leu Gly Asp Asn Lys Ile Asp Val Met Asn Ser
    210                 215                 220

Asn Asp Phe Phe Phe Thr Thr Asn Ser Asn Val Lys Phe Met Glu Asn
225                 230                 235                 240

Leu Asp Asp Ile Thr Asn Gln Tyr Gly Leu Gly Leu Ile Asn His Leu
                245                 250                 255

Gly Pro His Leu Ile Ala Leu Gly His Phe Thr Val Leu Lys Leu Ala
```

```
            260                265                270
Leu Lys Asn Tyr Lys Asn Tyr Phe Glu Ala Lys Ser Ile Lys Phe Phe
        275                280                285

Ser Trp Gln Lys Ile Leu Glu Phe Ser Met Ser Asp Arg Phe Lys Val
    290                295                300

Leu Asp Met Met
305

<210> SEQ ID NO 67
<211> LENGTH: 924
<212> TYPE: DNA
<213> ORGANISM: Plasmodium falciparum

<400> SEQUENCE: 67
tcaataaatg aaaatcaaaa tgaaaatgat accattagtc aaaatgtcaa ccaacatgaa      60
aatattaatc aaaatgtaaa tgataatgac aatattgaac aattaaaatc catgattgga     120
aatgatgaac tacataagaa tttaacaata ttagaaaaat taattttaga gtctttagaa     180
aaagataaat taaaatatcc tctccttaaa caaggaactg aacaattgat agatatatca     240
aaatttaata aaaaaaatat tacagatgcg gatgatgaaa cgtacatcat acccaccgtc     300
caatcaacgt ttcacgatat tgtgaaatac gaacatctta taaaagaaca atcaatagaa     360
atttacaatt ctgatatatc agataaaatt aagaaaaaaa ttttatagt aagaacattg     420 aaaccataa aattaatgct tataccatta aactcgtaca acaaaataa tgacttgaaa     480 tctgcactcg aagaattaaa taatgtatt acaaacaaag aagctcaaga ggaaagcagt     540
ccaataggcg accatgggac attctttaga aaattgttaa cacatgttag aacaattaaa     600
gaaaatgaag atatagaaaa taaggagaa acacttatat taggcgataa taaaatagat     660
gtaatgaatt caacgatttt cttttttaca accaactcaa atgtaaaatt tatggaaaat     720
ttagatgata taacaaatca atatggatta ggtttgatta atcatctagg tcctcattta     780
atagccttgg gtcattttac cgtattaaaa ttagcactaa aaaattacaa aaactatttt     840
gaagcaaaaa gtattaaatt ttttagttgg caaaaaattt tagagttctc catgtctgat     900
agatttaaag ttcttgatat gatg                                              924

<210> SEQ ID NO 68
<211> LENGTH: 26
<212> TYPE: DNA
<213> ORGANISM: Artificial Sequence
<220> FEATURE:
<223> OTHER INFORMATION: Synthetic

<400> SEQUENCE: 68
gtgcaatata tcaaagtgta catgca                                             26

<210> SEQ ID NO 69
<211> LENGTH: 27
<212> TYPE: DNA
<213> ORGANISM: Artificial Sequence
<220> FEATURE:
<223> OTHER INFORMATION: Synthetic

<400> SEQUENCE: 69
aagaaaataa atgcaaaaca agttaga                                            27

<210> SEQ ID NO 70
<211> LENGTH: 27
<212> TYPE: DNA
```

<213> ORGANISM: Artificial Sequence
<220> FEATURE:
<223> OTHER INFORMATION: Synthetic

<400> SEQUENCE: 70
atttacaaac aaagaagctc aagagga                                27

<210> SEQ ID NO 71
<211> LENGTH: 31
<212> TYPE: DNA
<213> ORGANISM: Artificial Sequence
<220> FEATURE:
<223> OTHER INFORMATION: Synthetic

<400> SEQUENCE: 71
ttttctatat cttcattttc tttaattgtt c                           31

<210> SEQ ID NO 72
<211> LENGTH: 182
<212> TYPE: PRT
<213> ORGANISM: Artificial Sequence
<220> FEATURE:
<223> OTHER INFORMATION: Synthetic

<400> SEQUENCE: 72

Cys Glu Tyr Gln Ala Val Ala Ser Ala Asn Phe Tyr Ser Ala Lys Lys
1               5                   10                  15

Val Gly Gln Phe Ile Gly Arg Lys Phe Leu Pro Ile Thr Thr Tyr Phe
            20                  25                  30

Leu Val Met Arg Ile Ser Trp Thr His Ala Ile Thr Thr Gly Gln His
        35                  40                  45

Leu Ile Pro Gln Leu Thr Asp Pro Glu Tyr Gly Gln Thr Pro Lys Gly
    50                  55                  60

Lys Asp Ala Ser Gly Thr Cys Pro Ser Ala Gly Leu Glu Lys Cys Thr
65                  70                  75                  80

Asn Tyr Arg Ala Pro Gly Ser Phe Phe Thr His Gly Leu Ala Ala
                85                  90                  95

Glu Ala Ser Lys Tyr Leu Phe Tyr Phe Phe Thr Asn Leu Tyr Leu
            100                 105                 110

Asp Ala Tyr Lys Ser Phe Pro Gly Gly Phe Gly Pro Ala Ile Lys Glu
        115                 120                 125

Gln Thr Gln His Val Gln Glu Gln Thr Tyr Glu Arg Lys Pro Ser Val
    130                 135                 140

His Ser Phe Asn Arg Asn Phe Phe Met Glu Leu Ala Asn Gly Phe Met
145                 150                 155                 160

Tyr Ala Phe Cys Phe Phe Ala Ile Ser Gln Met Tyr Ala Tyr Phe Glu
                165                 170                 175

Asn Ile Asn Phe Tyr Ile
            180

<210> SEQ ID NO 73
<211> LENGTH: 546
<212> TYPE: DNA
<213> ORGANISM: Artificial Sequence
<220> FEATURE:
<223> OTHER INFORMATION: Synthetic

<400> SEQUENCE: 73
tgtgaatatc aggcggtagc aagtgcaaat ttctactctg ctaaaaaggt agggcaattt    60
attggaagaa aatttttacc cataactaca tattttctag taatgagaat tagttggaca   120

-continued

```
cacgctatta caactggaca acatttaatt ccccaattaa cagatcctga atacggtcaa    180
actcctaagg gaaaggatgc ttctggaact tgtcctagtg cgggtttaga aaatgtact     240 aactatagag ctcctggaag ttttttcttt actcacggac ttgctgctga agcatccaaa   300
tatttatttt tttatttttt cacaaattta taccttgatg cctacaaatc ttttcctgga   360
ggatttggtc ctgcaataaa agaacaaact caacatgttc aagaacaaac ctacgaacgc   420
aaaccgtcag ttcatagttt taatagaaat ttttcatgg aacttgcaaa tggtttcatg    480 tatgctttt gttttttttgc tatttcacaa atgtatgcat attttgaaaa tattaatttt   540
tatatt                                                               546
```

<210> SEQ ID NO 74
<211> LENGTH: 420
<212> TYPE: PRT
<213> ORGANISM: Artificial Sequence
<220> FEATURE:
<223> OTHER INFORMATION: Synthetic

<400> SEQUENCE: 74

```
Leu Tyr Leu Pro Gly Tyr Tyr Asn Ala Val Glu Met Ser Phe Thr Glu
 1               5                  10                  15

Glu Lys Glu Phe Ser Lys Leu Phe Glu Ser Leu Ile Gln Cys Ile Glu
                20                  25                  30

Lys Cys His Ser Asp Gln Ala Arg Gln Ile Ser Lys Asp Ser Asn Leu
            35                  40                  45

Leu Asn Asn Ile Thr Lys Cys Asp Leu Cys Lys Gly Ala Phe Leu Tyr
        50                  55                  60

Ala Asn Met Lys Phe Asp Glu Val Pro Ser Met Leu Gln Lys Phe Tyr
 65                  70                  75                  80

Val Tyr Leu Thr Lys Gly Leu Lys Ile Gln Lys Val Ser Ser Leu Ile
                85                  90                  95

Lys Thr Leu Asp Ile Tyr Gln Asp Tyr Ser Asn Tyr Leu Ser His Asp
            100                 105                 110

Ile Asn Trp Tyr Thr Phe Leu Phe Leu Phe Arg Leu Thr Ser Phe Lys
        115                 120                 125

Glu Ile Ala Lys Lys Asn Val Ala Glu Ala Met Tyr Leu Asn Ile Lys
130                 135                 140

Asp Glu Asp Thr Phe Asn Lys Thr Val Val Thr Asn Tyr Trp Tyr Pro
145                 150                 155                 160

Ser Pro Ile Lys Lys Tyr Tyr Thr Leu Tyr Val Arg Lys His Ile Pro
                165                 170                 175

Asn Asn Leu Val Asp Glu Leu Glu Lys Leu Met Lys Ser Gly Thr Leu
            180                 185                 190

Glu Lys Met Lys Lys Ser Leu Thr Phe Leu Val His Val Asn Ser Phe
        195                 200                 205

Leu Gln Leu Asp Phe Phe His Gln Leu Asn Glu Pro Pro Leu Gly Leu
    210                 215                 220

Pro Arg Ser Tyr Pro Leu Ser Leu Val Leu Glu His Lys Phe Lys Glu
225                 230                 235                 240

Trp Met Asn Ser Ser Pro Ala Gly Phe Tyr Phe Ser Asn Tyr Gln Asn
                245                 250                 255

Pro Tyr Ile Arg Lys Asp Leu His Asp Lys Val Leu Ser Gln Lys Phe
            260                 265                 270

Glu Pro Pro Lys Met Asn Gln Trp Asn Lys Val Leu Lys Ser Leu Ile
```

```
                    275                 280                 285
Glu Cys Ala Tyr Asp Met Tyr Phe Glu Gln Arg His Val Lys Asn Leu
    290                 295                 300
Tyr Lys Tyr His Asn Ile Tyr Asn Ile Asn Asn Lys Leu Met Leu Met
305                 310                 315                 320
Arg Asp Ser Ile Asp Leu Tyr Lys Asn Asn Phe Asp Asp Val Leu Phe
                325                 330                 335
Phe Ala Asp Ile Phe Asn Met Arg Lys Tyr Met Thr Ala Thr Pro Val
            340                 345                 350
Tyr Lys Lys Val Lys Asp Arg Val Tyr His Thr Leu His Ser Ile Thr
        355                 360                 365
Gly Asn Ser Val Asn Phe Tyr Lys Tyr Gly Ile Ile Tyr Gly Phe Lys
    370                 375                 380
Val Asn Lys Glu Ile Leu Lys Glu Val Val Asp Glu Leu Tyr Ser Ile
385                 390                 395                 400
Tyr Asn Phe Asn Thr Asp Ile Phe Thr Asp Thr Ser Phe Leu Gln Thr
                405                 410                 415
Val Tyr Leu Leu
            420

<210> SEQ ID NO 75
<211> LENGTH: 1260
<212> TYPE: DNA
<213> ORGANISM: Artificial Sequence
<220> FEATURE:
<223> OTHER INFORMATION: Synthetic

<400> SEQUENCE: 75
ctttatttac caggatatta caacgctgtc gaaatgtctt ttacggaaga aaaagagttt      60
tccaaacttt ttgaaagctt aatacaatgt attgaaaaat gccattcaga ccaagcaagg     120
caaatatcaa aagatagtaa tttacttaat aatataacaa atgtgatttt gtgtaaagga     180 gccttttat atgctaatat gaaattcgat gaagttcctt caatgttgca aaaatttttac     240 gtatatttaa ctaaaggtct caaaatacaa aaagtatcat cactaatcaa acgctagat      300 atatatcaag attacagcaa ttacttatca catgatatta attggtacac attcctattt     360
ttatttagac ttacaagttt taagaaaatt gcaagaaaaa atgttgctga agcaatgtat     420
ttaaatataa aagatgaaga cacattcaac aaaacggtag taacaaacta ttggtaccca     480
tctcctataa aaaatatta tacattatat gttagaaaac atataccaaa taatttagta     540
gatgaattgg agaaattaat gaaaagtggc actttagaaa aaatgaaaaa atctctcacc     600
tttttagtac atgtgaattc attttttacaa ttagattttt tccatcaatt aaatgaacca     660
cctcttggat tacctcgatc atatccatta tcgttagttc tcgaacataa atttaaagaa     720
tggatgaaca gttcgccagc aggttttctat ttttcaaatt atcaaaatcc atatatcaga     780
aaagatttgc atgataaagt tttatcacaa aaatttgaac cacctaaaat gaatcagtgg     840
aacaaagttt tgaaatcatt aattgaatgc gcatatgata tgtatttttga acagagacat     900 gttaaaaatt tatataaaata tcataacatt tataatataa ataacaaatt aatgttaatg     960
cgagattcaa tcgatttgta taaaaacaat tttgacgatg tgttatttttt tgcggatata    1020 tttaatatga gaaaatatat gacagctaca ccagtatata aaaaagtaaa agacagagtg    1080
taccatacat tgcatagtat tacaggaaat tctgtcaatt tttataaaata tggtattata    1140 tatggattta agtaaacaaa agaaatatta aaagaagttg tcgatgaatt gtattccatc    1200
``` tataattttta acaccgacat atttacggat acttcctttt tacaaaccgt ttatttatta    1260

<210> SEQ ID NO 76
<211> LENGTH: 120
<212> TYPE: PRT
<213> ORGANISM: Artificial Sequence
<220> FEATURE:
<223> OTHER INFORMATION: Synthetic

<400> SEQUENCE: 76

Ser Val Asn Asn Val Phe Phe Met Asn Val Ala Asn Asn Tyr Ser Lys
1               5                   10                  15

Leu Asn Lys Glu Glu Arg Glu Ile Glu Ile His Asn Ser Met Ala Ser
            20                  25                  30

Arg Tyr Tyr Ala Lys Thr Met Phe Ala Ala Phe Gln Met Leu Phe Ser
        35                  40                  45

Thr Met Leu Ser Asn Asn Val Asp Asn Leu Asp Lys Ala Tyr Gly Leu
    50                  55                  60

Ser Glu Asn Ile Gln Val Ala Thr Ser Thr Ser Ala Phe Leu Thr Phe
65                  70                  75                  80

Ala Tyr Val Tyr Asn Gly Ser Ile Met Asp Ser Val Thr Asn Ser Leu
                85                  90                  95

Leu Pro Pro Tyr Ala Lys Lys Pro Ile Thr Gln Leu Lys Tyr Gly Lys
            100                 105                 110

Thr Phe Val Phe Ser Asn Tyr Phe
        115                 120

<210> SEQ ID NO 77
<211> LENGTH: 360
<212> TYPE: DNA
<213> ORGANISM: Artificial Sequence
<220> FEATURE:
<223> OTHER INFORMATION: Synthetic

<400> SEQUENCE: 77
agtgtgaata acgttttttt catgaatgtt gctaataatt attccaaatt aaacaaagaa      60
gaaagagaaa tcgaaataca taattccatg gcatcaagat attatgcaaa aacgatgttt     120
gcagcatttc aaatgttatt ttcaacaatg ttgagcaaca atgtagataa tcttgataaa     180
gcatatggat taagtgaaaa tatccaagta gcaacaagta cttccgcttt tcttactttt     240
gcatatgtat ataacggaag tataatggat agtgtgacta acagtttatt gccaccatat     300
gcgaagaaac ctataacaca attaaaatat ggaaaaacct tcgttttctc aaactatttc     360

<210> SEQ ID NO 78
<211> LENGTH: 1417
<212> TYPE: PRT
<213> ORGANISM: Artificial Sequence
<220> FEATURE:
<223> OTHER INFORMATION: Synthetic

<400> SEQUENCE: 78

Met Val Ser Phe Phe Lys Thr Pro Ile Phe Ile Leu Ile Ile Phe Leu
1               5                   10                  15

Tyr Leu Asn Glu Lys Val Ile Cys Ser Ile Asn Glu Asn Gln Asn Glu
            20                  25                  30

Asn Asp Thr Ile Ser Gln Asn Val Asn Gln His Glu Asn Ile Asn Gln
        35                  40                  45

Asn Val Asn Asp Asn Asp Asn Ile Glu Gln Leu Lys Ser Met Ile Gly
    50                  55                  60

```
Asn Asp Glu Leu His Lys Asn Leu Thr Ile Leu Glu Lys Leu Ile Leu
 65                  70                  75                  80

Glu Ser Leu Glu Lys Asp Lys Leu Lys Tyr Pro Leu Leu Lys Gln Gly
                 85                  90                  95

Thr Glu Gln Leu Ile Asp Ile Ser Lys Phe Asn Lys Lys Asn Ile Thr
            100                 105                 110

Asp Ala Asp Asp Glu Thr Tyr Ile Ile Pro Thr Val Gln Ser Thr Phe
            115                 120                 125

His Asp Ile Val Lys Tyr Glu His Leu Ile Lys Glu Gln Ser Ile Glu
            130                 135                 140

Ile Tyr Asn Ser Asp Ile Ser Asp Lys Ile Lys Lys Ile Phe Ile
145                 150                 155                 160

Val Arg Thr Leu Lys Thr Ile Lys Leu Met Leu Ile Pro Leu Asn Ser
                165                 170                 175

Tyr Lys Gln Asn Asn Asp Leu Lys Ser Ala Leu Glu Glu Leu Asn Asn
            180                 185                 190

Val Phe Thr Asn Lys Glu Ala Gln Glu Glu Ser Ser Pro Ile Gly Asp
            195                 200                 205

His Gly Thr Phe Phe Arg Lys Leu Leu Thr His Val Arg Thr Ile Lys
            210                 215                 220

Glu Asn Glu Asp Ile Glu Asn Lys Gly Glu Thr Leu Ile Leu Gly Asp
225                 230                 235                 240

Asn Lys Ile Asp Val Met Asn Ser Asn Asp Phe Phe Thr Thr Asn
            245                 250                 255

Ser Asn Val Lys Phe Met Glu Asn Leu Asp Asp Ile Thr Asn Gln Tyr
            260                 265                 270

Gly Leu Gly Leu Ile Asn His Leu Gly Pro His Leu Ile Ala Leu Gly
            275                 280                 285

His Phe Thr Val Leu Lys Leu Ala Leu Lys Asn Tyr Lys Asn Tyr Phe
            290                 295                 300

Glu Ala Lys Ser Ile Lys Phe Phe Ser Trp Gln Lys Ile Leu Glu Phe
305                 310                 315                 320

Ser Met Ser Asp Arg Phe Lys Val Leu Asp Met Met Cys Asn His Glu
            325                 330                 335

Ser Val Tyr Tyr Ser Glu Lys Lys Arg Arg Lys Thr Tyr Leu Lys Val
            340                 345                 350

Asp Arg Ser Ser Thr Ser Met Glu Cys Asn Ile Leu Glu Tyr Leu Leu
            355                 360                 365

His Tyr Phe Asn Lys Tyr Gln Leu Glu Ile Ile Lys Thr Thr Gln Asp
            370                 375                 380

Thr Asp Phe Asp Leu His Gly Met Met Glu His Lys Tyr Ile Lys Asp
385                 390                 395                 400

Tyr Phe Phe Ser Phe Met Cys Asn Asp Pro Lys Glu Cys Ile Ile Tyr
            405                 410                 415

His Thr Asn Gln Phe Lys Lys Glu Ala Asn Glu Asn Thr Phe Pro
            420                 425                 430

Glu Gln Glu Glu Pro Asn Arg Glu Ile Ser Ala Tyr Asn Leu Tyr Leu
            435                 440                 445

Asn Tyr Tyr Tyr Phe Met Lys Arg Tyr Ser Ser Tyr Gly Val Lys Lys
            450                 455                 460

Thr Leu Tyr Val His Leu Leu Asn Leu Thr Gly Leu Leu Asn Tyr Asp
465                 470                 475                 480
```

```
Thr Arg Ser Tyr Val Thr Ser Leu Tyr Leu Pro Gly Tyr Tyr Asn Ala
                485                 490                 495

Val Glu Met Ser Phe Thr Glu Lys Glu Phe Ser Lys Leu Phe Glu
            500                 505                 510

Ser Leu Ile Gln Cys Ile Glu Lys Cys His Ser Asp Gln Ala Arg Gln
            515                 520                 525

Ile Ser Lys Asp Ser Asn Leu Leu Asn Asp Ile Thr Lys Cys Asp Leu
            530                 535                 540

Cys Lys Gly Ala Phe Leu Tyr Ser Asn Met Lys Phe Asp Glu Val Pro
545                 550                 555                 560

Ser Met Leu Gln Lys Phe Tyr Leu Tyr Leu Thr Lys Gly Leu Lys Ile
                565                 570                 575

Gln Lys Val Ser Ser Leu Ile Lys Thr Leu Asp Ile Tyr Gln Asp Tyr
            580                 585                 590

Ser Asn Phe Leu Ser His Asp Ile Asn Trp Tyr Thr Phe Leu Phe Leu
            595                 600                 605

Phe Arg Leu Thr Ser Phe Lys Glu Ile Ser Lys Lys Asn Val Ala Glu
            610                 615                 620

Ala Met Tyr Leu Asn Ile Lys Asp Glu Asp Thr Phe Asn Lys Thr Ile
625                 630                 635                 640

Val Thr Asn Tyr Trp Tyr Pro Ser Pro Ile Lys Lys Tyr Tyr Thr Leu
                645                 650                 655

Tyr Val Arg Lys His Ile Pro Asn Asn Leu Val Asp Glu Leu Glu Lys
                660                 665                 670

Leu Met Lys Ser Gly Thr Leu Glu Lys Met Lys Lys Ser Leu Thr Phe
                675                 680                 685

Leu Val His Val Asn Ser Phe Leu Gln Leu Asp Phe Phe His Gln Leu
            690                 695                 700

Asn Glu Pro Pro Leu Gly Leu Pro Arg Ser Tyr Pro Leu Ser Leu Val
705                 710                 715                 720

Leu Glu His Lys Phe Lys Glu Trp Met Asp Ser Ser Pro Ala Gly Phe
                725                 730                 735

Tyr Phe Ser Asn Tyr Gln Asn Pro Tyr Ile Arg Lys Asp Leu His Asp
                740                 745                 750

Lys Val Leu Ser Gln Lys Phe Glu Pro Pro Lys Met Asn Gln Trp Asn
            755                 760                 765

Lys Val Leu Lys Ser Leu Ile Glu Cys Ala Tyr Asp Met Tyr Phe Glu
            770                 775                 780

Gln Arg His Val Lys Asn Leu Tyr Lys Tyr His Asn Ile Tyr Asn Ile
785                 790                 795                 800

Asn Asn Lys Leu Met Leu Met Arg Asp Ser Ile Asp Leu Tyr Lys Thr
                805                 810                 815

His Phe Asp Asp Val Leu Phe Phe Ala Asp Ile Phe Asn Met Arg Lys
            820                 825                 830

Tyr Met Thr Ala Thr Pro Val Tyr Lys Lys Val Lys Asp Arg Val Tyr
            835                 840                 845

His Thr Leu His Ser Ile Thr Gly Asn Ser Val Asn Phe Tyr Lys Tyr
            850                 855                 860

Gly Ile Ile Tyr Gly Phe Lys Val Asn Lys Glu Ile Leu Lys Glu Val
865                 870                 875                 880

Val Asp Glu Leu Tyr Ser Ile Tyr Asn Phe Asn Thr Asp Ile Phe Thr
                885                 890                 895

Asp Thr Ser Phe Leu Gln Thr Val Tyr Leu Leu Phe Arg Arg Ile Glu
```

-continued

```
                900             905                 910
Glu Thr Tyr Arg Thr Gln Arg Arg Asp Asp Lys Ile Ser Val Asn Asn
            915                 920                 925
Val Phe Phe Met Asn Val Ala Asn Asn Tyr Ser Lys Leu Asn Lys Glu
            930                 935             940
Glu Arg Glu Ile Glu Ile His Asn Ser Met Ala Ser Arg Tyr Tyr Ala
945                 950                 955                 960
Lys Thr Met Phe Ala Ala Phe Gln Met Leu Phe Ser Thr Met Leu Ser
            965                 970                 975
Asn Asn Val Asp Asn Leu Asp Lys Ala Tyr Gly Leu Ser Glu Asn Ile
            980                 985                 990
Gln Val Ala Thr Ser Thr Ser Ala Phe Leu Thr Phe Ala Tyr Val Tyr
            995                 1000                1005
Asn Gly Ser Ile Met Asp Ser Val Thr Asn Ser Leu Leu Pro Pro
            1010                1015                1020
Tyr Ala Lys Lys Pro Ile Thr Gln Leu Lys Tyr Gly Lys Thr Phe
            1025                1030                1035
Val Phe Ser Asn Tyr Phe Met Leu Ala Ser Lys Met Tyr Asp Met
            1040                1045                1050
Leu Asn Tyr Lys Asn Leu Ser Leu Leu Cys Glu Tyr Gln Ala Val
            1055                1060                1065
Ala Ser Ala Asn Phe Tyr Ser Ala Lys Lys Val Gly Gln Phe Ile
            1070                1075                1080
Gly Arg Lys Phe Leu Pro Ile Thr Thr Tyr Phe Leu Val Met Arg
            1085                1090                1095
Ile Ser Trp Thr His Ala Phe Thr Thr Gly Gln His Leu Ile Ala
            1100                1105                1110
Ala Phe Asn Pro Pro Thr Ser Thr Thr Asp Gly Lys Cys Ser Ala
            1115                1120                1125
Pro Ser Tyr Lys Ser Pro Glu Ser Phe Phe Thr His Gly Leu
            1130                1135                1140
Ala Ala Glu Ala Ser Lys Tyr Leu Phe Phe Tyr Phe Phe Thr Asn
            1145                1150                1155
Leu Tyr Leu Asp Ala Tyr Lys Ser Phe Pro Gly Gly Phe Gly Pro
            1160                1165                1170
Ala Ile Lys Glu Gln Thr Gln His Val Gln Glu Gln Thr Tyr Glu
            1175                1180                1185
Arg Lys Pro Ser Val His Ser Phe Asn Arg Asn Phe Phe Met Glu
            1190                1195                1200
Leu Val Asn Gly Phe Met Tyr Ala Phe Cys Phe Phe Ala Ile Ser
            1205                1210                1215
Gln Met Tyr Ala Tyr Phe Glu Asn Ile Asn Phe Tyr Ile Thr Ser
            1220                1225                1230
Asn Phe Arg Phe Leu Asp Arg Tyr Tyr Gly Val Phe Asn Lys Tyr
            1235                1240                1245
Phe Ile Asn Tyr Ala Ile Ile Lys Leu Lys Glu Ile Thr Ser Asp
            1250                1255                1260
Leu Leu Ile Lys Tyr Glu Arg Glu Ala Tyr Leu Asn Met Lys Lys
            1265                1270                1275
Tyr Gly Tyr Leu Gly Glu Val Ile Ala Ala Arg Leu Ser Pro Lys
            1280                1285                1290
Asp Lys Ile Met Asn Tyr Leu His Glu Thr Asn Asp Asp Val Met
            1295                1300                1305
```

| Ser | Asn | Leu | Arg | Arg | Tyr | Asp | Met | Glu | Asn | Ala | Phe | Lys | Asn | Lys |
| --- | --- | --- | --- | --- | --- | --- | --- | --- | --- | --- | --- | --- | --- | --- |
| 1310 | | | | | 1315 | | | | | 1320 | | | | |

| Met | Val | Thr | Tyr | Val | Asp | Asp | Phe | Ala | Phe | Phe | Asp | Asp | Cys | Gly |
| --- | --- | --- | --- | --- | --- | --- | --- | --- | --- | --- | --- | --- | --- | --- |
| 1325 | | | | | 1330 | | | | | 1335 | | | | |

| Lys | Asn | Glu | Gln | Phe | Leu | Asn | Glu | Arg | Cys | Asp | Tyr | Cys | Pro | Val |
| --- | --- | --- | --- | --- | --- | --- | --- | --- | --- | --- | --- | --- | --- | --- |
| 1340 | | | | | 1345 | | | | | 1350 | | | | |

| Ile | Glu | Glu | Val | Glu | Glu | Thr | Glu | Leu | Phe | Thr | Thr | Thr | Gly | Asp |
| --- | --- | --- | --- | --- | --- | --- | --- | --- | --- | --- | --- | --- | --- | --- |
| 1355 | | | | | 1360 | | | | | 1365 | | | | |

| Lys | Asn | Thr | Asn | Glu | Thr | Thr | Glu | Ile | Lys | Lys | Gln | Thr | Ser | Thr |
| --- | --- | --- | --- | --- | --- | --- | --- | --- | --- | --- | --- | --- | --- | --- |
| 1370 | | | | | 1375 | | | | | 1380 | | | | |

| Tyr | Ile | Asp | Thr | Glu | Lys | Met | Asn | Glu | Ala | Asp | Ser | Ala | Asp | Ser |
| --- | --- | --- | --- | --- | --- | --- | --- | --- | --- | --- | --- | --- | --- | --- |
| 1385 | | | | | 1390 | | | | | 1395 | | | | |

| Asp | Asp | Glu | Lys | Asp | Phe | Asp | Thr | Pro | Asp | Asn | Glu | Leu | Met | Ile |
| --- | --- | --- | --- | --- | --- | --- | --- | --- | --- | --- | --- | --- | --- | --- |
| 1400 | | | | | 1405 | | | | | 1410 | | | | |

| Ala | Arg | Phe | His |
| --- | --- | --- | --- |
| 1415 | | | |

<210> SEQ ID NO 79
<211> LENGTH: 4251
<212> TYPE: DNA
<213> ORGANISM: Artificial Sequence
<220> FEATURE:
<223> OTHER INFORMATION: Synthetic

<400> SEQUENCE: 79

| | | | | | |
|---|---|---|---|---|---|
| atggtttcat | ttttaaaaac | tccaatcttt | attttaatta | tcttttata | cttaaatgaa | 60 |
| aaggtaatat | gttcaataaa | tgaaaatcaa | aatgaaaatg | ataccattag | tcaaaatgtc | 120 |
| aaccaacatg | aaaatattaa | tcaaaatgta | aatgataatg | acaatattga | acaattaaaa | 180 |
| tccatgattg | gaaatgatga | actacataag | aatttaacaa | tattagaaaa | attaattta | 240 |
| gagtctttag | aaaagataa | attaaaatat | cctctcctta | aacaaggaac | tgaacaattg | 300 |
| atagatatat | caaaatttaa | taaaaaaaat | attacagatg | cggatgatga | aacgtacatc | 360 |
| atacccaccg | tccaatcaac | gtttcacgat | attgtgaaat | acgaacatct | tataaaagaa | 420 |
| caatcaatag | aaaatttacaa | ttctgatata | tcagataaaa | ttaagaaaaa | aatttttata | 480 |
| gtaagaacat | tgaaaaccat | aaaattaatg | cttataccat | aaactcgta | caaacaaaat | 540 |
| aatgacttga | atctgcact | cgaagaatta | ataatgtat | ttacaaacaa | agaagctcaa | 600 |
| gaggaaagca | gtccaatagg | cgaccatggg | acattcttta | gaaaattgtt | aacacatgtt | 660 |
| agaacaatta | agaaaatga | agatatagaa | aataaaggag | aaacacttat | attaggcgat | 720 |
| aataaaatag | atgtaatgaa | ttcaaacgat | ttctttttta | caaccaactc | aaatgtaaaa | 780 |
| tttatggaaa | atttagatga | tataacaaat | caatatggat | taggtttgat | taatcatcta | 840 |
| ggtcctcatt | taatagcatt | gggtcatttt | accgtattaa | aattagcact | aaaaaattac | 900 |
| aaaaactatt | tgaagcaaa | aagtattaaa | tttttagtt | ggcaaaaaat | tttagagttc | 960 |
| tccatgtccg | atagatttaa | ggttcttgat | atgatgtgta | accatgaatc | tgtatattat | 1020 |
| tccgaaaaaa | aacgtagaaa | aacatatttta | aaagttgaca | gatcaagcac | atcgatggaa | 1080 |
| tgtaatatat | tggaatattt | attacattat | tttaataaat | accaactaga | aataattaaa | 1140 |
| actacacaag | atactgattt | tgacttacat | ggtatgatgg | aacataaata | tataaaagat | 1200 |
| tatttctttt | catttatgtg | taatgatcct | aaggaatgta | ttatttatca | tacgaatcaa | 1260 |
| tttaaaaaag | aagccaacga | agaaaacaca | tttcctgaac | aagaagaacc | taatcgtgaa | 1320 |

```
ataagtgcat ataatttata tttaaattat tactatttca tgaaacgtta tagttcatat    1380
ggagtaaaaa aaacattata tgttcattta ttaaatttaa ctggactttt aaattatgat    1440
acaagatctt atgtgacatc actttattta ccaggatatt acaacgctgt cgaaatgtct    1500
tttacggaag aaaaagagtt ttccaaactt tttgaaagct taatacaatg tattgaaaaa    1560
tgccattcag accaagcaag gcaaatatca aaagatagta atttacttaa tgatataaca    1620
aaatgtgatt tgtgtaaagg agcattctta tattctaaca tgaaattcga tgaagttcct    1680
tcaatgttgc aaaaatttta cttatattta actaaaggtc tcaaaataca aaagtatca     1740 tcactaatca aaacgctaga tatatatcaa gattacagta atttttatc acatgatatt     1800 aattggtaca cattcctatt tttatttaga cttacaagtt ttaaagaaat ttcaaagaaa    1860
aatgttgctg aagcaatgta tttaaatata aaagatgaag atacgttcaa caaaacgata    1920
gtaacaaact attggtaccc atctcctata aaaaaatatt atacattata cgttagaaaa    1980
cacataccaa ataatttagt agatgaattg gagaaattaa tgaaaagtgg cactttagaa    2040
aaaatgaaaa aatctctcac cttttttagta catgtgaatt cattttttaca attagatttt    2100 tttcatcaac ttaatgaacc acctcttgga ttacctcgat catatccttt atccttagtt    2160
cttgaacata aatttaaaga atggatggac agttcgcccg ccggatttta tttttcaaat    2220
tatcaaaatc catatatcag aaaagatttg catgataaag ttttatcaca aaaatttgaa    2280
ccacctaaaa tgaatcagtg gaacaaagtt ttgaagtcat taattgaatg cgcatatgat    2340
atgtattttg aacagagaca tgttaaaaat ttatataaat atcataacat ttataatata    2400
aataacaaat taatgttaat gagagattca attgatttat ataaaaccca ttttgacgac    2460
gtattatttt ttgcggatat atttaatatg agaaaatata tgacagctac accagtatat    2520
aaaaaagtaa aagacagagt gtaccataca ttgcatagta ttacaggaaa ttctgtcaat    2580
ttttataaat atggtattat atatggatt aaagtaaaca aagaaatatt aaaagaagtt    2640
gtcgatgaat tgtattccat ctataatttt aacaccgaca tatttacgga tacttccttt    2700
ttacaaaccg tttatttatt atttagaaga atagaagaaa cttataggac ccaaagaaga    2760
gatgacaaaa taagtgtgaa taacgttttt ttcatgaatg ttgctaataa ttattccaaa    2820
ttaaacaaag aagaaagaga aatcgaaata cataattcca tggcatcaag atattatgca    2880
aaaacgatgt ttgcagcatt tcaaatgtta ttttcaacaa tgttgagcaa caatgtagat    2940
aatcttgata aagcatatgg attaagtgaa aatatccaag tagcaacaag tacttccgct    3000
tttcttactt ttgcatatgt atataacgga agtataatgg atagtgtgac taacagttta    3060
ttgccaccat atgcgaagaa acctataaca caattaaaat atggaaaaac cttcgttttc    3120
tcaaactatt tcatgctagc atccaaaatg tatgatatgt taaattataa aaatttaagt    3180
cttttatgtg aatatcaggc tgtggcaagt gccaatttct actctgctaa aaaggtaggt    3240
cagtttattg gaagaaaatt tttacccata actacatatt ttctagtaat gagaattagt    3300
tggacacatg cttttacaac tggacaacat ttgattgccg cttttaatcc cccaacttct    3360
actactgatg gtaaatgtag tgctcctagt tataaatccc ctgaaagttt tttctttact    3420
cacggacttg ctgctgaagc atccaaatat ttattttttt attttttcac aaatttatac    3480
cttgatgcct acaaatcttt tcctggagga tttggtcctg caataaaaga acaaactcaa    3540
catgttcaag aacaaacgta tgaacgcaaa ccatcagttc atagtttaa tagaaatttt    3600 ttcatggaac tcgtaaatgg attcatgtat gccttttgtt tttttgctat ttcacaaatg    3660
tatgcatatt ttgaaaatat taattttat attacaagta atttccgttt cttggataga    3720
```

```
tattatggtg tattcaataa atattttata aactatgcca taattaaact taaagaaatt    3780
actagtgatc ttttaataaa atatgaacgt gaggcttatt taaatatgaa aaaatatggt    3840
tatttaggtg aagttattgc agctagactt tctcctaaag ataaaattat gaattatttg    3900
cacgaaacta acgacgatgt catgagtaat ttaagaagat atgatatgga aaatgctttc    3960
aaaaacaaaa tggttactta tgtggatgac tttgcttttt ttgatgattg tggcaaaaat    4020
gaacaatttt taaatgaaag atgtgattat tgtcctgtaa ttgaagaggt ggaagaaaca    4080
gaattattta ctaccactgg tgataaaaac actaatgaga ccacggaaat aaaaaaacaa    4140
actagtacat atattgatac tgaaaaaatg aatgaggcgg attccgctga tagcgacgat    4200
gaaaaggatt ttgatactcc tgacaatgaa ttaatgatcg cacgatttca t           4251
```